US009605318B2

(12) United States Patent
Baker et al.

(10) Patent No.: US 9,605,318 B2
(45) Date of Patent: *Mar. 28, 2017

(54) GENE EXPRESSION MARKERS FOR PREDICTING RESPONSE TO CHEMOTHERAPY

(75) Inventors: Joffre B. Baker, Montara, CA (US); Steven Shak, Hillsborough, CA (US); Luca Gianni, Milan (IT)

(73) Assignee: Genomic Health, Inc., Redwood City, CA (US)

( * ) Notice: Subject to any disclaimer, the term of this patent is extended or adjusted under 35 U.S.C. 154(b) by 1091 days.

This patent is subject to a terminal disclaimer.

(21) Appl. No.: 12/941,877

(22) Filed: Nov. 8, 2010

(65) Prior Publication Data

US 2011/0129833 A1  Jun. 2, 2011

Related U.S. Application Data

(62) Division of application No. 11/102,228, filed on Apr. 7, 2005, now Pat. No. 7,871,769.

(60) Provisional application No. 60/561,035, filed on Apr. 9, 2004.

(51) Int. Cl.
  *C12Q 1/68* (2006.01)
(52) U.S. Cl.
  CPC ..... *C12Q 1/6886* (2013.01); *C12Q 2600/106* (2013.01); *Y10S 435/96* (2013.01)
(58) Field of Classification Search
  None
  See application file for complete search history.

(56) References Cited

U.S. PATENT DOCUMENTS

| | | |
|---|---|---|
| 4,699,877 A | 10/1987 | Cline et al. |
| 4,968,603 A | 11/1990 | Slamon et al. |
| 5,015,568 A | 5/1991 | Tsujimoto et al. |
| 5,202,429 A | 4/1993 | Tsujimoto et al. |
| 5,459,251 A | 10/1995 | Tsujimoto et al. |
| RE35,491 E | 4/1997 | Cline et al. |
| 5,670,325 A | 9/1997 | Lapidus et al. |
| 5,741,650 A | 4/1998 | Lapidus et al. |
| 5,830,665 A | 11/1998 | Shuber et al. |
| 5,830,753 A | 11/1998 | Coulie et al. |
| 5,858,678 A | 1/1999 | Chinnadurai |
| 5,861,278 A | 1/1999 | Wong et al. |
| 5,928,870 A | 7/1999 | Lapidus et al. |
| 5,952,178 A | 9/1999 | Lapidus et al. |
| 5,952,179 A | 9/1999 | Chinnadurai |
| 5,962,312 A | 10/1999 | Plowman et al. |
| 5,985,553 A | 11/1999 | King et al. |
| 6,020,137 A | 2/2000 | Lapidus et al. |
| 6,100,029 A | 8/2000 | Lapidus et al. |
| 6,143,529 A | 11/2000 | Lapidus et al. |
| 6,146,828 A | 11/2000 | Lapidus et al. |
| 6,171,798 B1 | 1/2001 | Levine et al. |
| 6,203,993 B1 | 3/2001 | Shuber et al. |
| 6,207,401 B1 | 3/2001 | Plowman et al. |
| 6,207,452 B1 | 3/2001 | Govindaswamy |
| 6,214,558 B1 | 4/2001 | Shuber et al. |
| 6,245,523 B1 | 6/2001 | Altieri |
| 6,248,535 B1 | 6/2001 | Danenberg et al. |
| 6,271,002 B1 | 8/2001 | Linsley et al. |
| 6,322,986 B1 | 11/2001 | Ross |
| 6,331,396 B1 | 12/2001 | Silverman et al. |
| 6,414,134 B1 | 7/2002 | Reed |
| 6,582,919 B2 | 6/2003 | Danenberg |
| 6,602,670 B2 | 8/2003 | Danenberg |
| 6,618,679 B2 | 9/2003 | Loehrlein et al. |
| 6,620,606 B2 | 9/2003 | Bandman et al. |
| 6,696,558 B2 | 2/2004 | Reed et al. |
| 6,716,575 B2 | 4/2004 | Plowman et al. |
| 6,750,013 B2 | 6/2004 | Gish et al. |
| 6,800,737 B2 | 10/2004 | Altieri |
| 6,943,150 B1 | 9/2005 | Altieri |
| 7,081,340 B2 | 7/2006 | Baker et al. |
| 7,171,311 B2 | 1/2007 | Dai et al. |

(Continued)

FOREIGN PATENT DOCUMENTS

| | | |
|---|---|---|
| CA | 2563074 | 10/2005 |
| EP | 108564 B1 | 5/1988 |

(Continued)

OTHER PUBLICATIONS

Chen et al., "Gene amplification in diffuse large B-cell lymphoma (DLBCL) detected by array-based screening predicts clinical outcome", Database BIOSIS [Online] Biosciences Information Service, XP009126487 89(11):760a (2001).
EP Application No. 10177408.1—Extended European Search Report dated Dec. 3, 2010. (9 pages).
JP Application No. 2007-507495—English Translation of Office Action dated Dec. 1, 2010. (10 pages).
Affymetrix Inc "Affymetrix GeneChip Human Genome U95 Version 2 Set HG-U95A" GEO XX XX Mar. 1, 2002 pp. 1-243 XP002330383.
Bertucci F. et al., "Gene Expression Profiles of Poor-Prognosis Primary Breast Cancer Correlate With Survival", Human Molecular Genetics Oxford University Press Surrey GB, Apr. 15, 2002, vol. 11, No. 8, pp. 863-872.

(Continued)

*Primary Examiner* — Samuel Woolwine
(74) *Attorney, Agent, or Firm* — McNeill Baur PLLC

(57) ABSTRACT

The present invention provides sets of genes the expression of which is important in the prognosis of cancer. In particular, the invention provides gene expression information useful for predicting whether cancer patients are likely to have a beneficial treatment response to chemotherapy FHIT; MTA1; ErbB4; FUS; BBC3; IGF1R; CD9; TP53BP1; MUC1; IGFBP5; rhoC; RALBP1; STAT3; ERK1; SGCB; DHPS; MGMT; CRIP2; ErbB3; RAP1GDS1; CCND1; PRKCD; Hepsin; AK055699; ZNF38; SEMA3F; COL1A1; BAG1; AKT1; COL1A2; Wnt.5a; PTPD1; RAB6C; GSTM1, BCL2, ESR1; or the corresponding expression product, is determined, said report includes a prediction that said subject has a decreased likelihood of response to chemotherapy.

18 Claims, 1 Drawing Sheet

(56) References Cited

U.S. PATENT DOCUMENTS

| | | |
|---|---|---|
| 7,526,387 B2 | 4/2009 | Baker et al. |
| 7,569,345 B2 | 8/2009 | Cobleigh et al. |
| 7,622,251 B2 | 11/2009 | Baker et al. |
| 7,695,913 B2 | 4/2010 | Cowens et al. |
| 7,871,769 B2 | 1/2011 | Baker et al. |
| 8,026,060 B2 | 9/2011 | Watson et al. |
| 8,029,995 B2 | 10/2011 | Watson et al. |
| 8,067,178 B2 | 11/2011 | Baker et al. |
| 8,114,597 B2 | 2/2012 | Liew |
| 8,153,378 B2 | 4/2012 | Cowens et al. |
| 8,153,379 B2 | 4/2012 | Watson et al. |
| 8,153,380 B2 | 4/2012 | Watson et al. |
| 8,198,024 B2 | 6/2012 | Watson et al. |
| 8,273,537 B2 | 9/2012 | Watson et al. |
| 8,367,345 B2 | 2/2013 | Cowens et al. |
| 8,632,980 B2 | 1/2014 | Baker et al. |
| 2001/0051344 A1 | 12/2001 | Shalon et al. |
| 2002/0004491 A1 | 1/2002 | Xu et al. |
| 2002/0009736 A1 | 1/2002 | Wang |
| 2002/0039764 A1 | 4/2002 | Rosen et al. |
| 2002/0160395 A1 | 10/2002 | Altieri et al. |
| 2002/0197609 A1* | 12/2002 | Danenberg .............. A61K 33/24 435/6.14 |
| 2003/0073112 A1 | 4/2003 | Zhang et al. |
| 2003/0104499 A1 | 6/2003 | Pressman et al. |
| 2003/0124130 A1* | 7/2003 | Brown .................. 424/155.1 |
| 2003/0165952 A1 | 9/2003 | Linnarsson et al. |
| 2003/0180791 A1 | 9/2003 | Chinnadurai |
| 2003/0198970 A1 | 10/2003 | Roberts |
| 2003/0198972 A1 | 10/2003 | Erlander et al. |
| 2003/0219771 A1 | 11/2003 | Bevilacqua et al. |
| 2003/0224374 A1 | 12/2003 | Dai et al. |
| 2003/0224399 A1* | 12/2003 | Reed et al. .................. 435/6 |
| 2003/0229455 A1 | 12/2003 | Bevilacqua et al. |
| 2004/0009489 A1 | 1/2004 | Golub et al. |
| 2004/0126775 A1 | 7/2004 | Altieri et al. |
| 2004/0133352 A1 | 7/2004 | Bevilacqua et al. |
| 2005/0260646 A1 | 11/2005 | Baker et al. |
| 2005/0266420 A1 | 12/2005 | Pusztai et al. |
| 2005/0272052 A1 | 12/2005 | Shekar et al. |
| 2006/0166230 A1 | 7/2006 | Baker et al. |
| 2006/0281122 A1 | 12/2006 | Bryant et al. |
| 2007/0059737 A1 | 3/2007 | Baker et al. |
| 2007/0065845 A1 | 3/2007 | Baker et al. |
| 2007/0065846 A1 | 3/2007 | Baker et al. |
| 2007/0099209 A1 | 5/2007 | Clarke et al. |
| 2007/0105133 A1 | 5/2007 | Clarke et al. |
| 2007/0141587 A1 | 6/2007 | Baker et al. |
| 2007/0141588 A1 | 6/2007 | Baker et al. |
| 2007/0141589 A1 | 6/2007 | Baker et al. |
| 2008/0182255 A1 | 7/2008 | Baker et al. |
| 2009/0125247 A1 | 5/2009 | Baker et al. |
| 2009/0170075 A1 | 7/2009 | Petrovics et al. |
| 2009/0258795 A1 | 10/2009 | Cowens et al. |
| 2009/0280490 A1 | 11/2009 | Baker et al. |
| 2009/0311702 A1 | 12/2009 | Shak et al. |
| 2010/0124745 A1 | 5/2010 | Liew |
| 2010/0285980 A1 | 11/2010 | Shak et al. |
| 2011/0039269 A1 | 2/2011 | Cowens et al. |
| 2011/0039271 A1 | 2/2011 | Cowens et al. |
| 2011/0059447 A1 | 3/2011 | Liew |
| 2011/0097759 A1 | 4/2011 | Cowens et al. |
| 2011/0111421 A1 | 5/2011 | Cowens et al. |
| 2011/0123990 A1 | 5/2011 | Baker et al. |
| 2011/0129833 A1 | 6/2011 | Baker et al. |
| 2011/0171641 A1 | 7/2011 | Baker et al. |
| 2011/0236903 A1 | 9/2011 | Mcclelland et al. |
| 2012/0028907 A1 | 2/2012 | Shackney |
| 2012/0040842 A1 | 2/2012 | Baker et al. |
| 2012/0171688 A1 | 7/2012 | Cowens et al. |
| 2013/0102492 A1 | 4/2013 | Cowens et al. |
| 2014/0206545 A1 | 7/2014 | Baker et al. |

FOREIGN PATENT DOCUMENTS

| | | |
|---|---|---|
| EP | 1365034 A2 | 11/2003 |
| EP | 1522594 A2 | 4/2005 |
| EP | 2228457 A1 | 9/2010 |
| EP | 2641978 A1 | 9/2013 |
| WO | WO9902714 A1 | 1/1999 |
| WO | WO 00/50595 A2 | 8/2000 |
| WO | WO 00/55173 A1 | 9/2000 |
| WO | WO 00/70085 A2 | 11/2000 |
| WO | WO 01/25250 A1 | 4/2001 |
| WO | WO 01/40466 A2 | 6/2001 |
| WO | WO 01/55320 A2 | 8/2001 |
| WO | WO 01/70979 A2 | 9/2001 |
| WO | WO 02/00677 A1 | 1/2002 |
| WO | WO 02/06526 A1 | 1/2002 |
| WO | WO 02/08260 A2 | 1/2002 |
| WO | WO 02/08282 A2 | 1/2002 |
| WO | WO 02/08765 A2 | 1/2002 |
| WO | WO 0208261 A2 | 1/2002 |
| WO | WO 02/10436 A2 | 2/2002 |
| WO | WO 02/17852 A2 | 3/2002 |
| WO | WO-0231209 A2 | 4/2002 |
| WO | WO 02/46467 | 6/2002 |
| WO | WO 02/055988 A2 | 7/2002 |
| WO | WO 02/059377 A2 | 8/2002 |
| WO | WO 02/068579 A2 | 9/2002 |
| WO | WO 02/077197 | 10/2002 |
| WO | WO 02/103320 A2 | 12/2002 |
| WO | WO-02103320 A2 | 12/2002 |
| WO | WO 03/011897 A1 | 2/2003 |
| WO | WO 03/057916 | 7/2003 |
| WO | WO 03/078662 A1 | 9/2003 |
| WO | WO 03/083096 A2 | 10/2003 |
| WO | WO 2004/065583 A3 | 8/2004 |
| WO | WO 2004/074518 A1 | 9/2004 |
| WO | WO 2004/111603 A3 | 12/2004 |
| WO | WO 2005/008213 A3 | 1/2005 |
| WO | WO-2005015236 A2 | 2/2005 |
| WO | WO 2005/039382 A3 | 5/2005 |
| WO | WO 2006/052731 A3 | 5/2006 |
| WO | WO 2006/052862 A1 | 5/2006 |
| WO | WO-2007073220 A1 | 6/2007 |
| WO | WO 2007/123772 A3 | 11/2007 |
| WO | WO 2009/026128 A2 | 2/2009 |
| WO | WO 2009/140304 A1 | 11/2009 |

OTHER PUBLICATIONS

Brabender J. et al., "Epidermal Growth Factor Receptor and HER2-neu mRNA Expression in Non-Small Cell Lung Cancer Is Correlated with Survival Clinical Cancer Research", Jul. 1, 2001, vol. 7, pp. 1850-1855.

Cambridge Healthtech Institute Conference Agenda; "Enabling Molecular Profiling With Cellular Resolution: Microgenomics Using Homogeneous Cell Samples"; Dec. 2002; 5 pgs.

Cheng et al., "SCUBE2 Suppresses Breast Tumor Cell Proliferation and Confers a Favorable Prognosis in Invasive Breast Cancer", Cancer Res., Apr. 15, 2009, vol. 69, No. 8, pp. 3634-3641.

Co-pending U.S. Appl. No. 12/478,632, filed Jun. 4, 2009.

Co-pending U.S. Appl. No. 12/576,898, filed Oct. 9, 2009.

Co-pending U.S. Appl. No. 12/616,039, filed Nov. 10, 2009.

Ding C. et al., "A high-throughput gene expression analysis technique using competitive PCR and matrix-assisted laser desorption ionization time-of-flight MS PNAS", Mar. 18, 2003, vol. 100, No. 6, pp. 3059-3064.

Ding Z. et al., "Multidrug resistance in human cervical cells is associated with enhanced expression of anti-apoptotic proteins BAG-1 and Bcl-XL and reduced caspase-3 activity," Proceedings of the America Association for Cancer Research Annual Meeting,91st Annual Meeting of the American Association for Cancer Research; San Francisco, California, USA, 2000, 41, 404.

EP Patent Application Serial No. 09014283.7 extended European search report, dated Feb. 12, 2010.

GenBank GI:10190747 [online] Sep. 28, 2008 [retrieved on May 1, 2009] retrieved from http://www.ncbi.nlm.nih.gov/nuccore/10190747 (6 pages).

(56) References Cited

OTHER PUBLICATIONS

Johnson S. et al., "Increased expression of TATA-binding protein the central transcription factor can contribute to oncogenesis", Molecular and Cellular Biology, May 1, 2003, vol. 23, No. 9, pp. 3043-3051.

Kitada S. et al., "Expression of apoptosis-regulating proteins in chronic lymphocytic leukemia: Correlations with in vitro and in vivo chemoresponses," Blood, 1998, 91 (9), 3379-3389.

Kononen J. et al., "Tissue microarrays for high-throughput molecular profiling of tumor specimens", Nature Medicine, 1998, vol. 4, No. 7, pp. 844-847.

Korfee et al., "The Role of DNA-Microarray in Translational Cancer Research ", Current Pharmacogenomics, 2005, vol. 3, pp. 201-216.

Kroese et al., "Genetic tests and their evaluation: can we answer the key questions?", Genetics in Medicine, 2004, vol. 6, pp. 475-480.

Lucentini, "Gene Association Studies Typically Wrong", The Scientist, 2004, vol. 18, No. 24, pp. 20.

Murphy et al., "Gene expression profiling in breast cancer: towards individualising patient management", Pathology, 2005, vol. 37, No. 4, pp. 271-277.

Muss H. B. et al., "C-ERBB-2 Expression and Response to Adjuvant Therapy in Women With Node-Positive Early Breast Cancer", New England Journal of Medicine, May 5, 1994, vol. 330, No. 18, pp. 1260-1266.

Nessling et al., "Candidate genes in breast cancer revealed by microarray-based comparative genomic hybridization of archived tissue," Cancer Res., 2005, pp. 439-447, vol. 65(2).

Nishidate, T. et al., "Genome-wide gene-expression profiles of breast-cancer cells purified with laser microbeam microdissection: Identification of genes associated with progression and metastasis," International Journal of Oncology, 2004, pp. 797-819, vol. 25.

Pusztai L. et al., "Expression of BAG-1 and BcL-2 proteins before and after neoadjuvant chemotherapy of locally enhanced breast cancer," Cancer Investigation, 2004, 22 ( 2) , 248-256.

Ring A. E. et al., "Predictors of Response to Systemic Therapy in Breast Cancer", Forum Genova IT, 2002, vol. 12, No. 1, pp. 19-32.

Rundle, A. et al., "The association between glutathione S-transferase M1 genotype and polycyclic aromatic hydrocarbon-DNA adducts in breast tissue," Cancer, Epidemiology, Biomarkers, and Prevention, 2000, pp. 1079-1085, vol. 9.

Shen, R. et al., "Prognostic meta-signature of breast cancer developed by two-stage mixture modeling of microarray data," BMC Genomics, 2004, pp. 94, vol. 5.

Sorlie T. et al., "Gene expression patterns of breast carcinomas distinguish tumor subclasses with clinical implications", Proceedings of the National Academy of Sciences USA, Sep. 11, 2001, vol. 98, No. 19, pp. 10869-10874.

Sotiriou Christos et al., "Gene expression profiles derived from fine needle aspiration correlate with response to systemic chemotherapy in breast cancer", Breast Cancer Research, 2002, vol. 4, No. 3, pp. R3-1-R3-8.

Stearns V. et al., "A prospective randomized pilot study to evaluate predictors of response in serial core biopsies to single agent neoadjuvant doxorubicin or paclitaxel for patients with locally advanced breast cancer", Clinical Cancer Research an Official Journal of the American Association for Cancer Research Jan. 2003, Jan. 1, 2003, vol. 9, , No. 1, pp. 124-133.

Stein, D. et al., "The SH2 domain protein GRB-7 is co-amplified, overexpressed and in a tight complex with HER2 in breast cancer," EMBO Journal, 1994, pp. 1331-1340, vol. 13, No. 6.

Townsend, P. et al. "BAG-1 expression in human breast cancer: interrelationship between BAG-1 RNA, protein, HSC70 expression and clinico-pathological data," Journal of Pathology, 2002, pp. 51-59, vol. 197.

Turner, B. et al., "BAG-1: A novel biomarker predicting long-term survival in early-stage breast cancer," Journal of Clinical Oncology, 2001, pp. 992-1000, vol. 19, No. 4.

Van de Vijver et al., "A Gene-Expression Signature as a Predictor of Survival in Beast Cancer", The New England Journal of Medicine, Dec. 19, 2002, vol. 347, No. 25, pp. 1999-2009.

Veer Van T. L. J. et al., "Gene expression profiling predicts clinical outcome of breast cancer", Nature MacMillan Journals Ltd. London GB, Jan. 31, 2002, vol. 415, No. 6871, pp. 530-536.

Yang L. I. et al., "Badge Beads Array for the Detection of Gene Expression a High-Throughput Diagnostic Bioassay", Genome Research, 2001, vol. 11, pp. 1888-1898.

Fukumoto et al., "Comprehensive analysis using human breast cancer as a model to determine whether tumors expressing a drug-resistance phenotype are reflective of clinical resistance or prognosis," Strides in Cancer Therapy, vol. 20, pp. 73-84 (2001) (with translation).

Japanese Office Action from JP Patent App. No. 2007-507495, dated Dec. 15, 2011 (with translation).

Kubota, "The role of anthracyclines in breast cancer treatment and the multidrug resistance mechanism," Japanese Journal of Cancer Clinics, vol. 48, No. 12, pp. 753-761 (2002) (with translation).

Yang et al., "Overexpression of p27 protein in human breast cancer correlates with in vitro resistance to doxorubicin and mitomycin C," Anticancer Research, vol. 20, pp. 4319-4322 (2000).

Clark-Langone K.M., et al., "Biomarker Discovery for Colon Cancer Using a 761 Gene RT-PCR Assay," BMC Genomics, 2007, vol. 8:279, 18 pages.

Sjöström J., et al., "The Predictive Value of bcl-2, bax, bcl-xL, bag-1, fas, and fasL for Chemotherapy Response in Advanced Breast Cancer", Clinical Cancer Research, 2002, vol. 8, pp. 811-816.

Breast Cancer Research and Treatment, Jan. 2004, vol. 88, No. Suppl. 1, p. S22, 107 (Abstract only).

Anelli et al., "Correlation of p53 Status With Outcome of Neoadjuvant Chemotherapy Using Paclitaxel and Doxorubicin in Stage IIIB Breast Cancer", Annals of Oncology, 2003, vol. 14, pp. 428-432.

Chang et al., "Gene Expression Profiling for the Prediction of Therapeutic Response to Docetaxel in Patients With Breast Cancer", Mechanisms of Disease, 2003, vol. 362, pp. 362-369.

Extended European Search Report dated Aug. 24, 2015, for European Patent Application No. 15173816.8.

Duan et al., "GBP1 Overexpression is Associated with a Paclitaxel Resistance Phenotype", Cancer Chemother Pharmacol, vol. 57, 2006, pp. 25-33.

Lubeseder-Martellato et al., "Guanylate-Binding Protein-1 Expression is Selectively Induced by Inflammatory Cytokines and is an Activation Marker of Endothelial Cells During Inflammatory Diseases", American Journal of Pathology, vol. 161, 2002, pp. 1749-1759.

Rabinowich et al., "Expression and Activity of Signaling Molecules in T Lymphocytes Obtained from Patients with Metastatic Melanoma before and after Interleukin 2 Therapy", Clinical Cancer Research, Aug. 1996, vol. 2, pp. 1263-1274.

Taylor, et al., "Modulation of CD3-Zeta as a Marker of Clinical Response to IL-2 Therapy in Ovarian Cancer Patients", Gynecologic Oncology, vol. 94, 2004, pp. 54-60.

Affymetrix, "Affymetrix Human Genome U95A Array", NCBI GEO, Platform GPL91, available online at http://www.ncbi.nlm.nih.gov/geo/query/acc.cgi?acc=GPL91, Mar. 2002, [retrieved Sep. 12, 2015].

\* cited by examiner

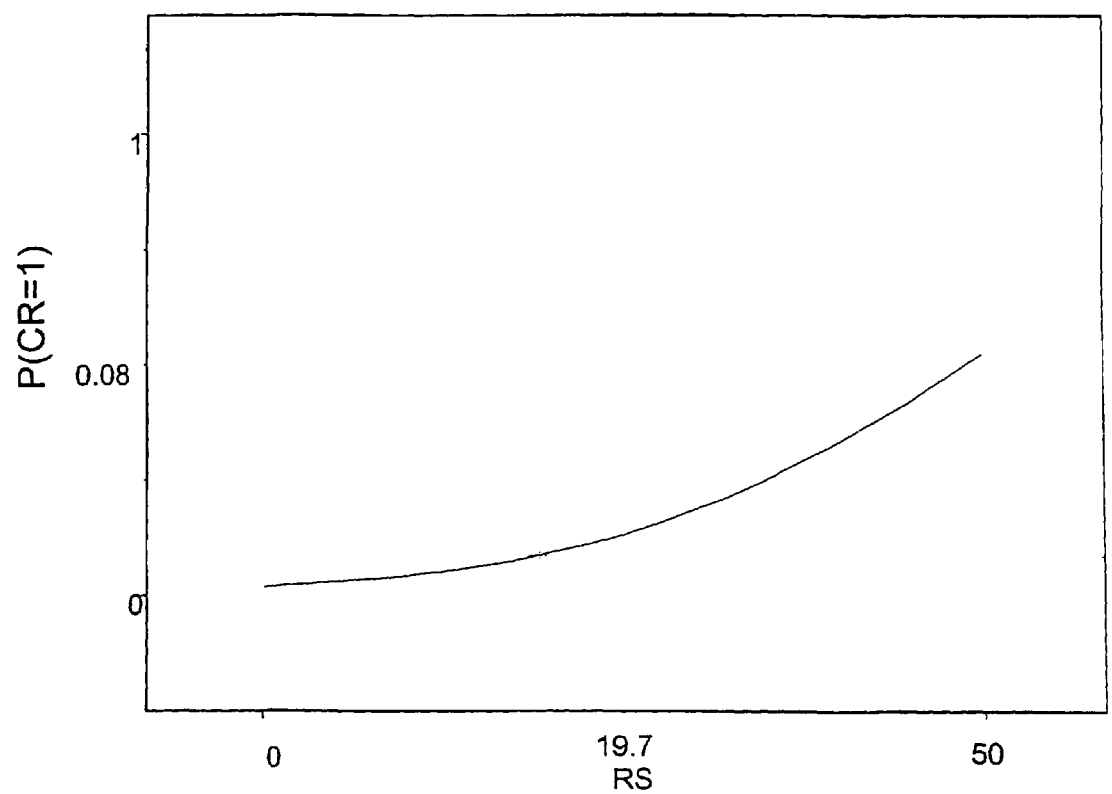

GENE EXPRESSION MARKERS FOR PREDICTING RESPONSE TO CHEMOTHERAPY

This is a divisional application of U.S. application Ser. No. 11/102,228, filed Apr. 7, 2005, which claims priority to U.S. Provisional Application No. 60/561,035, filed Apr. 9, 2004, both of which are hereby incorporated by reference.

BACKGROUND OF THE INVENTION

Field of the Invention

The present invention provides sets of genes the expression of which is important in the prognosis of cancer. In particular, the invention provides gene expression information useful for predicting whether cancer patients are likely to have a beneficial treatment response to chemotherapy.

Description of the Related Art

Oncologists have a number of treatment options available to them, including different combinations of chemotherapeutic drugs that are characterized as "standard of care," and a number of drugs that do not carry a label claim for particular cancer, but for which there is evidence of efficacy in that cancer. Best likelihood of good treatment outcome requires that patients be assigned to optimal available cancer treatment, and that this assignment be made as quickly as possible following diagnosis. In particular, it is important to determine the likelihood of patient response to "standard of care" chemotherapy because chemotherapeutic drugs such as anthracyclines and taxanes have limited efficacy and are toxic. The identification of patients who are most or least likely to respond thus could increase the net benefit these drugs have to offer, and decrease the net morbidity and toxicity, via more intelligent patient selection.

Currently, diagnostic tests used in clinical practice are single analyte, and therefore do not capture the potential value of knowing relationships between dozens of different markers. Moreover, diagnostic tests are frequently not quantitative, relying on immunohistochemistry. This method often yields different results in different laboratories, in part because the reagents are not standardized, and in part because the interpretations are subjective and cannot be easily quantified. RNA-based tests have not often been used because of the problem of RNA degradation over time and the fact that it is difficult to obtain fresh tissue samples from patients for analysis. Fixed paraffin-embedded tissue is more readily available and methods have been established to detect RNA in fixed tissue. However, these methods typically do not allow for the study of large numbers of genes (DNA or RNA) from small amounts of material. Thus, traditionally fixed tissue has been rarely used other than for immunohistochemistry detection of proteins.

In the last few years, several groups have published studies concerning the classification of various cancer types by microarray gene expression analysis (see, e.g. Golub et al. *Science* 286:531-537 (1999); Bhattacharjae et al., *Proc. Natl. Acad. Sci. USA* 98:13790-13795 (2001); Chen-Hsiang et al., *Bioinformatics* 17 (Suppl. 1):S316-S322 (2001); Ramaswamy et al. *Proc. Natl. Acad. Sci. USA* 98:15149-15154 (2001)). Certain classifications of human breast cancers based on gene expression patterns have also been reported (Martin et al., *Cancer Res.* 60:2232-2238 (2000); West et al., *Proc. Natl. Acad. Sci. USA* 98:11462-11467 (2001); Sorlie et al., *Proc. Natl. Acad. Sci. USA* 98:10869-10874 (2001); Yan et al., *Cancer Res.* 61:8375-8380 (2001)). However, these studies mostly focus on improving and refining the already established classification of various types of cancer, including breast cancer, and generally do not provide new insights into the relationships of the differentially expressed genes, and do not link the findings to treatment strategies in order to improve the clinical outcome of cancer therapy.

Although modern molecular biology and biochemistry have revealed hundreds of genes whose activities influence the behavior of tumor cells, state of their differentiation, and their sensitivity or resistance to certain therapeutic drugs, with a few exceptions, the status of these genes has not been exploited for the purpose of routinely making clinical decisions about drug treatments. One notable exception is the use of estrogen receptor (ER) protein expression in breast carcinomas to select patients to treatment with anti-estrogen drugs, such as tamoxifen. Another exceptional example is the use of ErbB2 (Her2) protein expression in breast carcinomas to select patients with the Her2 antagonist drug Herceptin® (Genentech, Inc., South San Francisco, Calif.).

Despite recent advances, the challenge of cancer treatment remains to target specific treatment regimens to pathogenically distinct tumor types, and ultimately personalize tumor treatment in order to maximize outcome. Hence, a need exists for tests that simultaneously provide predictive information about patient responses to the variety of treatment options. This is particularly true for breast cancer, the biology of which is poorly understood. It is clear that the classification of breast cancer into a few subgroups, such as the ErbB2 positive subgroup, and subgroups characterized by low to absent gene expression of the estrogen receptor (ER) and a few additional transcriptional factors (Peron et al. *Nature* 406:747-752 (2000)), does not reflect the cellular and molecular heterogeneity of breast cancer, and does not allow the design of treatment strategies maximizing patient response. Breast cancer is the most common type of cancer among women in the United States and is the leading cause of cancer deaths among women ages 40-59. Therefore, there is a particularly great need for a clinically validated breast cancer test predictive of patient response to chemotherapy.

SUMMARY OF THE INVENTION

The present invention provides gene sets useful in predicting the response of cancer, e.g. breast cancer patients to chemotherapy. In addition, the invention provides a clinically validated cancer, e.g. breast cancer, test, predictive of patient response to chemotherapy, using multi-gene RNA analysis. The present invention accommodates the use of archived paraffin-embedded biopsy material for assay of all markers in the relevant gene sets, and therefore is compatible with the most widely available type of biopsy material.

In one aspect, the present invention concerns a method for predicting the response of a subject diagnosed with cancer to chemotherapy comprising determining the expression level of one or more prognostic RNA transcripts or their expression products in a biological sample comprising cancer cells obtained from said subject, wherein the predictive RNA transcript is the transcript of one or more genes selected from the group consisting of TBP; ILT.2; ABCC5; CD18; GATA3; DICER1; MSH3; GBP1; IRS1; CD3z; fasl; TUBB; BAD; ERCC1; MCM6; PR; APC; GGPS1; KRT18; ESRRG; E2F1; AKT2; A.Catenin; CEGP1; NPD009; MAPK14; RUNX1; ID2; G.Catenin; FBXO5; FHIT; MTA1; ERBB4; FUS; BBC3; IGF1R; CD9; TP53BP1; MUC1; IGFBP5; rhoC; RALBP1; CDC20; STAT3; ERK1; HLA.DPB1; SGCB; CGA; DHPS; MGMT; CRIP2; MMP12; ErbB3; RAP1GDS1; CDC25B; IL6; CCND1; CYBA; PRKCD; DR4; Hepsin; CRABP1; AK055699; Contig.51037; VCAM1; FYN; GRB7; AKAP.2; RASSF1; MCP1; ZNF38; MCM2; GBP2; SEMA3F; CD31; COL1A1; ER2; BAG1; AKT1; COL1A2; STAT1; Wnt.5a; PTPD1; RAB6C; TK1, ErbB2, CCNB1, BIRC5, STK6, MKI67, MYBL2, MMP11, CTSL2, CD68, GSTM1, BCL2, ESR1 wherein (a) for every unit of increased expression of one or more of ILT.2; CD18; GBP1; CD3z; fasl MCM6; E2F1; ID2; FBXO5; CDC20; HLA.DPB1; CGA; MMP12; CDC25B; IL6; CYBA; DR4; CRABP1; Contig.51037; VCAM1; FYN; GRB7; AKAP.2; RASSF1; MCP1; MCM2; GBP2; CD31; ER2; STAT1; TK1; ERBB2, CCNB1, BIRC5, STK6, MKI67, MYBL2, MMP11, CTSL2 and CD68; or the corresponding expression product, said subject is predicted to have an increased likelihood of response to chemotherapy; and (b) for every unit of increased expression of one or more of TBP; ABCC5; GATA3; DICER1; MSH3; IRS1; TUBB; BAD; ERCC1; PR; APC; GGPS1; KRT18; ESRRG; AKT2; A.Catenin; CEGP1; NPD009; MAPK14; RUNX1; G.Catenin; FHIT; MTA1; ErbB4; FUS; BBC3; IGF1R; CD9; TP53BP1; MUC1; IGFBP5; rhoC; RALBP1; STAT3; ERK1; SGCB; DHPS; MGMT; CRIP2; ErbB3; RAP1GDS1; CCND1; PRKCD; Hepsin; AK055699; ZNF38; SEMA3F; COL1A1; BAG1; AKT1; COL1A2; Wnt.5a; PTPD1; RAB6C; GSTM1; BCL2; ESR1; or the corresponding expression product, said subject is predicted to have a decreased likelihood of response to chemotherapy.

In a particular embodiment, in the above method the predictive RNA transcript is the transcript of one or more genes selected from the group consisting of TBP; ILT.2; ABCC5; CD18; GATA3; DICER1; MSH3; GBP1; IRS1; CD3z; fasl; TUBB; BAD; ERCC1; MCM6; PR; APC; GGPS1; KRT18; ESRRG; E2F1; AKT2; A.Catenin; CEGP1; NPD009; MAPK14; RUNX1; ID2; G.Catenin; FBXO5; FHIT; MTA1; ERBB4; FUS; BBC3; IGF1R; CD9; TP53BP1; MUC1; IGFBP5; rhoC; RALBP1; CDC20; STAT3; ERK1; HLA.DPB1; SGCB; CGA; DHPS; MGMT; CRIP2; MMP12; ErbB3; RAP1GDS1; CDC25B; IL6; CCND1; CYBA; PRKCD; DR4; Hepsin; CRABP1; AK055699; Contig.51037; VCAM1; FYN; GRB7; AKAP.2; RASSF1; MCP1; ZNF38; MCM2; GBP2; SEMA3F; CD31; COL1A1; ER2; BAG1; AKT1; COL1A2; STAT1; Wnt.5a; PTPD1; RAB6C; and TK1.

In another embodiment, the response is a complete pathological response.

In a preferred embodiment, the subject is a human patient.

The cancer can be any types of cancer but preferably is a solid tumor, such as breast cancer, ovarian cancer, gastric cancer, colon cancer, pancreatic cancer, prostate cancer and lung cancer.

If the tumor is breast cancer, it can, for example, be invasive breast cancer, or stage II or stage III breast cancer.

In a particular embodiment, the chemotherapy is adjuvant chemotherapy.

In another embodiment, the chemotherapy is neoadjuvant chemotherapy.

The neoadjuvant chemotherapy may, for example, comprise the administration of a taxane derivative, such as docetaxel and/or paclitaxel, and/or other anti-cancer agents, such as, members of the anthracycline class of anti-cancer agents, doxorubicin, topoisomerase inhibitors, etc.

The method may involve determination of the expression levels of at least two, or at least five, or at least ten, or at least 15 of the prognostic transcripts listed above, or their expression products.

The biological sample may be e.g. a tissue sample comprising cancer cells, where the tissue can be fixed, paraffin-embedded, or fresh, or frozen.

In a particular embodiment, the tissue is from fine needle, core, or other types of biopsy.

In another embodiment, the tissue sample is obtained by fine needle aspiration, bronchial lavage, or transbronchial biopsy.

The expression level of said prognostic RNA transcript or transcripts can be determined, for example, by RT-PCR or an other PCR-based method, immunohistochemistry, proteomics techniques, or any other methods known in the art, or their combination.

In an embodiment, the assay for the measurement of said prognostic RNA transcripts or their expression products is provided is provided in the form of a kit or kits.

In another aspect, the invention concerns an array comprising polynucleotides hybridizing to a plurality of the following genes: TBP; ILT.2; ABCC5; CD18; GATA3; DICER1; MSH3; GBP1; IRS1; CD3z; fasl; TUBB; BAD; ERCC1; MCM6; PR; APC; GGPS1; KRT18; ESRRG; E2F1; AKT2; A.Catenin; CEGP1; NPD009; MAPK14; RUNX1; ID2; G.Catenin; FBXO5; FHIT; MTA1; ERBB4; FUS; BBC3; IGF1R; CD9; TP53BP1; MUC1; IGFBP5; rhoC; RALBP1; CDC20; STAT3; ERK1; HLA.DPB1; SGCB; CGA; DHPS; MGMT; CRIP2; MMP12; ErbB3; RAP1GDS1; CDC25B; IL6; CCND1; CYBA; PRKCD; DR4; Hepsin; CRABP1; AK055699; Contig.51037; VCAM1; FYN; GRB7; AKAP.2; RASSF1; MCP1; ZNF38; MCM2; GBP2; SEMA3F; CD31; COL1A1; ER2; BAG1; AKT1; COL1A2; STAT1; Wnt.5a; PTPD1; RAB6C; TK1, ErbB2, CCNB1, BIRC5, STK6, MKI67, MYBL2, MMP11, CTSL2, CD68, GSTM1, BCL2, ESR1.

In an embodiment, the array comprises polynucleotides hybridizing to a plurality of the following genes: TBP; ILT.2; ABCC5; CD18; GATA3; DICER1; MSH3; GBP1; IRS1; CD3z; fasl; TUBB; BAD; ERCC1; MCM6; PR; APC; GGPS1; KRT18; ESRRG; E2F1; AKT2; A.Catenin; CEGP1; NPD009; MAPK14; RUNX1; ID2; G.Catenin; FBXO5; FHIT; MTA1; ERBB4; FUS; BBC3; IGF1R; CD9; TP53BP1; MUC1; IGFBP5; rhoC; RALBP1; CDC20; STAT3; ERK1; HLA.DPB1; SGCB; CGA; DHPS; MGMT; CRIP2; MMP12; ErbB3; RAP1GDS1; CDC25B; IL6; CCND1; CYBA; PRKCD; DR4; Hepsin; CRABP1; AK055699; Contig.51037; VCAM1; FYN; GRB7; AKAP.2; RASSF1; MCP1; ZNF38; MCM2; GBP2; SEMA3F; CD31; COL1A1; ER2; BAG1; AKT1; COL1A2; STAT1; Wnt.5a; PTPD1; RAB6C; TK1.

In another embodiment, the array comprises polynucleotides hybridizing to a plurality of the following genes: ILT.2; CD18; GBP1; CD3z; fasl; MCM6; E2F1; ID2; FBXO5; CDC20; HLA.DPB1; CGA; MMP12; CDC25B; IL6; CYBA; DR4; CRABP1; Contig.51037; VCAM1; FYN; GRB7; AKAP.2; RASSF1; MCP1; MCM2; GBP2; CD31; ER2; STAT1; TK1; ERBB2, CCNB1, BIRC5, STK6, MKI67, MYBL2, MMP11, CTSL2 and CD68.

In yet another embodiment, the array comprises polynucleotides hybridizing to a plurality of the following genes: ILT.2; CD18; GBP1; CD3z; fasl; MCM6; E2F1; ID2; FBXO5; CDC20; HLA.DPB1; CGA; MMP12; CDC25B; IL6; CYBA; DR4; CRABP1; Contig.51037; VCAM1; FYN; GRB7; AKAP.2; RASSF1; MCP1; MCM2; GBP2; CD31; ER2; STAT1; TK1

In a still further embodiment, the array comprises polynucleotides hybridizing to a plurality of the following genes: TBP; ABCC5; GATA3; DICER1; MSH3; IRS1; TUBB; BAD; ERCC1; PR; APC; GGPS1; KRT18; ESRRG; AKT2;

A.Catenin; CEGP1; NPD009; MAPK14; RUNX1; G.Catenin; FHIT; MTA1; ErbB4; FUS; BBC3; IGF1R; CD9; TP53BP1; MUC1; IGFBP5; rhoC; RALBP1; STAT3; ERK1; SGCB; DHPS; MGMT; CRIP2; ErbB3; RAP1GDS1; CCND1; PRKCD; Hepsin; AK055699; ZNF38; SEMA3F; COL1A1; BAG1; AKT1; COL1A2; Wnt.5a; PTPD1; RAB6C; GSTM1, BCL2, ESR1.

In another embodiment, the array comprises polynucleotides hybridizing to a plurality of the following genes: TBP; ABCC5; GATA3; DICER1; MSH3; IRS1; TUBB; BAD; ERCC1; PR; APC; GGPS1; KRT18; ESRRG; AKT2; A.Catenin; CEGP1; NPD009; MAPK14; RUNX1; G.Catenin; FHIT; MTA1; ErbB4; FUS; BBC3; IGF1R; CD9; TP53BP1; MUC1; IGFBP5; rhoC; RALBP1; STAT3; ERK1; SGCB; DHPS; MGMT; CRIP2; ErbB3; RAP1GDS1; CCND1; PRKCD; Hepsin; AK055699; ZNF38; SEMA3F; COL1A1; BAG1; AKT1; COL1A2; Wnt.5a; PTPD1; RAB6C.

In various embodiments, the array comprises at least five, or at least 10, or at least 15, or at least 10 of such polynucleotides.

In a particular embodiment, the array comprises polynucleotides hybridizing to all of the genes listed above.

In another particular embodiment, the array comprises more than one polynucleotide hybridizing to the same gene.

In another embodiment, at least one of the polynucleotides comprises an intron-based sequence the expression of which correlates with the expression of a corresponding exon sequence.

In various embodiments, the polynucleotides can be cDNAs or oligonucleotides.

In another aspect, the invention concerns a method of preparing a personalized genomics profile for a patient comprising the steps of:

(a) determining the normalized expression levels of the RNA transcripts or the expression products of a gene or gene set selected from the group consisting of TBP; ILT.2; ABCC5; CD18; GATA3; DICER1; MSH3; GBP1; IRS1; CD3z; fasl; TUBB; BAD; ERCC1; MCM6; PR; APC; GGPS1; KRT18; ESRRG; E2F1; AKT2; A.Catenin; CEGP1; NPD009; MAPK14; RUNX1; ID2; G.Catenin; FBXO5; FHIT; MTA1; ERBB4; FUS; BBC3; IGF1R; CD9; TP53BP1; MUC1; IGFBP5; rhoC; RALBP1; CDC20; STAT3; ERK1; HLA.DPB1; SGCB; CGA; DHPS; MGMT; CRIP2; MMP12; ErbB3; RAP1GDS1; CDC25B; IL6; CCND1; CYBA; PRKCD; DR4; Hepsin; CRABP1; AK055699; Contig.51037; VCAM1; FYN; GRB7; AKAP.2; RASSF1; MCP1; ZNF38; MCM2; GBP2; SEMA3F; CD31; COL1A1; ER2; BAG1; AKT1; COL1A2; STAT1; Wnt.5a; PTPD1; RAB6C; TK1; ErbB2, CCNB1, BIRC5, STK6, MKI67, MYBL2, MMP11, CTSL2, CD68, GSTM1, BCL2, ESR1, in a cancer cell obtained from said patient; and (b) creating a report summarizing the data obtained by the gene expression analysis.

In a specific embodiment, if increased expression of one or more of ILT.2; CD18; GBP1; CD3z; fasl; MCM6; E2F1; ID2; FBXO5; CDC20; HLA.DPB1; CGA; MMP12; CDC25B; IL6; CYBA; DR4; CRABP1; Contig.51037; VCAM1; FYN; GRB7; AKAP.2; RASSF1; MCP1; MCM2; GBP2; CD31; ER2; STAT1; TK1; ERBB2, CCNB1, BIRC5, STK6, MKI67, MYBL2, MMP11, CTSL2 and CD68; or the corresponding expression product, is determined, the report includes a prediction that said subject has an increased likelihood of response to chemotherapy. In this case, in a particular embodiment, the method includes the additional step of treating the patient with a chemotherapeutic agent.

In the foregoing method, if increased expression of one or more of TBP; ABCC5; GATA3; DICER1; MSH3; IRS1; TUBB; BAD; ERCC1; PR; APC; GGPS1; KRT18; ESRRG; AKT2; A.Catenin; CEGP1; NPD009; MAPK14; RUNX1; G.Catenin; FHIT; MTA1; ErbB4; FUS; BBC3; IGF1R; CD9; TP53BP1; MUC1; IGFBP5; rhoC; RALBP1; STAT3; ERK1; SGCB; DHPS; MGMT; CRIP2; ErbB3; RAP1GDS1; CCND1; PRKCD; Hepsin; AK055699; ZNF38; SEMA3F; COL1A1; BAG1; AKT1; COL1A2; Wnt.5a; PTPD1; RAB6C; GSTM1, BCL2, ESR1; or the corresponding expression product, is determined, the report includes a prediction that said subject has a decreased likelihood of response to chemotherapy.

In another aspect, the invention concerns a method for determining the likelihood of the response of a patient to chemotherapy, comprising:

(a) determining the expression levels of the RNA transcripts of following genes ACTB, BAG1, BCL2, CCNB1, CD68, SCUBE2, CTSL2, ESR1, GAPD, GRB7, GSTM1, GUSB, ERBB2, MK167, MYBL2, PGR, RPLPO, STK6, MMP11, BIRC5, TFRC, or their expression products, and (b) calculating the recurrence score (RS).

In an embodiment, patients having an RS>50 are in the upper 50 percentile of patients who are likely to respond to chemotherapy.

In another embodiment, patients having an RS<35 are in the lower 50 percentile of patients who are likely to response to chemotherapy.

In a further embodiment, RS is determined by creating the following gene subsets:

(i) growth factor subset: GRB7 and HER2;
(ii) estrogen receptor subset: ER, PR, Bcl2, and CEGP1;
(iii) proliferation subset: SURV, Ki.67, MYBL2, CCNB1, and STK15; and
(iv) invasion subset: CTSL2, and STMY3;

wherein a gene within any of subsets (i)-(iv) can be substituted by substitute gene which coexpresses with said gene in said tumor with a Pearson correlation coefficient of 0.40; and (c) calculating the recurrence score (RS) for said subject by weighting the contributions of each of subsets (i)-(iv), to breast cancer recurrence.

The foregoing method may further comprise determining the RNA transcripts of CD68, GSTM1 and BAG1 or their expression products, or corresponding substitute genes or their expression products, and including the contribution of said genes or substitute genes to breast cancer recurrence in calculating the RS RS may, for example, be determined by using the following equation:

$$RS=(0.23 \text{ to } 0.70) \times GRB7axisthresh-(0.17 \text{ to } 0.55) \times ERaxis+(0.52 \text{ to } 1.56) \times prolifaxisthresh+(0.07 \text{ to } 0.21) \times invasionaxis+(0.03 \text{ to } 0.15) \times CD68-(0.04 \text{ to } 0.25) \times GSTM1-(0.05 \text{ to } 0.22) \times BAG1$$

wherein
(i) GRB7 axis=(0.45 to 1.35)×GRB7+(0.05 to 0.15)× HER2;
(ii) if GRB7 axis<−2, then GRB7 axis thresh=−2, and if GRB7 axis≥−2, then GRB7 axis thresh=GRB7 axis;
(iii) ER axis=(Est1+PR+Bcl2+CEGP1)/4;
(iv) prolifaxis=(SURV+Ki.67+MYBL2+CCNB1+STK15)/5;
(v) if prolifaxis<−3.5, then prolifaxisthresh=−3.5; if prolifaxis≥−3.5, then prolifaxishresh=prolifaxis; and
(vi) invasionaxis=(CTSL2+STMY3)/2, wherein the individual contributions of the genes in (iii), (iv) and (vi) are weighted by a factor of 0.5 to 1.5, and wherein a higher RS represents an increased likelihood of breast cancer recurrence.

In another embodiment, RS is determined by using the following equation:

$$\begin{aligned}RS(\text{range, 0-100}) = &+0.47 \times HER2 \text{ Group Score} - \\ &0.34 \times ER \text{ Group Score} + \\ &1.04 \times \text{Proliferation Group Score} + \\ &0.10 \times \text{Invasion Group Score} + \\ &0.05 \times CD68 - \\ &0.08 \times GSTM1 - \\ &0.07 \times BAG1\end{aligned}$$

BRIEF DESCRIPTION OF THE DRAWINGS

FIG. 1 shows the relationship between recurrence score (RS) and likelihood of patient response to chemotherapy, based on results from a clinical trial with pathologic complete response endpoint.

Table 1 shows a list of genes, the expression of which correlates, positively or negatively, with breast cancer response to adriamycin and taxane neoadjuvant chemotherapy. Results from a clinical trial with pathologic complete response endpoint. Statistical analysis utilized univarite generalized linear models with a probit link function.

Table 2 presents a list of genes; the expression of which predicts breast cancer response to chemotherapy. Results from a retrospective clinical trial. The table includes accession numbers for the genes, sequences for the forward and reverse primers (designated by "f" and "r", respectively) and probes (designated by "p") used for PCR amplification.

Table 3 shows the amplicon sequences used in PCR amplification of the indicated genes.

DETAILED DESCRIPTION

A. Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "microarray" refers to an ordered arrangement of hybridizable array elements, preferably polynucleotide probes, on a substrate.

The term "polynucleotide," when used in singular or plural, generally refers to any polyribonucleotide or polydeoxyribonucleotide; which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The terms "differentially expressed gene," "differential gene expression" and their synonyms, which are used interchangeably, refer to a gene whose expression is activated to a higher or lower level in a subject suffering from a disease, specifically cancer, such as breast cancer, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between normal subjects and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about two-fold, preferably at least about four-fold, more preferably at least about six-fold, most preferably at least about ten-fold difference between the expression of a given gene in normal and diseased subjects, or in various stages of disease development in a diseased subject.

The term "normalized" with regard to a gene transcript or a gene expression product refers to the level of the transcript or gene expression product relative to the mean levels of transcripts/products of a set of reference genes, wherein the reference genes are either selected based on their minimal variation across, patients, tissues or treatments ("housekeeping genes"), or the reference genes are the totality of tested genes. In the latter case, which is commonly referred to as "global normalization", it is important that the total number of tested genes be relatively large, preferably greater than 50. Specifically, the term 'normalized' with respect to an RNA transcript refers to the transcript level relative to the mean of transcript levels of a set of reference genes. More specifically, the mean level of an RNA transcript as measured by TaqMan® RT-PCR refers to the Ct value minus the mean Ct values of a set of reference gene transcripts.

The terms "expression threshold," and "defined expression threshold" are used interchangeably and refer to the level of a gene or gene product in question above which the gene or gene product serves as a predictive marker for patient response or resistance to a drug. The threshold typically is defined experimentally from clinical studies. The expression threshold can be selected either for maximum sensitivity (for example, to detect all responders to a drug), or for maximum selectivity (for example to detect only responders to a drug), or for minimum error.

The phrase "gene amplification" refers to a process by which multiple copies of a gene or gene fragment are formed in a particular cell or cell line. The duplicated region (a stretch of amplified DNA) is often referred to as "amplicon." Often, the amount of the messenger RNA (mRNA) produced, i.e., the level of gene expression, also increases in the proportion to the number of copies made of the particular gene.

The term "prognosis" is used herein to refer to the prediction of the likelihood of cancer-attributable death or progression, including recurrence, metastatic spread, and drug resistance, of a neoplastic disease, such as breast cancer. The term "prediction" is used herein to refer to the likelihood that a patient will respond either favorably or unfavorably to a drug or set of drugs, and also the extent of those responses, or that a patient will survive, following surgical removal or the primary tumor and/or chemotherapy for a certain period of time without cancer recurrence. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as surgical intervention, chemotherapy with a given drug or drug combination, and/or radiation therapy, or whether long-term survival of the patient, following surgery and/or termination of chemotherapy or other treatment modalities is likely.

The term "long-term" survival is used herein to refer to survival for at least 3 years, more preferably for at least 8 years, most preferably for at least 10 years following surgery or other treatment.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Patient response" can be assessed using any endpoint indicating a benefit to the patient, including, without limitation, (1) inhibition, to some extent, of tumor growth, including slowing down and complete growth arrest; (2) reduction in the number of tumor cells; (3) reduction in tumor size; (4) inhibition (i.e., reduction, slowing down or complete stopping) of tumor cell infiltration into adjacent peripheral organs and/or tissues; (5) inhibition (i.e. reduction, slowing down or complete stopping) of metastasis; (6) enhancement of anti-tumor immune response, which may, but, does not have to, result in the regression or rejection of the tumor; (7) relief, to some extent, of one or more symptoms associated with the tumor; (8) increase in the length of survival following treatment; and/or (9) decreased mortality at a given point of time following treatment.

"Neoadjuvant therapy" is adjunctive or adjuvant therapy given prior to the primary (main) therapy. Neoadjuvant therapy includes, for example, chemotherapy, radiation therapy, and hormone therapy. Thus, chemotherapy may be administered prior to surgery to shrink the tumor, so that surgery can be more effective, or, in the case of previously unoperable tumors, possible.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/

0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm. DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

In the context of the present invention, reference to "at least one," "at least two," "at least five," etc. of the genes listed in any particular gene set means any one or any and all combinations of the genes listed.

B. Detailed Description

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

1. Gene Expression Profiling

Methods of gene expression profiling include methods based on hybridization analysis of polynucleotides, methods based on sequencing of polynucleotides, and proteomics-based methods. The most commonly used methods known in the art for the quantification of mRNA expression in a sample include northern blotting and in situ hybridization (Parker & Barnes, *Methods in Molecular Biology* 106:247-283 (1999)); RNAse protection assays (Hod, *Biotechniques* 13:852-854 (1992)); and PCR-based methods, such as reverse transcription polymerase chain reaction (RT-PCR) (Weis et al., *Trends in Genetics* 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

2. PCR-based Gene Expression Profiling Methods
a. Reverse Transcriptase PCR (RT-PCR)

One of the most sensitive and most flexible quantitative PCR-based gene expression profiling methods is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of mRNA from a target sample. The starting material is typically total RNA isolated from human tumors or tumor cell lines; and corresponding normal tissues or cell lines, respectively. Thus RNA can be isolated from a variety of primary tumors, including breast, lung, colon, prostate, brain, liver, kidney, pancreas, spleen, thymus, testis, ovary, uterus, etc., tumor, or tumor cell lines, with pooled DNA from healthy donors. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest.* 56:A67 (1987), and De Andrés et al., *BioTechniques* 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo-blastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, CA, USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, Taq-Man® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize errors, and the effect of sample-to-sample variation, RT-PCR is usually performed using a reference RNA which ideally is expressed at a constant level among different tissues, and is unaffected by the experimental treatment. RNAs most frequently used to normalize patterns of gene expression are mRNAs for the housekeeping gene's glyceraldehyde-3-phosphate-dehydrogenase (GAPD) and β-actin (ACTB).

A more recent variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., *Genome Research* 6:986-994 (1996).

b. MassARRAY System

In the MassARRAY-based gene expression profiling method, developed by Sequenom, Inc. (San Diego, Calif.) following the isolation of RNA and reverse transcription, the obtained cDNA is spiked with a synthetic DNA molecule (competitor), which matches the targeted cDNA region in all positions, except a single base, and serves as an internal standard. The cDNA/competitor mixture is PCR amplified and is subjected to a post-PCR shrimp alkaline phosphatase (SAP) enzyme treatment, which results in the dephosphorylation of the remaining nucleotides. After inactivation of the alkaline phosphatase, the PCR products from the competitor and cDNA are subjected to primer extension, which generates distinct mass signals for the competitor- and cDNA-derives PCR products. After purification, these products are dispensed on a chip array, which is pre-loaded with components needed for analysis with matrix-assisted laser desorption ionization time-of-flight mass spectrometry (MALDI-TOF MS) analysis. The cDNA present in the reaction is then quantified by analyzing the ratios of the peak areas in the mass spectrum generated. For further details see, e.g. Ding and Cantor, *Proc. Natl. Acad. Sci. USA* 100:3059-3064 (2003).

c. Other PCR-Based Methods

Further PCR-based techniques include, for example, differential display (Liang and Pardee, *Science* 257:967-971 (1992)); amplified fragment length polymorphism (iAFLP) (Kawamoto et al., *Genome Res.* 12:1305-1312 (1999)); BeadArray™ technology (Illumina, San Diego, Calif.; Oliphant et al., *Discovery of Markers for Disease* (Supplement to *Biotechniques*), June 2002; Ferguson et al., *Analytical Chemistry* 72:5618 (2000)); BeadsArray for Detection of Gene Expression (BADGE), using the commercially available Luminex[100] LabMAP system and multiple color-coded microspheres (Luminex Corp., Austin, Tex.) in a rapid assay for gene expression (Yang et al., *Genome Res.* 11:1888-1898 (2001)); and high coverage expression profiling (HiCEP) analysis (Fukumura et al., *Nucl. Acids. Res.* 31(16) e94 (2003)).

3. Microarrays

Differential gene expression can also be identified, or confirmed using the microarray technique. Thus, the expression profile of breast cancer-associated genes can be measured in either fresh or paraffin-embedded tumor tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately, two-fold differences in the expression levels (Schena et al., *Proc.*

*Natl. Acad. Sci. USA* 93(2):106-149 (1996)). Microarray analysis can be performed by commercially available equipment, following manufacturer's protocols, such as by using the Affymetrix GenChip technology, or Incyte's microarray technology.

The development of microarray methods for large-scale analysis of gene expression makes it possible to search systematically for molecular markers of cancer classification and outcome prediction in a variety of tumor types.

4. Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., *Science* 270:484-487 (1995); and Velculescu et al., *Cell* 88:243-51 (1997).

5. Gene Expression Analysis by Massively Parallel Signature Sequencing (MPSS)

This method, described by Brenner et al., *Nature Biotechnology* 18:630-634 (2000), is a sequencing approach that combines non-gel-based signature sequencing with in vitro cloning of millions of templates on separate 5 μm diameter microbeads. First, a microbead library of DNA templates is constructed by in vitro cloning. This is followed by the assembly of a planar array of the template-containing microbeads in a flow cell at a high density (typically greater than $3 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

6. Immunohistochemistry

Immunohistochemistry methods are also suitable for detecting the expression levels of the prognostic markers of the present invention. Thus, antibodies or antisera, preferably polyclonal antisera, and most preferably monoclonal antibodies specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

7. Proteomics

The term "proteome" is defined as the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. my mass spectrometry or N-terminal sequencing, and (3) analysis of the data using bioinformatics. Proteomics methods are valuable supplements to other methods of gene expression profiling, and can be used, alone or in combination with other methods, to detect the products of the prognostic markers of the present invention.

8. General Description of mRNA Isolation, Purification and Amplification

The steps of a representative protocol for profiling gene expression using fixed, paraffin-embedded tissues as the RNA source, including mRNA isolation, purification, primer extension and amplification are given in various published journal articles (for example: T. E. Godfrey et al. *J. Molec. Diagnostics* 2: 84-91 [2000]; K. Specht et al., *Am. J. Pathol.* 158: 419-29 [2001]). Briefly, a representative process starts with cutting about 10 μm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR. Finally, the data are analyzed to identify the best treatment option(s) available to the patient on the basis of the characteristic gene expression pattern identified in the tumor sample examined.

9. Cancer Chemotherapy

Chemotherapeutic agents used in cancer treatment can be divided into several groups, depending on their mechanism of action. Some chemotherapeutic agents directly damage DNA and RNA. By disrupting replication of the DNA such chemotherapeutics either completely halt replication, or result in the production of nonsense DNA or RNA. This category includes, for example, cisplatin (Platinol®), daunorubicin (Cerubidine®), doxorubicin (Adriamycin®), and etoposide (VePesid®). Another group of cancer chemotherapeutic agents interfere with the formation of nucleotides or deoxyribonucleotides, so that RNA synthesis and cell replication is blocked. Examples of drugs in this class include methotrexate (Abitrexate®), mercaptopurine (Purinethol®), fluorouracil (Adrucil®), and hydroxyurea (Hydrea®). A third class of chemotherapeutic agents effects the synthesis or breakdown of mitotic spindles, and, as a result, interrupt cell division. Examples of drugs in this class include Vinblastine (Velban®), Vincristine (Oncovin®) and taxenes, such as, Pacitaxel (Taxol®), and Tocetaxel (Taxotere®) Tocetaxel is currently approved in the United States to treat patients with locally advanced or metastatic breast cancer after failure of prior chemotherapy, and patients with locally advanced or metastatic non-small cell lung cancer after failure of prior platinum-based chemotherapy.

A common problem with chemotherapy is the high toxicity of chemotherapeutic agents, such as anthracyclines and taxenes, which limits the clinical benefits of this treatment approach.

Most patients receive chemotherapy immediately following surgical removal of tumor. This approach is commonly referred to as adjuvant therapy. However, chemotherapy can be administered also before surgery, as so called neoadjuvant treatment. Although the use of neo-adjuvant chemotherapy originates from the treatment of advanced and inoperable breast cancer, it has gained acceptance in the treatment of other types of cancers as well. The efficacy of neoadjuvant chemotherapy has been tested in several clinical trials. In the multi-center National Surgical Adjuvant Breast and Bowel Project B-18 (NSAB B-18) trial (Fisher et al., *J. Clin. Oncology* 15:2002-2004 (1997); Fisher et al., *J.*

Clin. Oncology 16:2672-2685 (1998)) neoadjuvant therapy was performed with a combination of adriamycin and cyclophosphamide ("AC regimen"). In another clinical trial, neoadjuvant therapy was administered using a combination of 5-fluorouracil, epirubicin and cyclophosphamide ("FEC regimen") (van Der Hage et al., *J. Clin. Oncol.* 19:4224-4237 (2001)). Newer clinical trials have also used taxane-containing neoadjuvant treatment regiments. See, e.g. Holmes et al., *J. Natl. Cancer Inst.* 83:1797-1805 (1991) and Moliterni et al., *Seminars in Oncology*, 24:S17-10-S-17-14 (1999). For further information about neoadjuvant chemotherapy for breast cancer see, Cleator et al., *Endocrine-Related Cancer* 9:183-195 (2002).

10. Cancer Gene Set, Assayed Gene Subsequences, and Clinical Application of Gene Expression Data An important aspect of the present invention is to use the measured expression of certain genes by breast cancer tissue to provide prognostic information. For this purpose it is necessary to correct for (normalize away) differences in the amount of RNA assayed, variability in the quality of, the RNA used, and other factors, such as machine and operator differences. Therefore, the assay typically measures and incorporates the use of reference RNAs, including those transcribed from well-known housekeeping genes, such as GAPD and ACTB. A precise method for normalizing gene expression data is given in "User Bulletin #2" for the ABI PRISM 7700 Sequence Detection System (Applied Biosystems; 1997). Alternatively, normalization can be based on the mean or median signal (Ct) of all of the assayed genes or a large subset thereof (global normalization approach). In the study described in the following Example, a so called central normalization strategy was used, which utilized a subset of the screened genes, selected based on lack of correlation with clinical outcome, for normalization.

11. Recurrence and Response to Therapy Scores and Their Applications

Copending application Ser. No. 60/486,302, filed on Jul. 10, 2003, describes an algorithm-based prognostic test for determining the likelihood of cancer recurrence and/or the likelihood that a patient responds well to a treatment modality. Features of the algorithm that distinguish it from other cancer prognostic methods include: 1) a unique set of test mRNAs (or the corresponding gene expression products) used to determine recurrence likelihood, 2) certain weights used to combine the expression data into a formula, and 3) thresholds used to divide patients into groups of different levels of risk, such as low, medium, and high risk groups. The algorithm yields a numerical recurrence score (RS) or, if patient response to treatment is assessed, response to therapy score (RTS).

The test requires a laboratory assay to measure the levels of the specified mRNAs or their expression products, but can utilize very small amounts of either fresh tissue, or frozen tissue or fixed, paraffin-embedded tumor biopsy specimens that have already been necessarily collected from patients and archived. Thus, the test can be noninvasive. It is also compatible with several different methods of tumor tissue harvest, for example, via core biopsy or fine needle aspiration.

According to the method, cancer recurrence score (RS) is determined by:

(a) subjecting a biological sample comprising cancer cells obtained from said subject to gene or protein expression profiling;

(b) quantifying the expression level of multiple individual genes [i.e., levels of mRNAs or proteins] so as to determine an expression value for each gene;

(c) creating subsets of the gene expression values, each subset comprising expression values for genes linked by a cancer-related biological function and/or by co-expression;

(d) multiplying the expression level of each gene within a subset by a coefficient reflecting its relative contribution to cancer recurrence or response to therapy within said subset and adding the products of multiplication to yield a term for said subset;

(e) multiplying the term of each subset by a factor reflecting its contribution to cancer recurrence or response to therapy; and (f) producing the sum of terms for each subset multiplied by said factor to produce a recurrence score (RS) or a response to therapy (RTS) score, wherein the contribution of each subset which does not show a linear correlation with cancer recurrence or response to therapy is included only above a predetermined threshold level, and wherein the subsets in which increased expression of the specified genes reduce risk of cancer recurrence are assigned a negative value, and the subsets in which expression of the specified genes increase risk of cancer recurrence are assigned a positive value.

In a particular embodiment, RS is determined by:

(a) determining the expression levels of GRB7, HER2, EstR1, PR, Bcl2, CEGP1, SURV, Ki.67, MYBL2, CCNB1, STK15, CTSL2, STMY3, CD68, GSTM1, and BAG1, or their expression products, in a biological sample containing tumor cells obtained from said subject; and (b) calculating the recurrence score (RS) by the following equation:

$$RS = (0.23 \text{ to } 0.70) \times GRB7axisthresh - (0.17 \text{ to } 0.51) \times ERaxis + (0.53 \text{ to } 1.56) \times prolifaxisthresh + (0.07 \text{ to } 0.21) \times invasionaxis + (0.03 \text{ to } 0.15) \times CD68 - (0.04 \text{ to } 0.25) \times GSTM1 - (0.05 \text{ to } 0.22) \times BAG1$$

wherein (i) GRB7 axis=(0.45 to 1.35)×GRB7+(0.05 to 0.15)×HER2;

(ii) if GRB7 axis<−2, then GRB7 axis thresh=−2; and
if GRB7 axis≥−2, then GRB7 axis thresh=GRB7 axis;

(iii) ER axis=(Est1+PR+Bcl2+CEGP1)/4;

(iv) prolifaxis=(SURV+Ki.67+MYBL2+CCNB1+STK15)/5;

(v) if prolifaxis<−3.5, then prolifaxisthresh=−3.5,
if prolifaxis≥−3.5, then prolifaxishresh=prolifaxis; and (vi) invasionaxis=(CTSL2+STMY3)/2, wherein the terms for all individual genes for which ranges are not specifically shown can vary between about 0.5 and 1.5, and wherein a higher RS represents an increased likelihood of cancer recurrence.

Further details of the invention will be described in the following non-limiting Example.

EXAMPLE

A Retrospective Study of Neoadjuvant Chemotherapy in Invasive Breast Cancer

Gene Expression Profiling of Paraffin-Embedded Core Biopsy Tissue

This was a collaborative study involving Genomic Health, Inc., (Redwood City Calif.), and Institute Tumori, Milan, Italy. The primary objective of the study was to explore the correlation between pre-treatment molecular profiles and pathologic complete response (pCR) to neoadjuvant chemotherapy in locally advanced breast cancer.

Patient Inclusion Criteria:

Histologic diagnosis of invasive breast cancer (date of surgery 1998-2002); diagnosis of locally advanced breast cancer defined by skin infiltration and-or N2 axillary status and or homolateral supraclavicular positive nodes; core biopsy, neoadjuvant chemotherapy and surgical resection performed at Istituto Nazionale Tumori, Milan; signed informed consent that the biological material obtained for histological diagnosis or diagnostic procedures would be used for research; and histopathologic assessment indicating adequate amounts of tumor tissue for inclusion in this research study.

Exclusion Criteria:

Distant metastases; no tumor block available from initial core biopsy or from the surgical resection; or no tumor or very little tumor (<5% of the overall tissue on the slide) in block as assessed by examination of the H&E slide by the Pathologist.

Study Design

Eighty-nine evaluable patients (from a set of 96 clinically evaluable patients) were identified and studied. The levels of 384 mRNA species were measured by RT-PCR, representing products of candidate cancer-related genes that were selected from the biomedical research literature. Only one gene was lost due to inadequate signal.

Patient characteristics were as follows: Mean age: 50 years; Tumor grades: 24% Well, 55% Moderate, and 21% Poor; Sixty-three % of patients were ER positive {by immunohistochemistry}; Seventy % of patients had positive lymph nodes.

All patients were given primary neoadjuvant chemotherapy: Doxorubicin plus Taxol 3 weeks/3 cycles followed by Taxol® (paclitaxel) 1 week/12 cycles. Surgical removal of the tumor followed completion of chemotherapy. Core tumor biopsy specimens were taken prior to start of chemotherapy, and served as the source of RNA for the RT-PCR assay.

Materials and Methods

Fixed paraffin-embedded (FPE) tumor tissue from biopsy was obtained prior to and after chemotherapy. Core biopsies were taken prior to chemotherapy. In that case, the pathologist selected the most representative primary tumor block, and submitted nine 10 micron sections for RNA analysis. Specifically, a total of 9 sections (10 microns in thickness each) were prepared and placed in three Costar Brand Microcentrifuge Tubes (Polypropylene, 1.7 mL tubes, clear; 3 sections in each tube) and pooled.

Messenger RNA was extracted using the MasterPure™ RNA Purification Kit (Epicentre Technologies) and quantified by the RiboGreen® fluorescence method (Molecular probes). Molecular assays of quantitative gene expression were performed by RT-PCR, using the ABI PRISM 7900™ Sequence Detection System™ (Perkin-Elmer-Applied Biosystems, Foster City, Calif., USA). ABI PRISM 7900™ consists of a thermocycler, laser, charge-coupled device (CCD), camera and computer. The system amplifies samples in a 384-well format on a thermocycler. During amplification, laser-induced fluorescent signal is collected in real-time for all 384 wells, and detected at the CCD. The system includes software for running the instrument and for analyzing the data.

Analysis and Results

Tumor tissue was analyzed for 384 genes. The threshold cycle ($C_T$) values for each patient were normalized based on the median of a subset of the screened genes for that particular patient, selected based on lack of correlation with clinical outcome (central normalization strategy). Patient beneficial response to chemotherapy was defined as pathologic complete response (pCR). Patients were formally assessed for response at the completion of all chemotherapy.

A clinical complete response (cCR) requires complete disappearance of, all clinically detectable disease, either by physical examination or diagnostic breast imaging.

A pathologic complete response (pCR) requires absence of residual breast cancer on histologic examination of biopsied breast tissue, lumpectomy or mastectomy specimens following primary chemotherapy. Residual ductal carcinoma in situ (DCIS) may be present. Residual cancer in regional nodes may not be present. Of the 89 evaluable patients 11 (12%) had a pathologic complete response (pCR). Seven of these patients were ER negative.

A partial clinical response was defined as a ≥50% decrease in tumor area (sum of the products of the longest perpendicular diameters) or a ≥50% decrease in the sum of the products of the longest perpendicular diameters of multiple lesions in the breast and axilla. No area of disease may increase by >25% and no new lesions may appear.

Analysis was performed by comparing the relationship between normalized gene expression and the binary outcomes of pCR or no pCR. Univariate generalized models were used with probit or logit link functions. See, e.g. Van K. Borooah, LOGIT and PROBIT, Ordered Multinominal Models, Sage University Paper, 2002.

Table 1 presents pathologic response correlations with gene expression, and lists the 86 genes for which the p-value for the differences between the groups was <0.1. The second column (with the heading "Direction") denotes whether increased expression correlates with decreasing or increasing likelihood of response to chemotherapy. The statistical significance of the predictive value for each gene is given by P-value (right hand column)

| Gene | Direction | Probit Link | | |
|---|---|---|---|---|
| | | Intercept | Slope | P-value |
| TBP | Decreasing | 0.0575 | 2.4354 | 0.0000 |
| ILT.2 | Increasing | 0.5273 | −0.9489 | 0.0003 |
| ABCC5 | Decreasing | 0.9872 | 0.8181 | 0.0003 |
| CD18 | Increasing | 3.4735 | −1.0787 | 0.0007 |
| GATA3 | Decreasing | 0.6175 | 0.2975 | 0.0008 |
| DICER1 | Decreasing | −0.9149 | 1.4875 | 0.0013 |
| MSH3 | Decreasing | 2.6875 | 0.9270 | 0.0013 |
| GBP1 | Increasing | 1.7649 | −0.5410 | 0.0014 |
| IRS1 | Decreasing | 1.3576 | 0.5214 | 0.0016 |
| CD3z | Increasing | 0.1567 | −0.5162 | 0.0018 |
| FasI | Increasing | −0.6351 | −0.4050 | 0.0019 |
| TUBB | Decreasing | 1.2745 | 0.8267 | 0.0025 |
| BAD | Decreasing | 0.9993 | 1.1325 | 0.0033 |
| ERCC1 | Decreasing | 0.0327 | 1.0784 | 0.0039 |
| MCM6 | Increasing | 0.1371 | −0.8008 | 0.0052 |
| PR | Decreasing | 1.6079 | 0.1764 | 0.0054 |
| APC | Decreasing | 0.7264 | 1.0972 | 0.0061 |
| GGPS1 | Decreasing | 1.0906 | 0.8124 | 0.0062 |
| KRT18 | Decreasing | −0.8029 | 0.4506 | 0.0063 |
| ESRRG | Decreasing | 2.0198 | 0.2262 | 0.0063 |
| E2F1 | Increasing | 0.2188 | −0.5277 | 0.0068 |
| AKT2 | Decreasing | −1.3566 | 1.1902 | 0.0074 |
| A.Catenin | Decreasing | −0.6859 | 0.9279 | 0.0079 |
| CEGP1 | Decreasing | 1.3355 | 0.1875 | 0.0091 |
| NPD009 | Decreasing | 1.3996 | 0.2971 | 0.0092 |
| MAPK14 | Decreasing | 2.6253 | 1.6007 | 0.0093 |
| RUNX1 | Decreasing | −0.4138 | 0.7214 | 0.0103 |
| ID2 | Increasing | 1.7326 | −0.7032 | 0.0104 |
| G.Catenin | Decreasing | −0.1221 | 0.5954 | 0.0110 |
| FBXO5 | Increasing | 0.3421 | −0.4935 | 0.0110 |
| FHIT | Decreasing | 1.9966 | 0.4989 | 0.0113 |
| MTA1 | Decreasing | 0.3127 | 0.6069 | 0.0133 |
| ERBB4 | Decreasing | 1.4591 | 0.1436 | 0.0135 |

-continued

| Gene | Direction | Probit Link | | |
|---|---|---|---|---|
| | | Intercept | Slope | P-value |
| FUS | Decreasing | −0.6150 | 0.9415 | 0.0137 |
| BBC3 | Decreasing | 2.4796 | 0.6495 | 0.0138 |
| IGF1R | Decreasing | 1.1998 | 0.3116 | 0.0147 |
| CD9 | Decreasing | −0.9292 | 0.5747 | 0.0156 |
| TP53BP1 | Decreasing | 1.4325 | 0.8122 | 0.0169 |
| MUC1 | Decreasing | 0.8881 | 0.2140 | 0.0175 |
| IGFBP5 | Decreasing | −0.6180 | 0.4880 | 0.0181 |
| rhoC | Decreasing | −0.1726 | 0.6860 | 0.0184 |
| RALBP1 | Decreasing | 0.2383 | 0.9509 | 0.0185 |
| CDC20 | Increasing | 1.3204 | −0.4390 | 0.0186 |
| STAT3 | Decreasing | −0.9763 | 0.7023 | 0.0194 |
| ERK1 | Decreasing | 0.8577 | 0.6496 | 0.0198 |
| HLA.DPB1 | Increasing | 3.6300 | −0.6035 | 0.0202 |
| SGCB | Decreasing | 0.6171 | 0.7823 | 0.0208 |
| CGA | Increasing | 0.0168 | −0.1450 | 0.0209 |
| DHPS | Decreasing | 0.2957 | 0.7840 | 0.0216 |
| MGMT | Decreasing | 0.9238 | 0.6876 | 0.0226 |
| CRIP2 | Decreasing | 0.5524 | 0.4394 | 0.0230 |
| MMP12 | Increasing | 0.4208 | −0.2419 | 0.0231 |
| ErbB3 | Decreasing | 0.9438 | 0.2798 | 0.0233 |
| RAP1GDS1 | Decreasing | 0.2617 | 0.7672 | 0.0235 |
| CDC25B | Increasing | 1.6965 | −0.5356 | 0.0264 |
| IL6 | Increasing | 0.0592 | −0.2388 | 0.0272 |
| CCND1 | Decreasing | 0.2260 | 0.2992 | 0.0272 |
| CYBA | Increasing | 2.6493 | −0.5175 | 0.0287 |
| PRKCD | Decreasing | 0.2125 | 0.6745 | 0.0291 |
| DR4 | Increasing | 0.3039 | −0.5321 | 0.0316 |
| Hepsin | Decreasing | 1.9211 | 0.1873 | 0.0318 |
| CRABP1 | increasing | 1.0309 | −0.1287 | 0.0320 |
| AK055699 | Decreasing | 2.0442 | 0.1765 | 0.0343 |
| Contig.51037 | Increasing | 0.7857 | −0.1131 | 0.0346 |
| VCAM1 | Increasing | 1.1866 | −0.3560 | 0.0346 |
| FYN | Increasing | 1.5502 | −0.5624 | 0.0359 |
| GRB7 | Increasing | 1.3592 | −0.1646 | 0.0375 |
| AKAP.2 | Increasing | 1.7946 | −0.7008 | 0.0382 |
| RASSF1 | Increasing | 1.1972 | −0.0390 | 0.0384 |
| MCP1 | Increasing | 1.3700 | −0.3805 | 0.0388 |
| ZNF38 | Decreasing | 1.7957 | 0.4993 | 0.0395 |
| MCM2 | Increasing | 1.0574 | −0.4695 | 0.0426 |
| GBP2 | Increasing | 1.4095 | −0.4559 | 0.0439 |
| SEMA3F | Decreasing | 1.2706 | 0.3725 | 0.0455 |
| CD31 | Increasing | 1.9913 | −0.5955 | 0.0459 |
| COL1A1 | Decreasing | −1.9861 | 0.3812 | 0.0466 |
| ER2 | Increasing | −0.5204 | −0.2617 | 0.0471 |
| BAG1 | Decreasing | 0.6731 | 0.5070 | 0.0472 |
| AKT1 | Decreasing | −0.4467 | 0.5768 | 0.0480 |
| COL1A2 | Decreasing | −1.0233 | 0.3804 | 0.0490 |
| STAT1 | Increasing | 1.9447 | −0.4062 | 0.0498 |
| Wnt.5a | Decreasing | 2.2244 | 0.2983 | 0.0518 |
| PTPD1 | Decreasing | 1.2950 | 0.4834 | 0.0552 |
| RAB6C | Decreasing | 0.4841 | 0.5635 | 0.0717 |
| TK1 | Increasing | 0.6127 | −0.3625 | 0.0886 |
| Bcl2 | Decreasing | 1.1459 | 0.2509 | 0.0959 |

Based on the data set forth in Table 1, increased expression of the following genes correlates with increased likelihood of complete pathologic response to treatment: ILT.2; CD18; GBP1; CD3z; fasl; MCM6; E2F1; ID2; FBXO5; CDC20; HLA.DPB1; CGA; MMP12; CDC25B; IL6; CYBA; DR4; CRABP1; Contig.51037; VCAM1; FYN; GRB7; AKAP.2; RASSF1; MCP1; MCM2; GBP2; CD31; ER2; STAT1; TK1; while increased expression of the following genes correlates with decreased likelihood of complete pathologic response to treatment: TBP; ABCC5; GATA3; DICER1; MSH3; IRS1; TUBB; BAD; ERCC1; PR; APC; GGPS1; KRT18; ESRRG; AKT2; A.Catenin; CEGP1; NPD009; MAPK14; RUNX1; G.Catenin; FHIT; MTA1; ErbB4; FUS; BBC3; IGF1R; CD9; TP53BP1; MUC1; IGFBP5; rhoC; RALBP1; STAT3; ERK1; SGCB; DHPS; MGMT; CRIP2; ErbB3; RAP1GDS1; CCND1; PRKCD; Hepsin; AK055699; ZNF38; SEMA3F; COL1A1; BAG1; AKT1; COL1A2; Wnt.5a; PTPD1; RAB6C; Bcl2.

The relationship between the recurrence risk algorithm (described in copending U.S. application Ser. No. 60/486, 302) and pCR was also investigated. The algorithm incorporates the measured levels of 21 mRNA species. Sixteen mRNAs (named below) were candidate clinical markers and the remaining 5 (ACTB, GAPD, GUSB, RPLPO, and TFRC) were reference genes. Reference-normalized expression measurements range from 0 to 15, where a one unit increase reflects a 2-fold increase in RNA.

The Recurrence Score (RS) is calculated from the quantitative expression of four sets of marker genes (an estrogen receptor group of 4 genes—ESR1, PGR, BCL2, and SCUBE2; a proliferation set of 5 genes—MK167, MYBL2, BIRC5, CCNB1, and STK6; a HER2 set of 2 genes—ERBB2 and GRB7, an invasion group of 2 genes—MMP11 and CTSL2) and 3 other individual genes—GSTM1, BAG1, and CD68.

Although the genes and the multiplication factors used in the equation may vary, in a typical embodiment, the following equation may be used to calculate RS:

$$RS(\text{range, } 0\text{-}100) = +0.47 \times HER2 \text{ Group Score} -$$
$$0.34 \times ER \text{ Group Score} +$$
$$1.04 \times \text{Proliferation Group Score} +$$
$$0.10 \times \text{Invasion Group Score} +$$
$$0.05 \times CD68 -$$
$$0.08 \times GSTM1 -$$
$$0.07 \times BAG1$$

Application of this algorithm to study clinical and gene expression data sets yields a continuous curve relating RS to pCR values, as shown in FIG. 1. Examination of these data shows that patients with RS>50 are in the upper 50 percentile of patients in terms of likelihood of response to chemotherapy, and that patients with RS<35 are in the lower 50 percentile of patients in terms of likelihood of response to chemotherapy.

All references cited throughout the disclosure are hereby expressly incorporated by reference.

While the invention has been described with emphasis upon certain specific embodiments, it is be apparent to those skilled in the art that variations and modification in the specific methods and techniques are possible. Accordingly, this invention includes all modifications encompassed within the spirit and scope of the invention as defined by the following claims.

TABLE 2

| A-Catenin | NM_001903 | S2138/A-Cate.f2 | CGTTCCGATCCTCTATACTGCAT | 23 | SEQ ID NO: 1 |
| A-Catenin | NM_001903 | S2139/A-Cate.r2 | AGGTCCCTGTTGGCCTTATAGG | 22 | SEQ ID NO: 2 |
| A-Catenin | NM_001903 | S4725/A-Cate.p2 | ATGCCTACAGCACCCTGATGTCGCA | 25 | SEQ ID NO: 3 |

TABLE 2-continued

| ABCC5 | NM_005688 | S5605/ABCC5.f1 | TGCAGACTGTACCATGCTGA | 20 | SEQ ID NO: 4 |
|---|---|---|---|---|---|
| ABCC5 | NM_005688 | S5606/ABCC5.r1 | GGCCAGCACCATAATCCTAT | 20 | SEQ ID NO: 5 |
| ABCC5 | NM_005688 | S5607/ABCC5.p1 | CTGCACACGGTTCTAGGCTCCG | 22 | SEQ ID NO: 6 |
| AK055699 | AK055699 | S2097/AK0556.f1 | CTGCATGTGATTGAATAAGAAACAAGA | 27 | SEQ ID NO: 7 |
| AK055699 | AK055699 | S2098/AK0556.r1 | TGTGGACCTGATCCCTGTACAC | 22 | SEQ ID NO: 8 |
| AK055699 | AK055699 | S5057/AK0556.p1 | TGACCACACCAAAGCCTCCCTGG | 23 | SEQ ID NO: 9 |
| AKAP-2 | NM_007203 | S1374/AKAP-2.f1 | ACGAATTGTCGGTGAGGTCT | 20 | SEQ ID NO: 10 |
| AKAP-2 | NM_007203 | S1375/AKAP-2.r1 | GTCCATGCTGAAATCATTGG | 20 | SEQ ID NO: 11 |
| AKAP-2 | NM_007203 | S4934/AKAP-2.p1 | CAGGATACCACAGTCCTGGAGACCC | 25 | SEQ ID NO: 12 |
| AKT1 | NM_005163 | S0010/AKT1.f3 | CGCTTCTATGGCGCTGAGAT | 20 | SEQ ID NO: 13 |
| AKT1 | NM_005163 | S0012/AKT1.r3 | TCCCGGTACACCACGTTCTT | 20 | SEQ ID NO: 14 |
| AKT1 | NM_005163 | S4776/AKT1.p3 | CAGCCCTGGACTACCTGCACTCGG | 24 | SEQ ID NO: 15 |
| AKT2 | NM_001626 | S0828/AKT2.f3 | TCCTGCCACCCTTCAAACC | 19 | SEQ ID NO: 16 |
| AKT2 | NM_001626 | S0829/AKT2.r3 | GGCGGTAAATTCATCATCGAA | 21 | SEQ ID NO: 17 |
| AKT2 | NM_001626 | S4727/AKT2.p3 | CAGGTCACGTCCGAGGTCGACACA | 24 | SEQ ID NO: 18 |
| APC | NM_000038 | S0022/APC.f4 | GGACAGCAGGAATGTGTTTC | 20 | SEQ ID NO: 19 |
| APC | NM_000038 | S0024/APC.r4 | ACCCACTCGATTTGTTTCTG | 20 | SEQ ID NO: 20 |
| APC | NM_000038 | S4888/APC.p4 | CATTGGCTCCCCGTGACCTGTA | 22 | SEQ ID NO: 21 |
| BAD | NM_032989 | S2011/BAD.f1 | GGGTCAGGTGCCTCGAGAT | 19 | SEQ ID NO: 22 |
| BAD | NM_032989 | S2012/BAD.r1 | CTGCTCACTCGGCTCAAACTC | 21 | SEQ ID NO: 23 |
| BAD | NM_032989 | S5058/BAD.p1 | TGGGCCCAGAGCATGTTCCAGATC | 24 | SEQ ID NO: 24 |
| BAG1 | NM_004323 | S1386/BAG1.f2 | CGTTGTCAGCACTTGGAATACAA | 23 | SEQ ID NO: 25 |
| BAG1 | NM_004323 | S1387/BAG1.r2 | GTTCAACCTCTTCCTGTGGACTGT | 24 | SEQ ID NO: 26 |
| BAG1 | NM_004323 | S4731/BAG1.p2 | CCCAATTAACATGACCCGGCAACCAT | 26 | SEQ ID NO: 27 |
| BBC3 | NM_014417 | S1584/BBC3.f2 | CCTGGAGGGTCCTGTACAAT | 20 | SEQ ID NO: 28 |
| BBC3 | NM_014417 | S1585/BBC3.r2 | CTAATTGGGCTCCATCTCG | 19 | SEQ ID NO: 29 |
| BBC3 | NM_014417 | S4890/BBC3.p2 | CATCATGGGACTCCTGCCCTTACC | 24 | SEQ ID NO: 30 |
| Bcl2 | NM_000633 | S0043/Bcl2.f2 | CAGATGGACCTAGTACCCACTGAGA | 25 | SEQ ID NO: 31 |
| Bcl2 | NM_000633 | S0045/Bcl2.r2 | CCTATGATTTAAGGGCATTTTTCC | 24 | SEQ ID NO: 32 |
| Bcl2 | NM_000633 | S4732/Bcl2.p2 | TTCCACGCCGAAGGACAGCGAT | 22 | SEQ ID NO: 33 |
| CCND1 | NM_001758 | S0058/CCND1.f3 | GCATGTTCGTGGCCTCTAAGA | 21 | SEQ ID NO: 34 |
| CCND1 | NM_001758 | S0060/CCND1.r3 | CGGTGTAGATGCACAGCTTCTC | 22 | SEQ ID NO: 35 |
| CCND1 | NM_001758 | S4986/CCND1.p3 | AAGGAGACCATCCCCCTGACGGC | 23 | SEQ ID NO: 36 |
| CD18 | NM_000211 | S0061/CD18.f2 | CGTCAGGACCCACCATGTCT | 20 | SEQ ID NO: 37 |
| CD18 | NM_000211 | S0063/CD18.r2 | GGTTAATTGGTGACATCCTCAAGA | 24 | SEQ ID NO: 38 |
| CD18 | NM_000211 | S4987/CD18.p2 | CGCGGCCGAGACATGGCTTG | 20 | SEQ ID NO: 39 |
| CD31 | NM_000442 | S1407/CD31.f3 | TGTATTTCAAGACCTCTGTGCACTT | 25 | SEQ ID NO: 40 |
| CD31 | NM_000442 | S1408/CD31.r3 | TTAGCCTGAGGAATTGCTGTGTT | 23 | SEQ ID NO: 41 |
| CD31 | NM_000442 | S4939/CD31.p3 | TTTATGAACCTGCCCTGCTCCCACA | 25 | SEQ ID NO: 42 |
| CD3z | NM_000734 | S0064/CD3z.f1 | AGATGAAGTGGAAGGCGCTT | 20 | SEQ ID NO: 43 |

TABLE 2-continued

| | | | | | |
|---|---|---|---|---|---|
| CD3z | NM_000734 | S0066/CD3z.r1 | TGCCTCTGTAATCGGCAACTG | 21 | SEQ ID NO: 44 |
| CD3z | NM_000734 | S4988/CD3z.p1 | CACCGCGGCCATCCTGCA | 18 | SEQ ID NO: 45 |
| CD9 | NM_001769 | S0686/CD9.f1 | GGGCGTGGAACAGTTTATCT | 20 | SEQ ID NO: 46 |
| CD9 | NM_001769 | S0687/CD9.r1 | CACGGTGAAGGTTTCGAGT | 19 | SEQ ID NO: 47 |
| CD9 | NM_001769 | S4792/CD9.p1 | AGACATCTGCCCCAAGAAGGACGT | 24 | SEQ ID NO: 48 |
| CDC20 | NM_001255 | S4447/CDC20.f1 | TGGATTGGAGTTCTGGGAATG | 21 | SEQ ID NO: 49 |
| CDC20 | NM_001255 | S4448/CDC20.r1 | GCTTGCACTCCACAGGTACACA | 22 | SEQ ID NO: 50 |
| CDC20 | NM_001255 | S4449/CDC20.p1 | ACTGGCCGTGGCACTGGACAACA | 23 | SEQ ID NO: 51 |
| CDC25B | NM_021874 | S1160/CDC25B.f1 | AAACGAGCAGTTTGCCATCAG | 21 | SEQ ID NO: 52 |
| CDC25B | NM_021874 | S1161/CDC258.r1 | GTTGGTGATGTTCCGAAGCA | 20 | SEQ ID NO: 53 |
| CDC25B | NM_021874 | S4842/CDC25B.p1 | CCTCACCGGCATAGACTGGAAGCG | 24 | SEQ ID NO: 54 |
| CEGP1 | NM_020974 | S1494/CEGP1.f2 | TGACAATCAGCACACCTGCAT | 21 | SEQ ID NO: 55 |
| CEGP1 | NM_020974 | S1495/CEGP1.r2 | TGTGACTACAGCCGTGATCCTTA | 23 | SEQ ID NO: 56 |
| CEGP1 | NM_020974 | S4735/CEGP1.p2 | CAGGCCCTCTTCCGAGCGGT | 20 | SEQ ID NO: 57 |
| CGA (CHGA | NM_001275 | S3221/CGA (C.f3 | CTGAAGGAGCTCCAAGACCT | 20 | SEQ ID NO: 58 |
| CGA (CHGA | NM_001275 | S3222/CGA (C.r3 | CAAAACCGCTGTGTTTCTTC | 20 | SEQ ID NO: 59 |
| CGA (CHGA | NM_001275 | S3254/CGA (C.p3 | TGCTGATGTGCCCTCTCCTTGG | 22 | SEQ ID NO: 60 |
| COL1A1 | NM_000088 | S4531/COL1A1.f1 | GTGGCCATCCAGCTGACC | 18 | SEQ ID NO: 61 |
| COL1A1 | NM_000088 | S4532/COL1A1.r1 | CAGTGGTAGGTGATGTTCTGGGA | 23 | SEQ ID NO: 62 |
| COL1A1 | NM_000088 | S4533/COL1A1.p1 | TCCTGCGCCTGATGTCCACCG | 21 | SEQ ID NO: 63 |
| COL1A2 | NM_000089 | S4534/COL1A2.f1 | CAGCCAAGAACTGGTATAGGAGCT | 24 | SEQ ID NO: 64 |
| COL1A2 | NM_000089 | S4535/COL1A2.r1 | AAACTGGCTGCCAGCATTG | 19 | SEQ ID NO: 65 |
| COL1A2 | NM_000089 | S4536/COL1A2.p1 | TCTCCTAGCCAGACGTGTTTCTTGTCCTTG | 30 | SEQ ID NO: 66 |
| Contig 5103: | XM_058945 | S2070/Contig.f1 | CGACAGTTGCGATGAAAGTTCTAA | 24 | SEQ ID NO: 67 |
| Contig 5103: | XM_058945 | S2071/Contig.r1 | GGCTGCTAGAGACCATGGACAT | 22 | SEQ ID NO: 68 |
| Contig 5103: | XM_058945 | S5059/Contig.p1 | CCTCCTCCTGTTGCTGCCACTAATGCT | 27 | SEQ ID NO: 69 |
| CRABP1 | NM_004378 | S5441/CRABP1.f3 | AACTTCAAGGTCGGAGAAGG | 20 | SEQ ID NO: 70 |
| CRABP1 | NM_004378 | S5442/CRABP1.r3 | TGGCTAAACTCCTGCACTTG | 20 | SEQ ID NO: 71 |
| CRABP1 | NM_004378 | S5443/CRABP1.p3 | CCGTCCACGGTCTCCTCCTCA | 21 | SEQ ID NO: 72 |
| CRIP2 | NM_001312 | S5676/CRIP2.f3 | GTGCTACGCCACCCTGTT | 18 | SEQ ID NO: 73 |
| CRIP2 | NM_001312 | S5677/CRIP2.r3 | CAGGGGCTTCTCGTAGATGT | 20 | SEQ ID NO: 74 |
| CRIP2 | NM_001312 | S5678/CRIP2.p3 | CCGATGTTCACGCCTTTGGGTC | 22 | SEQ ID NO: 75 |
| CYBA | NM_000101 | S5300/CYBA.f1 | GGTGCCTACTCCATTGTGG | 19 | SEQ ID NO: 76 |
| CYBA | NM_000101 | S5301/CYBA.r1 | GTGGAGCCCTTCTTCCTCTT | 20 | SEQ ID NO: 77 |
| CYBA | NM_000101 | S5302/CYBA.p1 | TACTCCAGCAGGCACACAAACACG | 24 | SEQ ID NO: 78 |
| DHPS | NM_013407 | S4519/DHPS.f3 | GGGAGAACGGGATCAATAGGAT | 22 | SEQ ID NO: 79 |
| DHPS | NM_013407 | S4520/DHPS.r3 | GCATCAGCCAGTCCTCAAACT | 21 | SEQ ID NO: 80 |
| DHPS | NM_013407 | S4521/DHPS.p3 | CTCATTGGGCACCAGCAGGTTCC | 24 | SEQ ID NO: 81 |
| DICER1 | NM_177438 | S5294/DICER1.f2 | TCCAATTCCAGCATCACTGT | 20 | SEQ ID NO: 82 |
| DICER1 | NM_177438 | S5295/DICER1.r2 | GGCAGTGAAGGCGATAAAGT | 20 | SEQ ID NO: 83 |

TABLE 2-continued

| Gene | Accession | ID | Sequence | Length | SEQ ID NO |
|---|---|---|---|---|---|
| DICER1 | NM_177438 | S5296/DICER1.p2 | AGAAAAGCTGTTTGTCTCCCCAGCA | 25 | SEQ ID NO: 84 |
| DR4 | NM_003844 | S2532/DR4.f2 | TGCACAGAGGGTGTGGGTTAC | 21 | SEQ ID NO: 85 |
| DR4 | NM_003844 | S2533/DR4.r2 | TCTTCATCTGATTTACAAGCTGTACATG | 28 | SEQ ID NO: 86 |
| DR4 | NM_003844 | S4981/DR4.p2 | CAATGCTTCCAACAATTTGTTTGCTTGCC | 29 | SEQ ID NO: 87 |
| E2F1 | NM_005225 | S3063/E2F1.f3 | ACTCCCTCTACCCTTGAGCA | 20 | SEQ ID NO: 88 |
| E2F1 | NM_005225 | S3064/E2F1.r3 | CAGGCCTCAGTTCCTTCAGT | 20 | SEQ ID NO: 89 |
| E2F1 | NM_005225 | S4821/E2F1.p3 | CAGAAGAACAGCTCAGGGACCCCT | 24 | SEQ ID NO: 90 |
| ER2 | NM_001437 | S0109/ER2.f2 | TGGTCCATCGCCAGTTATCA | 20 | SEQ ID NO: 91 |
| ER2 | NM_001437 | S0111/ER2.r2 | TGTTCTAGCGATCTTGCTTCACA | 23 | SEQ ID NO: 92 |
| ER2 | NM_001437 | S5001/ER2.p2 | ATCTGTATGCGGAACCTCAAAAGAGTCCCT | 30 | SEQ ID NO: 93 |
| ErbB3 | NM_001982 | S0112/ErbB3.f1 | CGGTTATGTCATGCCAGATACAC | 23 | SEQ ID NO: 94 |
| ErbB3 | NM_001982 | S0114/ErbB3.r1 | GAACTGAGACCCACTGAAGAAAGG | 24 | SEQ ID NO: 95 |
| ErbB3 | NM_001982 | S5002/ErbB3.p1 | CCTCAAAGGTACTCCCTCCTCCCGG | 25 | SEQ ID NO: 96 |
| ERBB4 | NM_005235 | S1231/ERBB4.f3 | TGGCTCTTAATCAGTTTCGTTACCT | 25 | SEQ ID NO: 97 |
| ERBB4 | NM_005235 | S1232/ERBB4.r3 | CAAGGCATATCGATCCTCATAAAGT | 25 | SEQ ID NO: 98 |
| ERBB4 | NM_005235 | S4891/ERBB4.p3 | TGTCCCACGAATAATGCGTAAATTCTCCAG | 30 | SEQ ID NO: 99 |
| ERCC1 | NM_001983 | S2437/ERCC1.f2 | GTCCAGGTGGATGTGAAAGA | 20 | SEQ ID NO: 100 |
| ERCC1 | NM_001983 | S2438/ERCC1.r2 | CGGCCAGGATACACATCTTA | 20 | SEQ ID NO: 101 |
| ERCC1 | NM_001983 | S4920/ERCC1.p2 | CAGCAGGCCCTCAAGGAGCTG | 21 | SEQ ID NO: 102 |
| ERK1 | Z11696 | S1560/ERK1.f3 | ACGGATCACAGTGGAGGAAG | 20 | SEQ ID NO: 103 |
| ERK1 | Z11696 | S1561/ERK1.r3 | CTCATCCGTCGGGTCATAGT | 20 | SEQ ID NO: 104 |
| ERK1 | Z11696 | S4882/ERK1.p3 | CGCTGGCTCACCCCTACCTG | 20 | SEQ ID NO: 105 |
| ESRRG | NM_001438 | S6130/ESRRG.f3 | CCAGCACCATTGTTGAAGAT | 20 | SEQ ID NO: 106 |
| ESRRG | NM_001438 | S6131/ESRRG.r3 | AGTCTCTTGGGCATCGAGTT | 20 | SEQ ID NO: 107 |
| ESRRG | NM_001438 | S6132/ESRRG.p3 | CCCCAGACCAAGTGTGAATACATGCT | 26 | SEQ ID NO: 108 |
| fasl | NM_000639 | S0121/fasl.f2 | GCACTTTGGGATTCTTTCCATTAT | 24 | SEQ ID NO: 109 |
| fasl | NM_000639 | S0123/fasl.r2 | GCATGTAAGAAGACCCTCACTGAA | 24 | SEQ ID NO: 110 |
| fasl | NM_000639 | S5004/fasl.p2 | ACAACATTCTCGGTGCCTGTAACAAAGAA | 29 | SEQ ID NO: 111 |
| FBXO5 | NM_012177 | S2017/FBXO5.r1 | GGATTGTAGACTGTCACCGAAATTC | 25 | SEQ ID NO: 112 |
| FBXO5 | NM_012177 | S2018/FBXO5.f1 | GGCTATTCTCATTTTCTCTACAAAGTG | 28 | SEQ ID NO: 113 |
| FBXO5 | NM_012177 | S5061/FBXO5.p1 | CCTCCAGGAGGCTACCTTCTTCATGTTCAC | 30 | SEQ ID NO: 114 |
| FHIT | NM_002012 | S2443/FHIT.f1 | CCAGTGGAGCGCTTCCAT | 18 | SEQ ID NO: 115 |
| FHIT | NM_002012 | S2444/FHIT.r1 | CTCTCTGGGTCGTCTGAAACAA | 22 | SEQ ID NO: 116 |
| FRIT | NM_002012 | S4921/FHIT.p1 | TCGGCCACTTCATCAGGACGCAG | 23 | SEQ ID NO: 117 |
| FUS | NM_004960 | S2936/FUS.f1 | GGATAATTCAGACAACAACACCATCT | 26 | SEQ ID NO: 118 |
| FUS | NM_004960 | S2937/FUS.r1 | TGAAGTAATCAGCCACAGACTCAAT | 25 | SEQ ID NO: 119 |
| FUS | NM_004960 | S4801/FUS.p1 | TCAATTGTAACATTCTCACCCAGGCCTTG | 29 | SEQ ID NO: 120 |
| FYN | NM_002037 | S5695/FYN.f3 | GAAGCGCAGATCATGAAGAA | 20 | SEQ ID NO: 121 |
| FYN | NM_002037 | S5696/FYN.r3 | CTCCTCAGACACCACTGCAT | 20 | SEQ ID NO: 122 |
| FYN | NM_002037 | S5697/FYN.p3 | CTGAAGCACGACAAGCTGGTCCAG | 24 | SEQ ID NO: 123 |

TABLE 2-continued

| | | | | | |
|---|---|---|---|---|---|
| G-Catenin | NM_002230 | S2153/G-Cate.f1 | TCAGCAGCAAGGGCATCAT | 19 | SEQ ID NO: 124 |
| G-Catenin | NM_002230 | S2154/G-Cate.r1 | GGTGGTTTTCTTGAGCGTGTACT | 23 | SEQ ID NO: 125 |
| G-Catenin | NM_002230 | S5044/G-Cate.p1 | CGCCCGCAGGCCTCATCCT | 19 | SEQ ID NO: 126 |
| GATA3 | NM_002051 | S0127/GATA3.f3 | CAAAGGAGCTCACTGTGGTGTCT | 23 | SEQ ID NO: 127 |
| GATA3 | NM_002051 | S0129/GATA3.r3 | GAGTCAGAATGGCTTATTCACAGATG | 26 | SEQ ID NO: 128 |
| GATA3 | NM_002051 | S5005/GATA3.p3 | TGTTCCAACCACTGAATCTGGACC | 24 | SEQ ID NO: 129 |
| GBP1 | NM_002053 | S5698/GBP1.f1 | TTGGGAAATATTTGGGCATT | 20 | SEQ ID NO: 130 |
| GBP1 | NM_002053 | S5699/GBP1.r1 | AGAAGCTAGGGTGGTTGTCC | 20 | SEQ ID NO: 131 |
| GBP1 | NM_002053 | S5700/GBP1.p1 | TTGGGACATTGTAGACTTGGCCAGAC | 26 | SEQ ID NO: 132 |
| GBP2 | NM_004120 | S5707/GBP2.f2 | GCATGGGAACCATCAACCA | 19 | SEQ ID NO: 133 |
| GBP2 | NM_004120 | S5708/GBP2.r2 | TGAGGAGTTTGCCTTGATTCG | 21 | SEQ ID NO: 134 |
| GBP2 | NM_004120 | S5709/GBP2.p2 | CCATGGACCAACTTCACTATGTGACAGAGC | 30 | SEQ ID NO: 135 |
| GGPS1 | NM_004837 | S1590/GGPS1.f1 | CTCCGACGTGGCTTTCCA | 18 | SEQ ID NO: 136 |
| GGPS1 | NM_004837 | S1591/GGPS1.r1 | CGTAATTGGCAGAATTGATGACA | 23 | SEQ ID NO: 137 |
| GGPS1 | NM_004837 | S4896/GGPS1.p1 | TGGCCCACAGCATCTATGGAATCCC | 25 | SEQ ID NO: 138 |
| GRB7 | NM_005310 | S0130/GRB7.f2 | CCATCTGCATCCATCTTGTT | 20 | SEQ ID NO: 139 |
| GRB7 | NM_005310 | S0132/GRB7.r2 | GGCCACCAGGGTATTATCTG | 20 | SEQ ID NO: 140 |
| GRB7 | NM_005310 | S4726/GRB7.p2 | CTCCCCACCCTTGAGAAGTGCCT | 23 | SEQ ID NO: 141 |
| Hepsin | NM_002151 | S2269/Hepsin.f1 | AGGCTGCTGGAGGTCATCTC | 20 | SEQ ID NO: 142 |
| Hepsin | NM_002151 | S2270/Hepsin.r1 | CTTCCTGCGGCCACAGTCT | 19 | SEQ ID NO: 143 |
| Hepsin | NM_002151 | S2271/Hepsin.p1 | CCAGAGGCCGTTTCTTGGCCG | 21 | SEQ ID NO: 144 |
| HLA-DPB1 | NM_002121 | S4573/HLA-DP.f1 | TCCATGATGGTTCTGCAGGTT | 21 | SEQ ID NO: 145 |
| HLA-DPB1 | NM_002121 | S4574/HLA-DP.r1 | TGAGCAGCACCATCAGTAACG | 21 | SEQ ID NO: 146 |
| HLA-DPB1 | NM_002121 | S4575/HLA-DP.p1 | CCCCGGACAGTGGCTCTGACG | 21 | SEQ ID NO: 147 |
| ID2 | NM_002166 | S0151/ID2.f4 | AACGACTGCTACTCCAAGCTCAA | 23 | SEQ ID NO: 148 |
| ID2 | NM_002166 | S0153/ID2.r4 | GGATTTCCATCTTGCTCACCTT | 22 | SEQ ID NO: 149 |
| ID2 | NM_002166 | S5009/ID2.p4 | TGCCCAGCATCCCCCAGAACAA | 22 | SEQ ID NO: 150 |
| IGF1R | NM_000875 | S1249/IGF1R.f3 | GCATGGTAGCCGAAGATTTCA | 21 | SEQ ID NO: 151 |
| IGF1R | NM_000875 | S1250/IGF1R.r3 | TTTCCGGTAATAGTCTGTCTCATAGATATC | 30 | SEQ ID NO: 152 |
| IGF1R | NM_000875 | S4895/IGF1R.p3 | CGCGTCATACCAAAATCTCCGATTTTGA | 28 | SEQ ID NO: 153 |
| IL6 | NM_000600 | S0760/IL6.f3 | CCTGAACCTTCCAAAGATGG | 20 | SEQ ID NO: 154 |
| IL6 | NM_000600 | S0761/IL6.r3 | ACCAGGCAAGTCTCCTCATT | 20 | SEQ ID NO: 155 |
| IL6 | NM_000600 | S4800/IL6.p3 | CCAGATTGGAAGCATCCATCTTTTTCA | 27 | SEQ ID NO: 156 |
| ILT-2 | NM_006669 | S1611/ILT-2.f2 | AGCCATCACTCTCAGTGCAG | 20 | SEQ ID NO: 157 |
| ILT-2 | NM_006669 | S1612/ILT-2.r2 | ACTGCAGAGTCAGGGTCTCC | 20 | SEQ ID NO: 158 |
| ILT-2 | NM_006669 | S4904/ILT-2.p2 | CAGGTCCTATCGTGGCCCTGA | 22 | SEQ ID NO: 159 |
| IRS1 | NM_005544 | S1943/IRS1.f3 | CCACAGCTCACCTTCTGTCA | 20 | SEQ ID NO: 160 |
| IRS1 | NM_005544 | S1944/IRS1.r3 | CCTCAGTGCCAGTCTCTTCC | 20 | SEQ ID NO: 161 |
| IRS1 | NM_005544 | S5050/IRS1.p3 | TCCATCCCAGCTCCAGCCAG | 20 | SEQ ID NO: 162 |
| KRT18 | NM_000224 | S1710/KRT18.f2 | AGAGATCGAGGCTCTCAAGG | 20 | SEQ ID NO: 163 |

TABLE 2-continued

| | | | | | |
|---|---|---|---|---|---|
| KRT18 | NM_000224 | S1711/KRT18.r2 | GGCCTTTTACTTCCTCTTCG | 20 | SEQ ID NO: 164 |
| KRT18 | NM_000224 | S4762/KRT18.p2 | TGGTTCTTCTTCATGAAGAGCAGCTCC | 27 | SEQ ID NO: 165 |
| MAPK14 | NM_139012 | S5557/MAPK14.f2 | TGAGTGGAAAAGCCTGACCTATG | 23 | SEQ ID NO: 166 |
| MAPK14 | NM_139012 | S5558/MAPK14.r2 | GGACTCCATCTCTTCTTGGTCAA | 23 | SEQ ID NO: 167 |
| MAPK14 | NM_139012 | S5559/MAPK14.p2 | TGAAGTCATCAGCTTTGTGCCACCACC | 27 | SEQ ID NO: 168 |
| MCM2 | NM_004526 | S1602/MCM2.f2 | GACTTTTGCCCGCTACCTTTC | 21 | SEQ ID NO: 169 |
| MCM2 | NM_004526 | S1603/MCM2.r2 | GCCACTAACTGCTTCAGTATGAAGAG | 26 | SEQ ID NO: 170 |
| MCM2 | NM_004526 | S4900/MCM2.p2 | ACAGCTCATTGTTGTCACGCCGGA | 24 | SEQ ID NO: 171 |
| MCM6 | NM_005915 | S1704/MCM6.f3 | TGATGGTCCTATGTGTCACATTCA | 24 | SEQ ID NO: 172 |
| MCM6 | NM_005915 | S1705/MCM6.r3 | TGGGACAGGAAACACACCAA | 20 | SEQ ID NO: 173 |
| MCM6 | NM_005915 | S4919/MCM6.p3 | CAGGTTTCATACCAACACAGGCTTCAGCAC | 30 | SEQ ID NO: 174 |
| MCP1 | NM_002982 | S1955/MCP1.f1 | CGCTCAGCCAGATGCAATC | 19 | SEQ ID NO: 175 |
| MCP1 | NM_002982 | S1956/MCP1.r1 | GCACTGAGATCTTCCTATTGGTGAA | 25 | SEQ ID NO: 176 |
| MCP1 | NM_002982 | S5052/MCP1.p1 | TGCCCCAGTCACCTGCTGTTA | 21 | SEQ ID NO: 177 |
| MGMT | NM_002412 | S1922/MGMT.f1 | GTGAAATGAAACGCACCACA | 20 | SEQ ID NO: 178 |
| MGMT | NM_002412 | S1923/MGMT.r1 | GACCCTGCTCACAACCAGAC | 20 | SEQ ID Nb: 179 |
| MGMT | NM_002412 | S5045/MGMT.p1 | CAGCCCTTTGGGGAAGCTGG | 20 | SEQ ID NO: 180 |
| MMP12 | NM_002426 | S4381/MMP12.f2 | CCAACGCTTGCCAAATCCT | 19 | SEQ ID NO: 181 |
| MMP12 | NM_002426 | S4382/MMP12.r2 | ACGGTAGTGACAGCATCAAAACTC | 24 | SEQ ID NO: 182 |
| MMP12 | NM_002426 | S4383/MMP12.p2 | AACCAGCTCTCTGTGACCCCAATT | 24 | SEQ ID NO: 183 |
| MSH3 | NM_002439 | S5940/MSH3.f2 | TGATTACCATCATGGCTCAGA | 21 | SEQ ID NO: 184 |
| MSH3 | NM_002439 | S5941/MSH3.r2 | CTTGTGAAAATGCCATCCAC | 20 | SEQ ID NO: 185 |
| MSH3 | NM_002439 | S5942/MSH3.p2 | TCCCAATTGTCGCTTCTTCTGCAG | 24 | SEQ ID NO: 186 |
| MTA1 | NM_004689 | S2369/MTA1.f1 | CCGCCCTCACCTGAAGAGA | 19 | SEQ ID NO: 187 |
| MTA1 | NM_004689 | S2370/MTA1.r1 | GGAATAAGTTAGCCGCGCTTCT | 22 | SEQ ID NO: 188 |
| MTA1 | NM_004689 | S4855/MTA1.p1 | CCCAGTGTCCGCCAAGGAGCG | 21 | SEQ ID NO: 189 |
| MUC1 | NM_002456 | S0782/MUC1.f2 | GGCCAGGATCTGTGGTGGTA | 20 | SEQ ID NO: 190 |
| MUC1 | NM_002456 | S0783/MUC1.r2 | CTCCACGTCGTGGACATTGA | 20 | SEQ ID NO: 191 |
| MUC1 | NM_002456 | S4807/MUC1.p2 | CTCTGGCCTTCCGAGAAGGTACC | 23 | SEQ ID NO: 192 |
| NPD009 (AB | NM_020686 | S4474/NPD009.f3 | GGCTGTGGCTGAGGCTGTAG | 20 | SEQ ID NO: 193 |
| NPD009 (AB | NM_020686 | S4475/NPD009.r3 | GGAGCATTCGAGGTCAAATCA | 21 | SEQ ID NO: 194 |
| NPD009 (AB | NM_020686 | S4476/NPD009.p3 | TTCCCAGAGTGTCTCACCTCCAGCAGAG | 28 | SEQ ID NO: 195 |
| PR | NM_000926 | S1336/PR.f6 | GCATCAGGCTGTCATTATGG | 20 | SEQ ID NO: 196 |
| PR | NM_000926 | S1337/PR.r6 | AGTAGTTGTGCTGCCCTTCC | 20 | SEQ ID NO: 197 |
| PR | NM_000926 | S4743/PR.p6 | TGTCCTTACCTGTGGGAGCTGTAAGGTC | 28 | SEQ ID NO: 198 |
| PRKCD | NM_006254 | S1738/PRKCD.f2 | CTGACACTTGCCGCAGAGAA | 20 | SEQ ID NO: 199 |
| PRKCD | NM_006254 | S1739/PRKCD.r2 | AGGTGGTCCTTGGTCTGGAA | 20 | SEQ ID NO: 200 |
| PRKCD | NM_006254 | S4923/PRKCD.p2 | CCCTTTCTCACCCACCTCATCTGCAC | 26 | SEQ ID NO: 201 |
| PTPD1 | NM_007039 | S3069/PTPD1.f2 | CGCTTGCCTAACTCATACTTTCC | 23 | SEQ ID NO: 202 |
| PTPD1 | NM_007039 | S3070/PTPD1.r2 | CCATTCAGACTGCGCCACTT | 20 | SEQ ID NO: 203 |

TABLE 2-continued

| | | | | | |
|---|---|---|---|---|---|
| PTPD1 | NM_007039 | S4822/PTPD1.p2 | TCCACGCAGCGTGGCACTG | 19 | SEQ ID NO: 204 |
| RAB6C | NM_032144 | S5535/RAB6C.f1 | GCGACAGCTCCTCTAGTTCCA | 21 | SEQ ID NO: 205 |
| RAB6C | NM_032144 | S5537/RAB6C.p1 | TTCCCGAAGTCTCCGCCCG | 19 | SEQ ID NO: 206 |
| RAB6C | NM_032144 | S5538/RAB6C.r1 | GGAACACCAGCTTGAATTTCCT | 22 | SEQ ID NO: 207 |
| RALBP1 | NM_006788 | S5853/RALBP1.f1 | GGTGTCAGATATAAATGTGCAAATGC | 26 | SEQ ID NO: 208 |
| RALBP1 | NM_006788 | S5854/RALBP1.r1 | TTCGATATTGCCAGCAGCTATAAA | 24 | SEQ ID NO: 209 |
| RALBP1 | NM_006788 | S5855/RALBP1.p1 | TGCTGTCCTGTCGGTCTCAGTACGTTCA | 28 | SEQ ID NO: 210 |
| RAP1GDS1 | NM_021159 | S5306/RAP1GD.f2 | TGTGGATGCTGGATTGATTT | 20 | SEQ ID NO: 211 |
| RAP1GDS1 | NM_021159 | S5307/RAP1GD.r2 | AAGCAGCACTTCCTGGTCTT | 20 | SEQ ID NO: 212 |
| RAP1GDS1 | NM_021159 | S5308/RAP1GD.p2 | CCACTGGTGCAGCTGCTAAATAGCA | 25 | SEQ ID NO: 213 |
| RASSF1 | NM_007182 | S2393/RASSF1.f3 | AGTGGGAGACACCTGACCTT | 20 | SEQ ID NO: 214 |
| RASSF1 | NM_007182 | S2394/RASSF1.r3 | TGATCTGGGCATTGTACTCC | 20 | SEQ ID NO: 215 |
| RASSF1 | NM_007182 | S4909/RASSF1.p3 | TTGATCTTCTGCTCAATCTCAGCTTGAGA | 29 | SEQ ID NO: 216 |
| rhoC | NM_005167 | S2162/rhoC.f1 | CCCGTTCGGTCTGAGGAA | 18 | SEQ ID NO: 217 |
| rhoC | NM_005167 | S2163/rhoC.r1 | GAGCACTCAAGGTAGCCAAGG | 22 | SEQ ID NO: 218 |
| rhoC | NM_005167 | S5042/rhoC.p1 | TCCGGTTCGCCATGTCCCG | 19 | SEQ ID NO: 219 |
| RUNX1 | NM_001754 | S4588/RUNX1.f2 | AACAGAGACATTGCCAACCA | 20 | SEQ ID NO: 220 |
| RUNX1 | NM_001754 | S4589/RUNX1.r2 | GTGATTTGCCCAGGAAGTTT | 20 | SEQ ID NO: 221 |
| RUNX1 | NM_001754 | S4590/RUNX1.p2 | TTGGATCTGCTTGCTGTCCAAACC | 24 | SEQ ID NO: 222 |
| SEMA3F | NM_004186 | S2857/SEMA3F.f3 | CGCGAGCCCCTCATTATACA | 20 | SEQ ID NO: 223 |
| SEMA3F | NM_004186 | S2858/SEMA3F.r3 | CACTCGCCGTTGACATCCT | 19 | SEQ ID NO: 224 |
| SEMA3F | NM_004186 | S4972/SEMA3F.p3 | CTCCCCACAGCGCATCGAGGAA | 22 | SEQ ID NO: 225 |
| SGCB | NM_000232 | S5752/SGCB.f1 | CAGTGGAGACCAGTTGGGTAGTG | 23 | SEQ ID NO: 226 |
| SGCB | NM_000232 | S5753/SGCB.r1 | CCTTGAAGAGCGTCCCATCA | 20 | SEQ ID NO: 227 |
| SGCB | NM_000232 | S5754/SGCB.p1 | CACACATGCAGAGCTTGTAGCGTACCCA | 28 | SEQ ID NO: 228 |
| STAT1 | NM_007315 | S1542/STAT1.p3 | GGGCTCAGCTTTCAGAAGTG | 20 | SEQ ID NO: 229 |
| STAT1 | NM_007315 | S1543/STAT1.r3 | ACATGTTCAGCTGGTCCACA | 20 | SEQ ID NO: 230 |
| STAT1 | NM_007315 | S4878/STAT1.p3 | TGGCAGTTTTCTTCTGTCACCAAAA | 25 | SEQ ID NO: 231 |
| STAT3 | NM_003150 | S1545/STAT3.f1 | TCACATGCCACTTTGGTGTT | 20 | SEQ ID NO: 232 |
| STAT3 | NM_003150 | S1546/STAT3.r1 | CTTGCAGGAAGCGGCTATAC | 20 | SEQ ID NO: 233 |
| STAT3 | NM_003150 | S4881/STAT3.p1 | TCCTGGGAGAGATTGACCAGCA | 22 | SEQ ID NO: 234 |
| TBP | NM_003194 | S0262/TBP.f1 | GCCCGAAACGCCGAATATA | 19 | SEQ ID NO: 235 |
| TBP | NM_003194 | S0264/TBP.r1 | CGTGGCTCTCTTATCCTCATGAT | 23 | SEQ ID NO: 236 |
| TBP | NM_003194 | S4751/TBP.p1 | TACCGCAGCAAACCGCTTGGG | 21 | SEQ ID NO: 237 |
| TK1 | NM_003258 | S0866/TK1.f2 | GCCGGGAAGACCGTAATTGT | 20 | SEQ ID NO; 238 |
| TK1 | NM_003258 | S0927/TK1.r2 | CAGCGGCACCAGGTTCAG | 18 | SEQ ID NO: 239 |
| TK1 | NM_003258 | S4798/TK1.p2 | CAAATGGCTTCCTCTGGAAGGTCCCA | 26 | SEQ ID NO: 240 |
| TP53BP1 | NM_005657 | S1747/TP53P.f2 | TGCTGTTGCTGAGTCTGTTG | 20 | SEQ ID NO: 241 |
| TP53BP1 | NM_005657 | S1748/TP53BP.r2 | CTTGCCTGGCTTCACAGATA | 20 | SEQ ID NO: 242 |
| TP53BP1 | NM_005657 | S4924/TP53BP.p2 | CCAGTCCCCAGAAGACCATGTCTG | 24 | SEQ ID NO: 243 |

TABLE 2-continued

| TUBB | NM_001069 | S5826/TUBB.f3 | TGTGGTGAGGAAGGAGTCAG | 20 | SEQ ID NO: 244 |
| --- | --- | --- | --- | --- | --- |
| TUBB | NM_001069 | S5827/TUBB.r3 | CCCAGAGAGTGGGTCAGC | 18 | SEQ ID NO: 245 |
| TUBB | NM_001069 | S5828/TUBB.p3 | CTGTGACTGTCTCCAGGGCTTCCA | 24 | SEQ ID NO: 246 |
| VCAM1 | NM_001078 | S3505/VCAM1.f1 | TGGCTTCAGGAGCTGAATACC | 21 | SEQ ID NO: 247 |
| VCAM1 | NM_001078 | S3506/VCAM1.r1 | TGCTGTCGTGATGAGAAAATAGTG | 24 | SEQ ID NO: 248 |
| VCAM1 | NM_001078 | S3507/VCAM1.p1 | CAGGCACACACAGGTGGGACACAAAT | 26 | SEQ ID NO: 249 |
| Wnt-5a | NM_003392 | S6183/Wnt-5a.f1 | GTATCAGGACCACATGCAGTACATC | 25 | SEQ ID NO: 250 |
| Wnt-5a | NM_003392 | S6184/Wnt-5a.r1 | TGTCGGAATTGATACTGGCATT | 22 | SEQ ID NO: 251 |
| Wnt-5a | NM_003392 | S6185/Wnt-5a.p1 | TTGATGCCTGTCTTCGCGCCTTCT | 24 | SEQ ID NO: 252 |
| ZNF38 | NM_145914 | S5593/ZNF38.f3 | TTTCCAAACATCAGCGAGTC | 20 | SEQ ID NO: 253 |
| ZNF38 | NM_145914 | S5594/ZNF38.r3 | AACAGGAGCGCTTGAAAGTT | 20 | SEQ ID NO: 254 |
| ZNF38 | NM_145914 | S5595/ZNF38.p3 | ACGGTGCTTCTCCCTCTCCAGTG | 23 | SEQ ID NO: 255 |

TABLE 3

| | | Sequence | |
| --- | --- | --- | --- |
| A-Catenin | NM_001903 | CGTTCCGATCCTCTATACTGCATCCCAGGCATGCCTACAGCACCCTGATGTCGCAGCCTATAAGGCCAACAGGGACCT | SEQ ID NO: 256 |
| ABCC5 | NM_005688 | TGCAGACTGTACCATGCTGACCATTGCCCATCGCCTGCACACGGTTCTAGGCTCCGATAGGATTATGGTGCTGGCC | SEQ ID NO: 257 |
| AK055699 | AK055699 | CTGCATGTGATTGAATAAGAAACAAGAAAGTGACCACACCAAAGCCTCCCTGGCTGGTGTACAGGGATCAGGTCCACA | SEQ ID NO: 258 |
| AKAP-2 | NM_007203 | ACGAATTGTCGGTGAGGTCTCAGGATACCACAGTCCTGGAGACCCTATCCAATGATTTCAGCATGGAC | SEQ ID NO: 259 |
| AKT1 | NM_005163 | CGCTTCTATGGCGCTGAGATTGTGTCAGCCCTGGACTACCTGCACTCGGAGAAGAACGTGGTGTACCGGGA | SEQ ID NO: 260 |
| AKT2 | NM_001626 | TCCTGCCACCCTTCAAACCTCAGGTCACGTCCGAGGTCGACACAAGGTACTTCGATGATGAATTTACCGCC | SEQ ID NO: 261 |
| APC | NM_000038 | GGACAGCAGGAATGTGTTTCTCCATACAGGTCACGGGGAGCCAATGGTTCAGAAACAAATCGAGTGGGT | SEQ ID No: 262 |
| BAD | NM_032989 | GGGTCAGGTGCCTCGAGATCGGGCTTGGGCCCAGAGCATGTTCCAGATCCCAGAGTTTGAGCCGAGTGAGCAG | SEQ ID NO: 263 |
| BAG1 | NM_004323 | CGTTGTCAGCACTTGGAATACAAGATGGTTGCCGGGTCATGTTAATTGGGAAAAAGAACAGTCCACAGGAAGAGGTTGAAC | SEQ ID NO: 264 |
| BBC3 | NM_014417 | CCTGGAGGGTCCTGTACAATCTCATCATGGGACTCCTGCCCTTACCCAGGGGCCACAGAGCCCCCGAGATGGAGGCCAATTAG | SEQ ID NO: 265 |
| Bcl2 | NM_000633 | CAGATGGACCTAGTACCCACTGAGATTTCCACGCCGAAGGACAGCGATGGGAAAAATGCCCTTAAAATCATAGG | SEQ ID NO: 266 |
| CCND1 | NM_001758 | GCATGTTCGTGGCCTCTAAGATGAAGGAGACCATCCCCCTGACGGCCGAGAAGCTGTGCATCTACACCG | SEQ ID NO: 267 |
| CD18 | NM_000211 | CGTCAGGACCCACCATGTCTGCCCCATCACGCGGCCGAGACATGGCTTGGCCACAGCTCTTGAGGATGTCACCAATTAACC | SEQ ID NO: 268 |
| CD31 | NM_000442 | TGTATTTCAAGACCTCTGTGCACTTATTTATGAACCTGCCCTGCTCCCACAGAACACAGCAATTCCTCAGGCTAA | SEQ ID NO: 269 |
| CD3z | NM_000734 | AGATGAAGTGGAAGGCGCTTTTCACCGCGGCCATCCTGCAGGCACAGTTGCCGATTACAGAGGCA | SEQ ID NO: 270 |
| CD9 | NM_001769 | GGGCGTGGAACAGTTTATCTCAGACATCTGCCCCAAGAAGGACGTACTCGAAACCTTCACCGTG | SEQ ID NO: 271 |

TABLE 3-continued

| | | Sequence | |
|---|---|---|---|
| CDC20 | NM_001255 | TGGATTGGAGTTCTGGGAATGTACTGGCCGTGGCACTGGACAACAGTGTGTACCTGTGGA GTGCAAGC | SEQ ID NO: 272 |
| CDC25B | NM_021874 | AAACGAGCAGTTTGCCATCAGACGCTTCCAGTCTATGCCGGTGAGGCTGCTGGGCCACAG CCCCGTGCTTCGGAACATCACCAAC | SEQ ID NO: 273 |
| CEGP1 | NM_020974 | TGACAATCAGCACACCTGCATTCACCGCTCGGAAGAGGGCCTGAGCTGCATGAATAAGGA TCACGGCTGTAGTCACA | SEQ ID NO: 274 |
| CGA (CHGA official) | NM_001275 | CTGAAGGAGCTCCAAGACCTCGCTCTCCAAGGCGCCAAGGAGAGGGCACATCAGCAGAAG AAACACAGCGGTTTTG | SEQ ID NO: 275 |
| COL1A1 | NM_000088 | GTGGCCATCCAGCTGACCTTCCTGCGCCTGATGTCCACCGAGGCCTCCCAGAACATCACC TACCACTG | SEQ ID NO: 276 |
| COL1A2 | NM_000089 | CAGCCAAGAACTGGTATAGGAGCTCCAAGGACAAGAAACACGTCTGGCTAGGAGAAACTA TCAATGCTGGCAGCCAGTTT | SEQ ID NO: 277 |
| Contig 51037 | XM_058945 | CGACAGTTGCCGATGAAAGTTCTAATCTCTTCCCTCCTCCTGTTGCTGCCACTAATGCTGA TGTCCATGGTCTCTAGCAGCC | SEQ ID NO: 278 |
| CRABP1 | NM_004378 | AACTTCAAGGTCGGAGAAGGCTTTGAGGAGGAGACCGTGGACGGACGCAAGTGCAGGAGT TTAGCCA | SEQ ID NO: 279 |
| CRIP2 | NM_001312 | GTGCTACGCCACCCTGTTCGGACCCAAAGGCGTGAACATCGGGGGCGCGGGCTCCTACAT CTACGAGAAGCCCCTG | SEQ ID NO: 280 |
| CYBA | NM_000101 | GGTGCCTACTCCATTGTGGCGGGCGTGTTTGTGTGCCTGCTGGAGTACCCCCGGGGGAAG AGGAAGAAGGGCTCCAC | SEQ ID NO: 281 |
| DHPS | NM_013407 | GGGAGAACGGGATCAATAGGATCGGAAACCTGCTGGTGCCCAATGAGAATTACTGCAAGT TTGAGGACTGGCTGATGC | SEQ ID NO: 282 |
| DICER1 | NM_177438 | TCCAATTCCAGCATCACTGTGGAGAAAAGCTGTTTGTCTCCCCAGCATACTTTATCGCCT TCACTGCC | SEQ ID NO: 283 |
| DR4 | NM_003844 | TGCACAGAGGGTGTGGGTTACACCAATGCTTCCAACAATTTGTTTGCTTGCCTCCCATGT ACAGCTTGTAAATCAGATGAAGA | SEQ ID NO: 284 |
| E2F1 | NM_005225 | ACTCCCTCTACCCTTGAGCAAGGGCAGGGGTCCCTGAGCTGTTCTTCTGCCCCATACTGA AGGAACTGAGGCCTG | SEQ ID NO: 285 |
| ER2 | NM_001437 | TGGTCCATCGCCAGTTATCACATCTGTATGCGGAACCTCAAAAGAGTCCCTGGTGTGAAG CAAGATCGCTAGAACA | SEQ ID NO: 286 |
| ErbB3 | NM_001982 | CGGTTATGTCATGCCAGATACACACCTCAAAGGTACTCCCTCCTCCCGGGAAGGCACCCT TTCTTCAGTGGGTCTCAGTTC | SEQ ID NO: 287 |
| ERBB4 | NM_005235 | TGGCTCTTAATCAGTTTCGTTACCTGCCTCTGGAGAATTTACGCATTATTCGTGGGACAA AACTTTATGAGGATCGATATGCCTTG | SEQ ID NO: 288 |
| ERCC1 | NM_001983 | GTCCAGGTGGATGTGAAAGATCCCCAGCAGGCCCTCAAGGAGCTGGCTAAGATGTGTATC CTGGCCG | SEQ ID NO: 289 |
| ERK1 | Z11696 | ACGGATCACAGTGGAGGAAGCGCTGGCTCACCCGTACCTGGAGCAGTACTATGACCCGAC GGATGAG | SEQ ID NO: 290 |
| ESRRG | NM_001438 | CCAGCACCATTGTTGAAGATCCCCAGACCAAGTGTGAATACATGCTCAACTCGATGCCCA AGAGACT | SEQ ID NO: 291 |
| fasl | NM_000639 | GCACTTTGGGATTCTTTCCATTATGATTCTTTGTTACAGGCACCGAGAATGTTGTATTCA GTGAGGGTCTTCTTACATGC | SEQ ID NO: 292 |
| FBXO5 | NM_012177 | GGCTATTCCTCATTTTCTCTACAAAGTGGCCTCAGTGAACATGAAGAAGGTAGCCTCCTG GAGGAGAATTTCGGTGACAGTCTACAATCC | SEQ ID NO: 293 |
| FHIT | NM_002012 | CCAGTGGAGCGCTTCCATGACCTGCGTCCTGATGAAGTGGCCGATTTGTTTCAGACGACC CAGAGAG | SEQ ID NO: 294 |
| FUS | NM_004960 | GGATAATTCAGACAACAACACCATCTTTGTGCAAGGCCTGGGTGAGAATGTTACAATTGA GTCTGTGGCTGATTACTTCA | SEQ ID NO: 295 |
| FYN | NM_002037 | GAAGCGCAGATCATGAAGAAGCTGAAGCACGACAAGCTGGTCCAGCTCTATGCAGTGGTG TCTGAGGAG | SEQ ID NO: 296 |
| G-Catenin | NM_002230 | TCAGCAGCAAGGGCATCATGGAGGAGGATAGGGCCTGCGGGCGCCAGTACACGCTCAAGA AAACCACC | SEQ ID NO: 297 |

TABLE 3-continued

| | | Sequence | |
|---|---|---|---|
| GATA3 | NM_002051 | CAAAGGAGCTCACTGTGGTGTCTGTGTTCCAACCACTGAATCTGGACCCCATCTGTGAAT AAGCCATTCTGACTC | SEQ ID NO: 298 |
| GBP1 | NM_002053 | TTGGGAAATATTTGGGCATTGGTCTGGCCAAGTCTACAATGTCCCAATATCAAGGACAAC CACCCTAGCTTCT | SEQ ID NO: 299 |
| GBP2 | NM_004120 | GCATGGGAACCATCAACCAGCAGGCCATGGACCAACTTCACTATGTGACAGAGCTGACAG ATCGAATCAAGGCAAACTCCTCA | SEQ ID NO: 300 |
| GGPS1 | NM_004837 | CTCCGACGTGGCTTTCCAGTGGCCCACAGCATCTATGGAATCCCATCTGTCATCAATTCT GCCAATTACG | SEQ ID NO: 301 |
| GRB7 | NM_005310 | CCATCTGCATCCATCTTGTTTGGGCTCCCCACCCTTGAGAAGTGCCTCAGATAATACCCT GGTGGCC | SEQ ID NO: 302 |
| Hepsin | NM_002151 | AGGCTGCTGGAGGTCATCTCCGTGTGTGATTGCCCCAGAGGCCGTTTCTTGGCCGCCATC TGCCAAGACTGTGGCCGCAGGAAG | SEQ ID NO: 303 |
| HLA-DPB1 | NM_002121 | TCCATGATGGTTCTGCAGGTTTCTGCGGCCCCCCGGACAGTGGCTCTGACGGCGTTACTG ATGGTGCTGCTCA | SEQ ID NO: 304 |
| ID2 | NM_002166 | AACGACTGCTACTCCAAGCTCAAGGAGCTGGTGCCCAGCATCCCCCAGAACAAGAAGGTG AGCAAGATGGAAATCC | SEQ ID NO: 305 |
| IGF1R | NM_000875 | GCATGGTAGCCGAAGATTTCACAGTCAAAATCGGAGATTTTGGTATGACGCGAGATATCT ATGAGACAGACTATTACCGGAAA | SEQ ID NO: 306 |
| IL6 | NM_000600 | CCTGAACCTTCCAAAGATGGCTGAAAAAGATGGATGCTTCCAATCTGGATTCAATGAGGA GACTTGCCTGGT | SEQ ID NO: 307 |
| ILT-2 | NM_006669 | AGCCATCACTCTCAGTGCAGCCAGGTCCTATCGTGGCCCCTGAGGAGACCCTGACTCTGC AGT | SEQ ID NO: 308 |
| IRS1 | NM_005544 | CCACAGCTCACCTTCTGTCAGGTGTCCATCCCAGCTCCAGCCAGCTCCCAGAGAGGAAGA GACTGGCACTGAGG | SEQ ID NO: 309 |
| KRT18 | NM_000224 | AGAGATCGAGGCTCTCAAGGAGGAGCTGCTCTTCATGAAGAAGAACCACGAAGAGGAAGT AAAAGGCC | SEQ ID NO: 310 |
| MAPK14 | NM_139012 | TGAGTGGAAAAGCCTGACCTATGATGAAGTCATCAGCTTTGTGCCACCACCCCTTGACCA AGAAGAGATGGAGTCC | SEQ ID NO: 311 |
| MCM2 | NM_004526 | GACTTTTGCCCGCTACCTTTCATTCCGGCGTGACAACAATGAGCTGTTGCTCTTCATACT GAAGCAGTTAGTGGC | SEQ ID NO: 312 |
| MCM6 | NM_005915 | TGATGGTCCTATGTGTCACATTCATCACAGGCATACCAACACAGGCTTCAGCACTTCCTT TGGTGTGTTTCCTGTCCCA | SEQ ID NO: 313 |
| MCP1 | NM_002982 | CGCTCAGCCAGATGCAATCAATGCCCCAGTCACCTGCTGTTATAACTTCACCAATAGGAA GATCTCAGTGC | SEQ ID NO: 314 |
| MGMT | NM_002412 | GTGAAATGAAACGCACCACACTGGACAGCCCTTTGGGGAAGCTGGAGCTGTCTGGTTGTG AGCAGGGTC | SEQ ID NO: 315 |
| MMP12 | NM_002426 | CCAACGCTTGCCAAATCCTGACAATTCAGAACCAGCTCTCTGTGACCCCAATTTGAGTTT TGATGCTGTCACTACCGT | SEQ ID NO: 316 |
| MSH3 | NM_002439 | TGATTACCATCATGGCTCAGATTGGCTCCTATGTTCCTGCAGAAGAAGCGACAATTGGGA TTGTGGATGGCATTTTCACAAG | SEQ ID NO: 317 |
| MTA1 | NM_004689 | CCGCCCTCACCTGAAGAGAAACGCGCTCCTTGGCGGACACTGGGGGAGGAGAGGAAGAAG CGCGGCTAACTTATTCC | SEQ ID NO: 318 |
| MUC1 | NM_002456 | GGCCAGGATCTGTGGTGGTACAATTGACTCTGGCCTTCCGAGAAGGTACCATCAATGTCC ACGACGTGGAG | SEQ ID NO: 319 |
| NPD009 (ABAT officia | NM_020686 | GGCTGTGGCTGAGGCTGTAGCATCTCTGCTGGAGGTGAGACACTCTGGGAACTGATTTGA CCTCGAATGCTCC | SEQ ID NO: 320 |
| PR | NM_000926 | GCATCAGGCTGTCATTATGGTGTCCTTACCTGTGGGAGCTGTAAGGTCTTCTTTAAGAGG GCAATGGAAGGGCAGCACAACTACT | SEQ ID NO: 321 |
| PRKCD | NM_006254 | CTGACACTTGCCGCAGAGAATCCCTTTCTCACCCACCTCATCTGCACCTTCCAGACCAAG GACCACCT | SEQ ID NO: 322 |
| PTPD1 | NM_007039 | CGCTTGCCTAACTCATACTTTCCCGTTGACACTTGATCCACGCAGCGTGGCACTGGGACG TAAGTGGCGCAGTCTGAATGG | SEQ ID NO: 323 |

TABLE 3-continued

| | | Sequence | |
|---|---|---|---|
| RAB6C | NM_032144 | GCGACAGCTCCTCTAGTTCCACCATGTCCGCGGGCGGAGACTTCGGGAATCCGCTGAGGA AATTCAAGCTGGTGTTCC | SEQ ID NO: 324 |
| RALBP1 | NM_006788 | GGTGTCAGATATAAATGTGCAAATGCCTTCTTGCTGTCCTGTCGGTCTCAGTACGTTCAC TTTATAGCTGCTGGCAATATCGAA | SEQ ID NO: 325 |
| RAP1GDS1 | NM_021159 | TGTGGATGCTGGATTGATTTCACCACTGGTGCAGCTGCTAAATAGCAAAGACCAGGAAGT GCTGCTT | SEQ ID NO: 326 |
| RASSF1 | NM_007182 | AGTGGGAGACACCTGACCTTTCTCAAGCTGAGATTGAGCAGAAGATCAAGGAGTACAATG CCCAGATCA | SEQ ID NO: 327 |
| rhoC | NM_005167 | CCCGTTCGGTCTGAGGAAGGCCGGGACATGGCGAACCGGATCAGTGCCTTTGGCTACCTT GAGTGCTC | SEQ ID NO: 328 |
| RUNX1 | NM_001754 | AACAGAGACATTGCCAACCATATTGGATCTGCTTGCTGTCCAAACCAGCAAACTTCCTGG GCAAATCAC | SEQ ID NO: 329 |
| SEMA3F | NM_004186 | CGCGAGCCCCTCATTATACACTGGGCAGCCTCCCCACAGCGCATCGAGGAATGCGTGCTC TCAGGCAAGGATGTCAACGGCGAGTG | SEQ ID NO: 330 |
| SGCB | NM_000232 | CAGTGGAGACCAGTTGGGTAGTGGTGACTGGGTACGCTACAAGCTCTGCATGTGTGCTGA TGGGACGCTCTTCAAGG | SEQ ID NO; 331 |
| STAT1 | NM_007315 | GGGCTCAGCTTTCAGAAGTGCTGAGTTGGCAGTTTTCTTCTGTCACCAAAAGAGGTCTCA ATGTGGACCAGCTGAACATGT | SEQ ID NO: 332 |
| STAT5 | NM_003150 | TCACATGCCACTTTGGTGTTTCATAATCTCCTGGGAGAGATTGACCAGCAGTATAGCCGC TTCCTGCAAG | SEQ ID NO: 333 |
| TBP | NM_003194 | GCCCGAAACGCCGAATATAATCCCAAGCGGTTTGCTGCGGTAATCATGAGGATAAGAGAG CCACG | SEQ ID NO: 334 |
| TK1 | NM_003258 | GCCGGGAAGACCGTAATTGTGGCTGCACTGGATGGGACCTTCCAGAGGAAGCCATTTGGG GCCATCCTGAACCTGGTGCCGCTG | SEQ ID NO: 335 |
| TP53BP1 | NM_005657 | TGCTGTTGCTGAGTCTGTTGCCAGTCCCCAGAAGACCATGTCTGTGTTGAGCTGTATCTG TGAAGCCAGGCAAG | SEQ ID NO: 336 |
| TUBB | NM_001069 | TGTGGTGAGGAAGGAGTCAGAGAGCTGTGACTGTCTCCAGGGCTTCCAGCTGACCCACTC TCTGGG | SEQ ID NO: 337 |
| VCAM1 | NM_001078 | TGGCTTCAGGAGCTGAATACCCTCCCAGGCACACACAGGTGGGACACAAATAAGGGTTTT GGAACCACTATTTTCTCATCACGACAGCA | SEQ ID NO: 338 |
| Wnt-5a | NM_003392 | GTATCAGGACCACATGCAGTACATCGGAGAAGGCGCGAAGACAGGCATCAAAGAATGCCA GTATCAATTCCGACA | SEQ ID NO: 339 |
| ZNF38 | NM_145914 | TTTCCAAACATCAGCGAGTCCACACTGGAGAGGGAGAAGCACCGTAACTTTCAAGCGCTC CTGTT | SEQ ID NO: 340 |

---

What is claimed is:

1. A method for predicting the response of a human patient diagnosed with breast cancer to chemotherapy and of treating the patient comprising:
   extracting RNA from a fresh, frozen, or fixed, paraffin-embedded tissue (FPET) sample comprising cancer cells obtained from said patient;
   reverse transcribing an RNA transcript of GBP1 to produce cDNA of GBP1;
   amplifying the cDNA of GBP1 using a PCR-based method to produce an amplicon of the RNA transcript of GBP1;
   quantitatively assaying a level of the amplicon of the RNA transcript of GBP1;
   normalizing said level against a level of an amplicon of at least one reference RNA transcript in the sample to provide a normalized GBP1 amplicon level;
   comparing the normalized GBP1 amplicon level to a normalized GBP1 amplicon level in reference samples comprising breast cancer cells;
   predicting the response of said patient to chemotherapy, wherein the patient is predicted to have an increased likelihood of response to chemotherapy if the patient has an increased normalized GBP1 amplicon level compared to the GBP1 amplicon level in the reference samples; and
   administering chemotherapy to the patient with an increased normalized GBP1 amplicon level compared to the GBP1 amplicon level in the reference samples.

2. The method of claim 1, wherein said response is a complete pathological response.

3. The method of claim 1, wherein said breast cancer is invasive breast cancer.

4. The method of claim 1, wherein said chemotherapy is adjuvant chemotherapy.

5. The method of claim 1, wherein said chemotherapy is neoadjuvant chemotherapy.

6. The method of claim 5, wherein said neoadjuvant chemotherapy comprises the administration of a taxane derivative.

7. The method of claim 6, wherein said taxane is docetaxel or paclitaxel.

8. The method of claim 6, wherein said neoadjuvant chemotherapy further comprises administration of a member of the anthracycline class of anti-cancer agents.

9. The method of claim 1, wherein said chemotherapy further comprises the administration of an additional anti-cancer agent.

10. The method of claim 9, wherein said additional anti-cancer agent is a member of the anthracycline class of anti-cancer agents.

11. The method of claim 10, wherein said anthracycline is doxorubicin.

12. The method of claim 9, wherein said additional anti-cancer agent is a topoisomerase inhibitor.

13. The method of claim 1, wherein the sample is from fine needle, core, or other types of biopsy.

14. The method of claim 1, further comprising creating a report summarizing the prediction of the response of said patient to chemotherapy.

15. The method of claim 14, wherein said report includes a recommendation for a treatment modality for said patient.

16. The method of claim 1, wherein the sample is a fixed, paraffin-embedded tissue (FPET) sample.

17. The method of claim 1, wherein said chemotherapy comprises the administration of a taxane derivative and further comprises administration of a member of the anthracycline of anti-cancer agents.

18. A method for predicting the response of a human patient diagnosed with breast cancer to chemotherapy-comprising:
   extracting RNA from a fresh, frozen, or fixed, paraffin-embedded tissue (FPET) sample comprising cancer cells obtained from said patient;
   reverse transcribing an RNA transcript of GBP1 to produce cDNA of GBP1;
   amplifying the cDNA of GBP1 using a PCR-based method, wherein the PCR-based method comprises use of a polynucleotide comprising a sequence selected from SEQ ID NO.: 130-132, to produce an amplicon of the RNA transcript of GBP1;
   quantitatively assaying a level of the amplicon of the RNA transcript of GBP1;
   normalizing said level against a level of an amplicon of at least one reference RNA transcript in the sample to provide a normalized GBP1 amplicon level;
   comparing the normalized GBP1 amplicon level to a normalized GBP1 amplicon level in reference samples comprising breast cancer cells; and
   predicting the response of said patient to chemotherapy, wherein the patient is predicted to have an increased likelihood of response to chemotherapy if the patient has an increased normalized GBP1 amplicon level compared to the GBP1 amplicon level in the reference samples.

* * * * *

SEQUENCE LISTING

<160> NUMBER OF SEQ ID NOS: 340

<210> SEQ ID NO 1
<211> LENGTH: 23
<212> TYPE: DNA
<213> ORGANISM: Artificial Sequence
<220> FEATURE:
<223> OTHER INFORMATION: Synthetic Oligonucleotide Forward Primer

<400> SEQUENCE: 1
cgttccgatc ctctatactg cat                                           23

<210> SEQ ID NO 2
<211> LENGTH: 22
<212> TYPE: DNA
<213> ORGANISM: Artificial Sequence
<220> FEATURE:
<223> OTHER INFORMATION: Synthetic Oligonucleotide Reverse Primer

<400> SEQUENCE: 2
aggtccctgt tggccttata gg                                              22

<210> SEQ ID NO 3
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 3
atgcctacag caccctgatg tcgca                                           25

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 4
tgcagactgt accatgctga                                                 20

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 5
ggccagcacc ataatcctat                                                 20

<210> SEQ ID NO 6
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 6
ctgcacacgg ttctaggctc cg                                              22

<210> SEQ ID NO 7
<211> LENGTH: 27
<212> TYPE: DNA
<213> ORGANISM: Artificial Sequence
<220> FEATURE:
<223> OTHER INFORMATION: Synthetic Oligonucleotide Forward Primer

<400> SEQUENCE: 7
ctgcatgtga ttgaataaga aacaaga                                         27

<210> SEQ ID NO 8
<211> LENGTH: 22
<212> TYPE: DNA
<213> ORGANISM: Artificial Sequence
<220> FEATURE:
<223> OTHER INFORMATION: Synthetic Oligonucleotide Reverse Primer

<400> SEQUENCE: 8
tgtggacctg atccctgtac ac                                              22

<210> SEQ ID NO 9

```
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 9
tgaccacacc aaagcctccc tgg                                              23

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 10
acgaattgtc ggtgaggtct                                                  20

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 11
gtccatgctg aaatcattgg                                                  20

<210> SEQ ID NO 12
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 12
caggatacca cagtcctgga gaccc                                            25

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 13
cgcttctatg gcgctgagat                                                  20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 14
tcccggtaca ccacgttctt                                                  20

<210> SEQ ID NO 15
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 15
```

```
cagccctgga ctacctgcac tcgg                                          24

<210> SEQ ID NO 16
<211> LENGTH: 19
<212> TYPE: DNA
<213> ORGANISM: Artificial Sequence
<220> FEATURE:
<223> OTHER INFORMATION: Synthetic Oligonucleotide Forward Primer

<400> SEQUENCE: 16
tcctgccacc cttcaaacc                                                19

<210> SEQ ID NO 17
<211> LENGTH: 21
<212> TYPE: DNA
<213> ORGANISM: Artificial Sequence
<220> FEATURE:
<223> OTHER INFORMATION: Synthetic Oligonucleotide Reverse Primer

<400> SEQUENCE: 17
ggcggtaaat tcatcatcga a                                             21

<210> SEQ ID NO 18
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 18
caggtcacgt ccgaggtcga caca                                          24

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 19
ggacagcagg aatgtgtttc                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 20
acccactcga tttgtttctg                                               20

<210> SEQ ID NO 21
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 21
cattggctcc ccgtgacctg ta                                            22

<210> SEQ ID NO 22
<211> LENGTH: 19
<212> TYPE: DNA
```

```
<213> ORGANISM: Artificial Sequence
<220> FEATURE:
<223> OTHER INFORMATION: Synthetic Oligonucleotide Forward Primer

<400> SEQUENCE: 22
gggtcaggtg cctcgagat                                                  19

<210> SEQ ID NO 23
<211> LENGTH: 21
<212> TYPE: DNA
<213> ORGANISM: Artificial Sequence
<220> FEATURE:
<223> OTHER INFORMATION: Synthetic Oligonucleotide Reverse Primer

<400> SEQUENCE: 23
ctgctcactc ggctcaaact c                                               21

<210> SEQ ID NO 24
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 24
tgggcccaga gcatgttcca gatc                                            24

<210> SEQ ID NO 25
<211> LENGTH: 23
<212> TYPE: DNA
<213> ORGANISM: Artificial Sequence
<220> FEATURE:
<223> OTHER INFORMATION: Synthetic Oligonucleotide Forward Primer

<400> SEQUENCE: 25
cgttgtcagc acttggaata caa                                             23

<210> SEQ ID NO 26
<211> LENGTH: 24
<212> TYPE: DNA
<213> ORGANISM: Artificial Sequence
<220> FEATURE:
<223> OTHER INFORMATION: Synthetic Oligonucleotide Reverse Primer

<400> SEQUENCE: 26
gttcaacctc ttcctgtgga ctgt                                            24

<210> SEQ ID NO 27
<211> LENGTH: 26
<212> TYPE: DNA
<213> ORGANISM: Artificial Sequence
<220> FEATURE:
<223> OTHER INFORMATION: Synthetic Oligonucleotide Probe

<400> SEQUENCE: 27
cccaattaac atgacccggc aaccat                                          26

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 28
cctggagggt cctgtacaat                                                 20
```

<210> SEQ ID NO 29
<211> LENGTH: 19
<212> TYPE: DNA
<213> ORGANISM: Artificial Sequence
<220> FEATURE:
<223> OTHER INFORMATION: Synthetic Oligonucleotide Reverse Primer

<400> SEQUENCE: 29
ctaattgggc tccatctcg                                                19

<210> SEQ ID NO 30
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 30
catcatggga ctcctgccct tacc                                          24

<210> SEQ ID NO 31
<211> LENGTH: 25
<212> TYPE: DNA
<213> ORGANISM: Artificial Sequence
<220> FEATURE:
<223> OTHER INFORMATION: Synthetic Oligonucleotide Forward Primer

<400> SEQUENCE: 31
cagatggacc tagtacccac tgaga                                         25

<210> SEQ ID NO 32
<211> LENGTH: 24
<212> TYPE: DNA
<213> ORGANISM: Artificial Sequence
<220> FEATURE:
<223> OTHER INFORMATION: Synthetic Oligonucleotide Reverse Primer

<400> SEQUENCE: 32
cctatgattt aagggcattt ttcc                                          24

<210> SEQ ID NO 33
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 33
ttccacgccg aaggacagcg at                                            22

<210> SEQ ID NO 34
<211> LENGTH: 21
<212> TYPE: DNA
<213> ORGANISM: Artificial Sequence
<220> FEATURE:
<223> OTHER INFORMATION: Synthetic Oligonucleotide Forward Primer

<400> SEQUENCE: 34
gcatgttcgt ggcctctaag a                                             21

<210> SEQ ID NO 35
<211> LENGTH: 22
<212> TYPE: DNA
<213> ORGANISM: Artificial Sequence
<220> FEATURE:

<223> OTHER INFORMATION: Synthetic Oligonucleotide Reverse Primer

<400> SEQUENCE: 35
cggtgtagat gcacagcttc tc                                            22

<210> SEQ ID NO 36
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 36
aaggagacca tccccctgac ggc                                           23

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 37
cgtcaggacc caccatgtct                                               20

<210> SEQ ID NO 38
<211> LENGTH: 24
<212> TYPE: DNA
<213> ORGANISM: Artificial Sequence
<220> FEATURE:
<223> OTHER INFORMATION: Synthetic Oligonucleotide Reverse Primer

<400> SEQUENCE: 38
ggttaattgg tgacatcctc aaga                                          24

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide Probe

<400> SEQUENCE: 39
cgcggccgag acatggcttg                                               20

<210> SEQ ID NO 40
<211> LENGTH: 25
<212> TYPE: DNA
<213> ORGANISM: Artificial Sequence
<220> FEATURE:
<223> OTHER INFORMATION: Synthetic Oligonucleotide Forward Primer

<400> SEQUENCE: 40
tgtatttcaa gacctctgtg cactt                                         25

<210> SEQ ID NO 41
<211> LENGTH: 23
<212> TYPE: DNA
<213> ORGANISM: Artificial Sequence
<220> FEATURE:
<223> OTHER INFORMATION: Synthetic Oligonucleotide Reverse Primer

<400> SEQUENCE: 41
ttagcctgag gaattgctgt gtt                                           23

```
<210> SEQ ID NO 42
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 42
tttatgaacc tgccctgctc ccaca                                          25

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 43
agatgaagtg gaaggcgctt                                                20

<210> SEQ ID NO 44
<211> LENGTH: 21
<212> TYPE: DNA
<213> ORGANISM: Artificial Sequence
<220> FEATURE:
<223> OTHER INFORMATION: Synthetic Oligonucleotide Reverse Primer

<400> SEQUENCE: 44
tgcctctgta atcggcaact g                                              21

<210> SEQ ID NO 45
<211> LENGTH: 18
<212> TYPE: DNA
<213> ORGANISM: Artificial Sequence
<220> FEATURE:
<223> OTHER INFORMATION: Synthetic Oligonucleotide Probe

<400> SEQUENCE: 45
caccgcggcc atcctgca                                                  18

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 46
gggcgtggaa cagtttatct                                                20

<210> SEQ ID NO 47
<211> LENGTH: 19
<212> TYPE: DNA
<213> ORGANISM: Artificial Sequence
<220> FEATURE:
<223> OTHER INFORMATION: Synthetic Oligonucleotide Reverse Primer

<400> SEQUENCE: 47
cacggtgaag gtttcgagt                                                 19

<210> SEQ ID NO 48
<211> LENGTH: 24
<212> TYPE: DNA
<213> ORGANISM: Artificial Sequence
<220> FEATURE:
<223> OTHER INFORMATION: Synthetic Oligonucleotide Probe
```

<400> SEQUENCE: 48
agacatctgc cccaagaagg acgt                                              24

<210> SEQ ID NO 49
<211> LENGTH: 21
<212> TYPE: DNA
<213> ORGANISM: Artificial Sequence
<220> FEATURE:
<223> OTHER INFORMATION: Synthetic Oligonucleotide Forward Primer

<400> SEQUENCE: 49
tggattggag ttctgggaat g                                                 21

<210> SEQ ID NO 50
<211> LENGTH: 22
<212> TYPE: DNA
<213> ORGANISM: Artificial Sequence
<220> FEATURE:
<223> OTHER INFORMATION: Synthetic Oligonucleotide Reverse Primer

<400> SEQUENCE: 50
gcttgcactc cacaggtaca ca                                                22

<210> SEQ ID NO 51
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 51
actggccgtg gcactggaca aca                                               23

<210> SEQ ID NO 52
<211> LENGTH: 21
<212> TYPE: DNA
<213> ORGANISM: Artificial Sequence
<220> FEATURE:
<223> OTHER INFORMATION: Synthetic Oligonucleotide Forward Primer

<400> SEQUENCE: 52
aaacgagcag tttgccatca g                                                 21

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 53
gttggtgatg ttccgaagca                                                   20

<210> SEQ ID NO 54
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 54
cctcaccggc atagactgga agcg                                              24

<210> SEQ ID NO 55
<211> LENGTH: 21

<212> TYPE: DNA
<213> ORGANISM: Artificial Sequence
<220> FEATURE:
<223> OTHER INFORMATION: Synthetic Oligonucleotide Forward Primer

<400> SEQUENCE: 55
tgacaatcag cacacctgca t                                              21

<210> SEQ ID NO 56
<211> LENGTH: 23
<212> TYPE: DNA
<213> ORGANISM: Artificial Sequence
<220> FEATURE:
<223> OTHER INFORMATION: Synthetic Oligonucleotide Reverse Primer

<400> SEQUENCE: 56
tgtgactaca gccgtgatcc tta                                            23

<210> SEQ ID NO 57
<211> LENGTH: 20
<212> TYPE: DNA
<213> ORGANISM: Artificial Sequence
<220> FEATURE:
<223> OTHER INFORMATION: Synthetic Oligonucleotide Probe

<400> SEQUENCE: 57
caggccctct tccgagcggt                                                20

<210> SEQ ID NO 58
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 58
ctgaaggagc tccaagacct                                                20

<210> SEQ ID NO 59
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 59
caaaaccgct gtgtttcttc                                                20

<210> SEQ ID NO 60
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 60
tgctgatgtg ccctctcctt gg                                             22

<210> SEQ ID NO 61
<211> LENGTH: 18
<212> TYPE: DNA
<213> ORGANISM: Artificial Sequence
<220> FEATURE:
<223> OTHER INFORMATION: Synthetic Oligonucleotide Forward Primer

<400> SEQUENCE: 61

```
gtggccatcc agctgacc                                                   18

<210> SEQ ID NO 62
<211> LENGTH: 23
<212> TYPE: DNA
<213> ORGANISM: Artificial Sequence
<220> FEATURE:
<223> OTHER INFORMATION: Synthetic Oligonucleotide Reverse Primer

<400> SEQUENCE: 62
cagtggtagg tgatgttctg gga                                             23

<210> SEQ ID NO 63
<211> LENGTH: 21
<212> TYPE: DNA
<213> ORGANISM: Artificial Sequence
<220> FEATURE:
<223> OTHER INFORMATION: Synthetic Oligonucleotide Probe

<400> SEQUENCE: 63
tcctgcgcct gatgtccacc g                                               21

<210> SEQ ID NO 64
<211> LENGTH: 24
<212> TYPE: DNA
<213> ORGANISM: Artificial Sequence
<220> FEATURE:
<223> OTHER INFORMATION: Synthetic Oligonucleotide Forward Primer

<400> SEQUENCE: 64
cagccaagaa ctggtatagg agct                                            24

<210> SEQ ID NO 65
<211> LENGTH: 19
<212> TYPE: DNA
<213> ORGANISM: Artificial Sequence
<220> FEATURE:
<223> OTHER INFORMATION: Synthetic Oligonucleotide Reverse Primer

<400> SEQUENCE: 65
aaactggctg ccagcattg                                                  19

<210> SEQ ID NO 66
<211> LENGTH: 30
<212> TYPE: DNA
<213> ORGANISM: Artificial Sequence
<220> FEATURE:
<223> OTHER INFORMATION: Synthetic Oligonucleotide Probe

<400> SEQUENCE: 66
tctcctagcc agacgtgttt cttgtccttg                                      30

<210> SEQ ID NO 67
<211> LENGTH: 24
<212> TYPE: DNA
<213> ORGANISM: Artificial Sequence
<220> FEATURE:
<223> OTHER INFORMATION: Synthetic Oligonucleotide Forward Primer

<400> SEQUENCE: 67
cgacagttgc gatgaaagtt ctaa                                            24

<210> SEQ ID NO 68
<211> LENGTH: 22
<212> TYPE: DNA
<213> ORGANISM: Artificial Sequence
```

```
<220> FEATURE:
<223> OTHER INFORMATION: Synthetic Oligonucleotide Reverse Primer

<400> SEQUENCE: 68
ggctgctaga gaccatggac at                                              22

<210> SEQ ID NO 69
<211> LENGTH: 27
<212> TYPE: DNA
<213> ORGANISM: Artificial Sequence
<220> FEATURE:
<223> OTHER INFORMATION: Synthetic Oligonucleotide Probe

<400> SEQUENCE: 69
cctcctcctg ttgctgccac taatgct                                         27

<210> SEQ ID NO 70
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 70
aacttcaagg tcggagaagg                                                 20

<210> SEQ ID NO 71
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 71
tggctaaact cctgcacttg                                                 20

<210> SEQ ID NO 72
<211> LENGTH: 21
<212> TYPE: DNA
<213> ORGANISM: Artificial Sequence
<220> FEATURE:
<223> OTHER INFORMATION: Synthetic Oligonucleotide Probe

<400> SEQUENCE: 72
ccgtccacgg tctcctcctc a                                               21

<210> SEQ ID NO 73
<211> LENGTH: 18
<212> TYPE: DNA
<213> ORGANISM: Artificial Sequence
<220> FEATURE:
<223> OTHER INFORMATION: Synthetic Oligonucleotide Foward Primer

<400> SEQUENCE: 73
gtgctacgcc accctgtt                                                   18

<210> SEQ ID NO 74
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 74 cagggggcttc tcgtagatgt                                                20
```

```
<210> SEQ ID NO 75
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 75
ccgatgttca cgcctttggg tc                                            22

<210> SEQ ID NO 76
<211> LENGTH: 19
<212> TYPE: DNA
<213> ORGANISM: Artificial Sequence
<220> FEATURE:
<223> OTHER INFORMATION: Synthetic Oligonucleotide Foward Primer

<400> SEQUENCE: 76
ggtgcctact ccattgtgg                                                19

<210> SEQ ID NO 77
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 77
gtggagccct tcttcctctt                                               20

<210> SEQ ID NO 78
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 78
tactccagca ggcacacaaa cacg                                          24

<210> SEQ ID NO 79
<211> LENGTH: 22
<212> TYPE: DNA
<213> ORGANISM: Artificial Sequence
<220> FEATURE:
<223> OTHER INFORMATION: Synthetic Oligonucleotide Forward Primer

<400> SEQUENCE: 79
gggagaacgg gatcaatagg at                                            22

<210> SEQ ID NO 80
<211> LENGTH: 21
<212> TYPE: DNA
<213> ORGANISM: Artificial Sequence
<220> FEATURE:
<223> OTHER INFORMATION: Synthetic Oligonucleotide Reverse Primer

<400> SEQUENCE: 80
gcatcagcca gtcctcaaac t                                             21

<210> SEQ ID NO 81
<211> LENGTH: 24
<212> TYPE: DNA
<213> ORGANISM: Artificial Sequence
<220> FEATURE:
<223> OTHER INFORMATION: Synthetic Oligonucleotide Probe
```

```
<400> SEQUENCE: 81
ctcattgggc accagcaggt ttcc                                              24

<210> SEQ ID NO 82
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 82
tccaattcca gcatcactgt                                                   20

<210> SEQ ID NO 83
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 83
ggcagtgaag gcgataaagt                                                   20

<210> SEQ ID NO 84
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 84
agaaaagctg tttgtctccc cagca                                             25

<210> SEQ ID NO 85
<211> LENGTH: 21
<212> TYPE: DNA
<213> ORGANISM: Artificial Sequence
<220> FEATURE:
<223> OTHER INFORMATION: Synthetic Oligonucleotide Forward Primer

<400> SEQUENCE: 85
tgcacagagg gtgtgggtta c                                                 21

<210> SEQ ID NO 86
<211> LENGTH: 28
<212> TYPE: DNA
<213> ORGANISM: Artificial Sequence
<220> FEATURE:
<223> OTHER INFORMATION: Synthetic Oligonucleotide Reverse Primer

<400> SEQUENCE: 86
tcttcatctg atttacaagc tgtacatg                                          28

<210> SEQ ID NO 87
<211> LENGTH: 29
<212> TYPE: DNA
<213> ORGANISM: Artificial Sequence
<220> FEATURE:
<223> OTHER INFORMATION: Synthetic Oligonucleotide Probe

<400> SEQUENCE: 87
caatgcttcc aacaatttgt ttgcttgcc                                         29

<210> SEQ ID NO 88
```

```
<210> SEQ ID NO 88
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 88
actccctcta cccttgagca                                                  20

<210> SEQ ID NO 89
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 89
caggcctcag ttccttcagt                                                  20

<210> SEQ ID NO 90
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 90
cagaagaaca gctcagggac ccct                                             24

<210> SEQ ID NO 91
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 91
tggtccatcg ccagttatca                                                  20

<210> SEQ ID NO 92
<211> LENGTH: 23
<212> TYPE: DNA
<213> ORGANISM: Artificial Sequence
<220> FEATURE:
<223> OTHER INFORMATION: Synthetic Oligonucleotide Reverse Primer

<400> SEQUENCE: 92
tgttctagcg atcttgcttc aca                                              23

<210> SEQ ID NO 93
<211> LENGTH: 30
<212> TYPE: DNA
<213> ORGANISM: Artificial Sequence
<220> FEATURE:
<223> OTHER INFORMATION: Synthetic Oligonucleotide Probe

<400> SEQUENCE: 93
atctgtatgc ggaacctcaa aagagtccct                                       30

<210> SEQ ID NO 94
<211> LENGTH: 23
<212> TYPE: DNA
<213> ORGANISM: Artificial Sequence
<220> FEATURE:
<223> OTHER INFORMATION: Synthetic Oligonucleotide Forward Primer

<400> SEQUENCE: 94
```
cggttatgtc atgccagata cac                                           23

<210> SEQ ID NO 95
<211> LENGTH: 24
<212> TYPE: DNA
<213> ORGANISM: Artificial Sequence
<220> FEATURE:
<223> OTHER INFORMATION: Synthetic Oligonucleotide Reverse Primer

<400> SEQUENCE: 95
gaactgagac ccactgaaga aagg                                          24

<210> SEQ ID NO 96
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 96
cctcaaaggt actccctcct cccgg                                         25

<210> SEQ ID NO 97
<211> LENGTH: 25
<212> TYPE: DNA
<213> ORGANISM: Artificial Sequence
<220> FEATURE:
<223> OTHER INFORMATION: Synthetic Oligonucleotide Forward Primer

<400> SEQUENCE: 97
tggctcttaa tcagtttcgt tacct                                         25

<210> SEQ ID NO 98
<211> LENGTH: 25
<212> TYPE: DNA
<213> ORGANISM: Artificial Sequence
<220> FEATURE:
<223> OTHER INFORMATION: Synthetic Oligonucleotide Reverse Primer

<400> SEQUENCE: 98
caaggcatat cgatcctcat aaagt                                         25

<210> SEQ ID NO 99
<211> LENGTH: 30
<212> TYPE: DNA
<213> ORGANISM: Artificial Sequence
<220> FEATURE:
<223> OTHER INFORMATION: Synthetic Oligonucleotide Probe

<400> SEQUENCE: 99
tgtcccacga ataatgcgta aattctccag                                    30

<210> SEQ ID NO 100
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 100
gtccaggtgg atgtgaaaga                                               20

<210> SEQ ID NO 101
<211> LENGTH: 20
<212> TYPE: DNA

```
<213> ORGANISM: Artificial Sequence
<220> FEATURE:
<223> OTHER INFORMATION: Synthetic Oligonucleotide Reverse Primer

<400> SEQUENCE: 101
cggccaggat acacatctta                                                20

<210> SEQ ID NO 102
<211> LENGTH: 21
<212> TYPE: DNA
<213> ORGANISM: Artificial Sequence
<220> FEATURE:
<223> OTHER INFORMATION: Synthetic Oligonucleotide Probe

<400> SEQUENCE: 102
cagcaggccc tcaaggagct g                                              21

<210> SEQ ID NO 103
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 103
acggatcaca gtggaggaag                                                20

<210> SEQ ID NO 104
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 104
ctcatccgtc gggtcatagt                                                20

<210> SEQ ID NO 105
<211> LENGTH: 20
<212> TYPE: DNA
<213> ORGANISM: Artificial Sequence
<220> FEATURE:
<223> OTHER INFORMATION: Synthetic Oligonucleotide Probe

<400> SEQUENCE: 105
cgctggctca cccctacctg                                                20

<210> SEQ ID NO 106
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 106
ccagcaccat tgttgaagat                                                20

<210> SEQ ID NO 107
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 107
agtctcttgg gcatcgagtt                                                20
```

<210> SEQ ID NO 108
<211> LENGTH: 26
<212> TYPE: DNA
<213> ORGANISM: Artificial Sequence
<220> FEATURE:
<223> OTHER INFORMATION: Synthetic Oligonucleotide Probe

<400> SEQUENCE: 108
ccccagacca agtgtgaata catgct                                  26

<210> SEQ ID NO 109
<211> LENGTH: 24
<212> TYPE: DNA
<213> ORGANISM: Artificial Sequence
<220> FEATURE:
<223> OTHER INFORMATION: Synthetic Oligonucleotide Forward Primer

<400> SEQUENCE: 109
gcactttggg attctttcca ttat                                    24

<210> SEQ ID NO 110
<211> LENGTH: 24
<212> TYPE: DNA
<213> ORGANISM: Artificial Sequence
<220> FEATURE:
<223> OTHER INFORMATION: Synthetic Oligonucleotide Reverse Primer

<400> SEQUENCE: 110
gcatgtaaga agaccctcac tgaa                                    24

<210> SEQ ID NO 111
<211> LENGTH: 29
<212> TYPE: DNA
<213> ORGANISM: Artificial Sequence
<220> FEATURE:
<223> OTHER INFORMATION: Synthetic Oligonucleotide Probe

<400> SEQUENCE: 111
acaacattct cggtgcctgt aacaaagaa                               29

<210> SEQ ID NO 112
<211> LENGTH: 25
<212> TYPE: DNA
<213> ORGANISM: Artificial Sequence
<220> FEATURE:
<223> OTHER INFORMATION: Synthetic Oligonucleotide Reverse Primer

<400> SEQUENCE: 112
ggattgtaga ctgtcaccga aattc                                   25

<210> SEQ ID NO 113
<211> LENGTH: 28
<212> TYPE: DNA
<213> ORGANISM: Artificial Sequence
<220> FEATURE:
<223> OTHER INFORMATION: Synthetic Oligonucleotide Forward Primer

<400> SEQUENCE: 113
ggctattcct cattttctct acaaagtg                                28

<210> SEQ ID NO 114
<211> LENGTH: 30
<212> TYPE: DNA
<213> ORGANISM: Artificial Sequence
<220> FEATURE:

<223> OTHER INFORMATION: Synthetic Oligonucleotide Probe

<400> SEQUENCE: 114
cctccaggag gctaccttct tcatgttcac                                    30

<210> SEQ ID NO 115
<211> LENGTH: 18
<212> TYPE: DNA
<213> ORGANISM: Artificial Sequence
<220> FEATURE:
<223> OTHER INFORMATION: Synthetic Oligonucleotide Forward Primer

<400> SEQUENCE: 115
ccagtggagc gcttccat                                                 18

<210> SEQ ID NO 116
<211> LENGTH: 22
<212> TYPE: DNA
<213> ORGANISM: Artificial Sequence
<220> FEATURE:
<223> OTHER INFORMATION: Synthetic Oligonucleotide Reverse Primer

<400> SEQUENCE: 116
ctctctgggt cgtctgaaac aa                                            22

<210> SEQ ID NO 117
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 117
tcggccactt catcaggacg cag                                           23

<210> SEQ ID NO 118
<211> LENGTH: 26
<212> TYPE: DNA
<213> ORGANISM: Artificial Sequence
<220> FEATURE:
<223> OTHER INFORMATION: Synthetic Oligonucleotide Forward Primer

<400> SEQUENCE: 118
ggataattca gacaacaaca ccatct                                        26

<210> SEQ ID NO 119
<211> LENGTH: 25
<212> TYPE: DNA
<213> ORGANISM: Artificial Sequence
<220> FEATURE:
<223> OTHER INFORMATION: Synthetic Oligonucleotide Reverse Primer

<400> SEQUENCE: 119
tgaagtaatc agccacagac tcaat                                         25

<210> SEQ ID NO 120
<211> LENGTH: 29
<212> TYPE: DNA
<213> ORGANISM: Artificial Sequence
<220> FEATURE:
<223> OTHER INFORMATION: Synthetic Oligonucleotide Probe

<400> SEQUENCE: 120
tcaattgtaa cattctcacc caggccttg                                     29

```
<210> SEQ ID NO 121
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 121
gaagcgcaga tcatgaagaa                                               20

<210> SEQ ID NO 122
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 122
ctcctcagac accactgcat                                               20

<210> SEQ ID NO 123
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 123
ctgaagcacg acaagctggt ccag                                          24

<210> SEQ ID NO 124
<211> LENGTH: 19
<212> TYPE: DNA
<213> ORGANISM: Artificial Sequence
<220> FEATURE:
<223> OTHER INFORMATION: Synthetic Oligonucleotide Forward Primer

<400> SEQUENCE: 124
tcagcagcaa gggcatcat                                                19

<210> SEQ ID NO 125
<211> LENGTH: 23
<212> TYPE: DNA
<213> ORGANISM: Artificial Sequence
<220> FEATURE:
<223> OTHER INFORMATION: Synthetic Oligonucleotide Reverse Primer

<400> SEQUENCE: 125
ggtggttttc ttgagcgtgt act                                           23

<210> SEQ ID NO 126
<211> LENGTH: 19
<212> TYPE: DNA
<213> ORGANISM: Artificial Sequence
<220> FEATURE:
<223> OTHER INFORMATION: Synthetic Oligonucleotide Probe

<400> SEQUENCE: 126
cgcccgcagg cctcatcct                                                19

<210> SEQ ID NO 127
<211> LENGTH: 23
<212> TYPE: DNA
<213> ORGANISM: Artificial Sequence
<220> FEATURE:
<223> OTHER INFORMATION: Synthetic Oligonucleotide Forward Primer
```

<400> SEQUENCE: 127
caaaggagct cactgtggtg tct                                          23

<210> SEQ ID NO 128
<211> LENGTH: 26
<212> TYPE: DNA
<213> ORGANISM: Artificial Sequence
<220> FEATURE:
<223> OTHER INFORMATION: Synthetic Oligonucleotide Reverse Primer

<400> SEQUENCE: 128
gagtcagaat ggcttattca cagatg                                       26

<210> SEQ ID NO 129
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 129
tgttccaacc actgaatctg gacc                                         24

<210> SEQ ID NO 130
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 130
ttgggaaata tttgggcatt                                              20

<210> SEQ ID NO 131
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 131
agaagctagg gtggttgtcc                                              20

<210> SEQ ID NO 132
<211> LENGTH: 26
<212> TYPE: DNA
<213> ORGANISM: Artificial Sequence
<220> FEATURE:
<223> OTHER INFORMATION: Synthetic Oligonucleotide Probe

<400> SEQUENCE: 132
ttgggacatt gtagacttgg ccagac                                       26

<210> SEQ ID NO 133
<211> LENGTH: 19
<212> TYPE: DNA
<213> ORGANISM: Artificial Sequence
<220> FEATURE:
<223> OTHER INFORMATION: Synthetic Oligonucleotide Forward Primer

<400> SEQUENCE: 133
gcatgggaac catcaacca                                               19

<210> SEQ ID NO 134
<211> LENGTH: 21

```
<212> TYPE: DNA
<213> ORGANISM: Artificial Sequence
<220> FEATURE:
<223> OTHER INFORMATION: Synthetic Oligonucleotide Reverse Primer

<400> SEQUENCE: 134
tgaggagttt gccttgattc g                                              21

<210> SEQ ID NO 135
<211> LENGTH: 30
<212> TYPE: DNA
<213> ORGANISM: Artificial Sequence
<220> FEATURE:
<223> OTHER INFORMATION: Synthetic Oligonucleotide Probe

<400> SEQUENCE: 135
ccatggacca acttcactat gtgacagagc                                     30

<210> SEQ ID NO 136
<211> LENGTH: 18
<212> TYPE: DNA
<213> ORGANISM: Artificial Sequence
<220> FEATURE:
<223> OTHER INFORMATION: Synthetic Oligonucleotide Forward Primer

<400> SEQUENCE: 136
ctccgacgtg gctttcca                                                  18

<210> SEQ ID NO 137
<211> LENGTH: 23
<212> TYPE: DNA
<213> ORGANISM: Artificial Sequence
<220> FEATURE:
<223> OTHER INFORMATION: Synthetic Oligonucleotide Reverse Primer

<400> SEQUENCE: 137
cgtaattggc agaattgatg aca                                            23

<210> SEQ ID NO 138
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 138
tggcccacag catctatgga atccc                                          25

<210> SEQ ID NO 139
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 139
ccatctgcat ccatcttgtt                                                20

<210> SEQ ID NO 140
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 140
```

```
ggccaccagg gtattatctg                                          20
```

<210> SEQ ID NO 141
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 141

```
ctccccaccc ttgagaagtg cct                                      23
```

<210> SEQ ID NO 142
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 142

```
aggctgctgg aggtcatctc                                          20
```

<210> SEQ ID NO 143
<211> LENGTH: 19
<212> TYPE: DNA
<213> ORGANISM: Artificial Sequence
<220> FEATURE:
<223> OTHER INFORMATION: Synthetic Oligonucleotide Reverse Primer

<400> SEQUENCE: 143

```
cttcctgcgg ccacagtct                                           19
```

<210> SEQ ID NO 144
<211> LENGTH: 21
<212> TYPE: DNA
<213> ORGANISM: Artificial Sequence
<220> FEATURE:
<223> OTHER INFORMATION: Synthetic Oligonucleotide Probe

<400> SEQUENCE: 144

```
ccagaggccg tttcttggcc g                                        21
```

<210> SEQ ID NO 145
<211> LENGTH: 21
<212> TYPE: DNA
<213> ORGANISM: Artificial Sequence
<220> FEATURE:
<223> OTHER INFORMATION: Synthetic Oligonucleotide Forward Primer

<400> SEQUENCE: 145

```
tccatgatgg ttctgcaggt t                                        21
```

<210> SEQ ID NO 146
<211> LENGTH: 21
<212> TYPE: DNA
<213> ORGANISM: Artificial Sequence
<220> FEATURE:
<223> OTHER INFORMATION: Synthetic Oligonucleotide Reverse Primer

<400> SEQUENCE: 146

```
tgagcagcac catcagtaac g                                        21
```

<210> SEQ ID NO 147
<211> LENGTH: 21
<212> TYPE: DNA
<213> ORGANISM: Artificial Sequence

```
<220> FEATURE:
<223> OTHER INFORMATION: Synthetic Oligonucleotide Probe

<400> SEQUENCE: 147
ccccggacag tggctctgac g                                              21

<210> SEQ ID NO 148
<211> LENGTH: 23
<212> TYPE: DNA
<213> ORGANISM: Artificial Sequence
<220> FEATURE:
<223> OTHER INFORMATION: Synthetic Oligonucleotide Forward Primer

<400> SEQUENCE: 148
aacgactgct actccaagct caa                                            23

<210> SEQ ID NO 149
<211> LENGTH: 22
<212> TYPE: DNA
<213> ORGANISM: Artificial Sequence
<220> FEATURE:
<223> OTHER INFORMATION: Synthetic Oligonucleotide Reverse Primer

<400> SEQUENCE: 149
ggatttccat cttgctcacc tt                                             22

<210> SEQ ID NO 150
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 150
tgcccagcat cccccagaac aa                                             22

<210> SEQ ID NO 151
<211> LENGTH: 21
<212> TYPE: DNA
<213> ORGANISM: Artificial Sequence
<220> FEATURE:
<223> OTHER INFORMATION: Synthetic Oligonucleotide Forward Primer

<400> SEQUENCE: 151
gcatggtagc cgaagatttc a                                              21

<210> SEQ ID NO 152
<211> LENGTH: 30
<212> TYPE: DNA
<213> ORGANISM: Artificial Sequence
<220> FEATURE:
<223> OTHER INFORMATION: Synthetic Oligonucleotide Reverse Primer

<400> SEQUENCE: 152
tttccggtaa tagtctgtct catagatatc                                     30

<210> SEQ ID NO 153
<211> LENGTH: 28
<212> TYPE: DNA
<213> ORGANISM: Artificial Sequence
<220> FEATURE:
<223> OTHER INFORMATION: Synthetic Oligonucleotide Probe

<400> SEQUENCE: 153
cgcgtcatac caaatctccc gattttga                                       28
```

<210> SEQ ID NO 154
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 154
cctgaacctt ccaaagatgg                                          20

<210> SEQ ID NO 155
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 155
accaggcaag tctcctcatt                                          20

<210> SEQ ID NO 156
<211> LENGTH: 27
<212> TYPE: DNA
<213> ORGANISM: Artificial Sequence
<220> FEATURE:
<223> OTHER INFORMATION: Synthetic Oligonucleotide Probe

<400> SEQUENCE: 156
ccagattgga agcatccatc tttttca                                  27

<210> SEQ ID NO 157
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 157
agccatcact ctcagtgcag                                          20

<210> SEQ ID NO 158
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 158
actgcagagt cagggtctcc                                          20

<210> SEQ ID NO 159
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 159
caggtcctat cgtggcccct ga                                       22

<210> SEQ ID NO 160
<211> LENGTH: 20
<212> TYPE: DNA
<213> ORGANISM: Artificial Sequence
<220> FEATURE:
<223> OTHER INFORMATION: Synthetic Oligonucleotide Foward Primer

```
<400> SEQUENCE: 160
ccacagctca ccttctgtca                                              20

<210> SEQ ID NO 161
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 161
cctcagtgcc agtctcttcc                                              20

<210> SEQ ID NO 162
<211> LENGTH: 20
<212> TYPE: DNA
<213> ORGANISM: Artificial Sequence
<220> FEATURE:
<223> OTHER INFORMATION: Synthetic Oligonucleotide Probe

<400> SEQUENCE: 162
tccatcccag ctccagccag                                              20

<210> SEQ ID NO 163
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 163
agagatcgag gctctcaagg                                              20

<210> SEQ ID NO 164
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 164
ggccttttac ttcctcttcg                                              20

<210> SEQ ID NO 165
<211> LENGTH: 27
<212> TYPE: DNA
<213> ORGANISM: Artificial Sequence
<220> FEATURE:
<223> OTHER INFORMATION: Synthetic Oligonucleotide Probe

<400> SEQUENCE: 165
tggttcttct tcatgaagag cagctcc                                      27

<210> SEQ ID NO 166
<211> LENGTH: 23
<212> TYPE: DNA
<213> ORGANISM: Artificial Sequence
<220> FEATURE:
<223> OTHER INFORMATION: Synthetic Oligonucleotide Forward Primer

<400> SEQUENCE: 166
tgagtggaaa agcctgacct atg                                          23

<210> SEQ ID NO 167
```

```
<211> LENGTH: 23
<212> TYPE: DNA
<213> ORGANISM: Artificial Sequence
<220> FEATURE:
<223> OTHER INFORMATION: Synthetic Oligonucleotide Reverse Primer

<400> SEQUENCE: 167
ggactccatc tcttcttggt caa                                             23

<210> SEQ ID NO 168
<211> LENGTH: 27
<212> TYPE: DNA
<213> ORGANISM: Artificial Sequence
<220> FEATURE:
<223> OTHER INFORMATION: Synthetic Oligonucleotide Probe

<400> SEQUENCE: 168
tgaagtcatc agctttgtgc caccacc                                         27

<210> SEQ ID NO 169
<211> LENGTH: 21
<212> TYPE: DNA
<213> ORGANISM: Artificial Sequence
<220> FEATURE:
<223> OTHER INFORMATION: Synthetic Oligonucleotide Forward Primer

<400> SEQUENCE: 169
gacttttgcc cgctaccttt c                                               21

<210> SEQ ID NO 170
<211> LENGTH: 26
<212> TYPE: DNA
<213> ORGANISM: Artificial Sequence
<220> FEATURE:
<223> OTHER INFORMATION: Synthetic Oligonucleotide Reverse Primer

<400> SEQUENCE: 170
gccactaact gcttcagtat gaagag                                          26

<210> SEQ ID NO 171
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 171
acagctcatt gttgtcacgc cgga                                            24

<210> SEQ ID NO 172
<211> LENGTH: 24
<212> TYPE: DNA
<213> ORGANISM: Artificial Sequence
<220> FEATURE:
<223> OTHER INFORMATION: Synthetic Oligonucleotide Forward Primer

<400> SEQUENCE: 172
tgatggtcct atgtgtcaca ttca                                            24

<210> SEQ ID NO 173
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 173
```
tgggacagga aacacaccaa                                             20

<210> SEQ ID NO 174
<211> LENGTH: 30
<212> TYPE: DNA
<213> ORGANISM: Artificial Sequence
<220> FEATURE:
<223> OTHER INFORMATION: Synthetic Oligonucleotide Probe

<400> SEQUENCE: 174
caggtttcat accaacacag gcttcagcac                                  30

<210> SEQ ID NO 175
<211> LENGTH: 19
<212> TYPE: DNA
<213> ORGANISM: Artificial Sequence
<220> FEATURE:
<223> OTHER INFORMATION: Synthetic Oligonucleotide Forward Primer

<400> SEQUENCE: 175
cgctcagcca gatgcaatc                                              19

<210> SEQ ID NO 176
<211> LENGTH: 25
<212> TYPE: DNA
<213> ORGANISM: Artificial Sequence
<220> FEATURE:
<223> OTHER INFORMATION: Synthetic Oligonucleotide Reverse Primer

<400> SEQUENCE: 176
gcactgagat cttcctattg gtgaa                                       25

<210> SEQ ID NO 177
<211> LENGTH: 21
<212> TYPE: DNA
<213> ORGANISM: Artificial Sequence
<220> FEATURE:
<223> OTHER INFORMATION: Synthetic Oligonucleotide Probe

<400> SEQUENCE: 177
tgccccagtc acctgctgtt a                                           21

<210> SEQ ID NO 178
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 178
gtgaaatgaa acgcaccaca                                             20

<210> SEQ ID NO 179
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 179
gaccctgctc acaaccagac                                             20

<210> SEQ ID NO 180
<211> LENGTH: 20
<212> TYPE: DNA

```
<213> ORGANISM: Artificial Sequence
<220> FEATURE:
<223> OTHER INFORMATION: Synthetic Oligonucleotide Probe

<400> SEQUENCE: 180 cagcccttttg gggaagctgg                                              20

<210> SEQ ID NO 181
<211> LENGTH: 19
<212> TYPE: DNA
<213> ORGANISM: Artificial Sequence
<220> FEATURE:
<223> OTHER INFORMATION: Synthetic Oligonucleotide Forward Primer

<400> SEQUENCE: 181
ccaacgcttg ccaaatcct                                                19

<210> SEQ ID NO 182
<211> LENGTH: 24
<212> TYPE: DNA
<213> ORGANISM: Artificial Sequence
<220> FEATURE:
<223> OTHER INFORMATION: Synthetic Oligonucleotide Reverse Primer

<400> SEQUENCE: 182
acggtagtga cagcatcaaa actc                                          24

<210> SEQ ID NO 183
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 183
aaccagctct ctgtgacccc aatt                                          24

<210> SEQ ID NO 184
<211> LENGTH: 21
<212> TYPE: DNA
<213> ORGANISM: Artificial Sequence
<220> FEATURE:
<223> OTHER INFORMATION: Synthetic Oligonucleotide Forward Primer

<400> SEQUENCE: 184
tgattaccat catggctcag a                                             21

<210> SEQ ID NO 185
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 185
cttgtgaaaa tgccatccac                                               20

<210> SEQ ID NO 186
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 186
tcccaattgt cgcttcttct gcag                                          24
```

<210> SEQ ID NO 187
<211> LENGTH: 19
<212> TYPE: DNA
<213> ORGANISM: Artificial Sequence
<220> FEATURE:
<223> OTHER INFORMATION: Synthetic Oligonucleotide Forward Sequence

<400> SEQUENCE: 187
ccgccctcac ctgaagaga                                           19

<210> SEQ ID NO 188
<211> LENGTH: 22
<212> TYPE: DNA
<213> ORGANISM: Artificial Sequence
<220> FEATURE:
<223> OTHER INFORMATION: Synthetic Oligonucleotide Reverse Sequence

<400> SEQUENCE: 188
ggaataagtt agccgcgctt ct                                       22

<210> SEQ ID NO 189
<211> LENGTH: 21
<212> TYPE: DNA
<213> ORGANISM: Artificial Sequence
<220> FEATURE:
<223> OTHER INFORMATION: Synthetic Oligonucleotide Probe

<400> SEQUENCE: 189
cccagtgtcc gccaaggagc g                                        21

<210> SEQ ID NO 190
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 190
ggccaggatc tgtggtggta                                          20

<210> SEQ ID NO 191
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 191
ctccacgtcg tggacattga                                          20

<210> SEQ ID NO 192
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 192
ctctggcctt ccgagaaggt acc                                      23

<210> SEQ ID NO 193
<211> LENGTH: 20
<212> TYPE: DNA
<213> ORGANISM: Artificial Sequence
<220> FEATURE:

<223> OTHER INFORMATION: Synthetic Oligonucleotide Forward Primer

<400> SEQUENCE: 193
ggctgtggct gaggctgtag                                                    20

<210> SEQ ID NO 194
<211> LENGTH: 21
<212> TYPE: DNA
<213> ORGANISM: Artificial Sequence
<220> FEATURE:
<223> OTHER INFORMATION: Synthetic Oligonucleotide Reverse Primer

<400> SEQUENCE: 194
ggagcattcg aggtcaaatc a                                                  21

<210> SEQ ID NO 195
<211> LENGTH: 28
<212> TYPE: DNA
<213> ORGANISM: Artificial Sequence
<220> FEATURE:
<223> OTHER INFORMATION: Synthetic Oligonucleotide Probe

<400> SEQUENCE: 195
ttcccagagt gtctcacctc cagcagag                                           28

<210> SEQ ID NO 196
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 196
gcatcaggct gtcattatgg                                                    20

<210> SEQ ID NO 197
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 197
agtagttgtg ctgcccttcc                                                    20

<210> SEQ ID NO 198
<211> LENGTH: 28
<212> TYPE: DNA
<213> ORGANISM: Artificial Sequence
<220> FEATURE:
<223> OTHER INFORMATION: Synthetic Oligonucleotide Probe

<400> SEQUENCE: 198
tgtccttacc tgtgggagct gtaaggtc                                           28

<210> SEQ ID NO 199
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 199
ctgacacttg ccgcagagaa                                                    20

```
<210> SEQ ID NO 200
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 200
aggtggtcct tggtctggaa                                                20

<210> SEQ ID NO 201
<211> LENGTH: 26
<212> TYPE: DNA
<213> ORGANISM: Artificial Sequence
<220> FEATURE:
<223> OTHER INFORMATION: Synthetic Oligonucleotide Probe

<400> SEQUENCE: 201
ccctttctca cccacctcat ctgcac                                          26

<210> SEQ ID NO 202
<211> LENGTH: 23
<212> TYPE: DNA
<213> ORGANISM: Artificial Sequence
<220> FEATURE:
<223> OTHER INFORMATION: Synthetic Oligonucleotide Forward Primer

<400> SEQUENCE: 202
cgcttgccta actcatactt tcc                                             23

<210> SEQ ID NO 203
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 203
ccattcagac tgcgccactt                                                 20

<210> SEQ ID NO 204
<211> LENGTH: 19
<212> TYPE: DNA
<213> ORGANISM: Artificial Sequence
<220> FEATURE:
<223> OTHER INFORMATION: Synthetic Oligonucleotide Probe

<400> SEQUENCE: 204
tccacgcagc gtggcactg                                                  19

<210> SEQ ID NO 205
<211> LENGTH: 21
<212> TYPE: DNA
<213> ORGANISM: Artificial Sequence
<220> FEATURE:
<223> OTHER INFORMATION: Synthetic Oligonucleotide Forward Primer

<400> SEQUENCE: 205
gcgacagctc ctctagttcc a                                               21

<210> SEQ ID NO 206
<211> LENGTH: 19
<212> TYPE: DNA
<213> ORGANISM: Artificial Sequence
<220> FEATURE:
<223> OTHER INFORMATION: Synthetic Oligonucleotide Probe
```

```
<400> SEQUENCE: 206
ttcccgaagt ctccgcccg                                              19

<210> SEQ ID NO 207
<211> LENGTH: 22
<212> TYPE: DNA
<213> ORGANISM: Artificial Sequence
<220> FEATURE:
<223> OTHER INFORMATION: Synthetic Oligonucleotide Reverse Primer

<400> SEQUENCE: 207
ggaacaccag cttgaatttc ct                                          22

<210> SEQ ID NO 208
<211> LENGTH: 26
<212> TYPE: DNA
<213> ORGANISM: Artificial Sequence
<220> FEATURE:
<223> OTHER INFORMATION: Synthetic Oligonucleotide Forward Primer

<400> SEQUENCE: 208
ggtgtcagat ataaatgtgc aaatgc                                      26

<210> SEQ ID NO 209
<211> LENGTH: 24
<212> TYPE: DNA
<213> ORGANISM: Artificial Sequence
<220> FEATURE:
<223> OTHER INFORMATION: Synthetic Oligonucleotide Reverse Primer

<400> SEQUENCE: 209
ttcgatattg ccagcagcta taaa                                        24

<210> SEQ ID NO 210
<211> LENGTH: 28
<212> TYPE: DNA
<213> ORGANISM: Artificial Sequence
<220> FEATURE:
<223> OTHER INFORMATION: Synthetic Oligonucleotide Probe

<400> SEQUENCE: 210
tgctgtcctg tcggtctcag tacgttca                                    28

<210> SEQ ID NO 211
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 211
tgtggatgct ggattgattt                                             20

<210> SEQ ID NO 212
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 212
aagcagcact tcctggtctt                                             20

<210> SEQ ID NO 213
<211> LENGTH: 25
```

```
<212> TYPE: DNA
<213> ORGANISM: Artificial Sequence
<220> FEATURE:
<223> OTHER INFORMATION: Synthetic Oligonucleotide Probe

<400> SEQUENCE: 213
ccactggtgc agctgctaaa tagca                                      25

<210> SEQ ID NO 214
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 214
agtgggagac acctgacctt                                            20

<210> SEQ ID NO 215
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 215
tgatctgggc attgtactcc                                            20

<210> SEQ ID NO 216
<211> LENGTH: 29
<212> TYPE: DNA
<213> ORGANISM: Artificial Sequence
<220> FEATURE:
<223> OTHER INFORMATION: Synthetic Oligonucleotide Probe

<400> SEQUENCE: 216
ttgatcttct gctcaatctc agcttgaga                                  29

<210> SEQ ID NO 217
<211> LENGTH: 18
<212> TYPE: DNA
<213> ORGANISM: Artificial Sequence
<220> FEATURE:
<223> OTHER INFORMATION: Synthetic Oligonucleotide Forward Primer

<400> SEQUENCE: 217
cccgttcggt ctgaggaa                                              18

<210> SEQ ID NO 218
<211> LENGTH: 22
<212> TYPE: DNA
<213> ORGANISM: Artificial Sequence
<220> FEATURE:
<223> OTHER INFORMATION: Synthetic Oligonucleotide Reverse Primer

<400> SEQUENCE: 218
gagcactcaa ggtagccaaa gg                                         22

<210> SEQ ID NO 219
<211> LENGTH: 19
<212> TYPE: DNA
<213> ORGANISM: Artificial Sequence
<220> FEATURE:
<223> OTHER INFORMATION: Synthetic Oligonucleotide Probe

<400> SEQUENCE: 219
```
tccggttcgc catgtcccg                                               19

<210> SEQ ID NO 220
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 220
aacagagaca ttgccaacca                                              20

<210> SEQ ID NO 221
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 221
gtgatttgcc caggaagttt                                              20

<210> SEQ ID NO 222
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 222
ttggatctgc ttgctgtcca aacc                                         24

<210> SEQ ID NO 223
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 223
cgcgagcccc tcattataca                                              20

<210> SEQ ID NO 224
<211> LENGTH: 19
<212> TYPE: DNA
<213> ORGANISM: Artificial Sequence
<220> FEATURE:
<223> OTHER INFORMATION: Synthetic Oligonucleotide Reverse Primer

<400> SEQUENCE: 224
cactcgccgt tgacatcct                                               19

<210> SEQ ID NO 225
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 225
ctccccacag cgcatcgagg aa                                           22

<210> SEQ ID NO 226
<211> LENGTH: 23
<212> TYPE: DNA
<213> ORGANISM: Artificial Sequence

```
<220> FEATURE:
<223> OTHER INFORMATION: Synthetic Oligonucleotide Forward Primer

<400> SEQUENCE: 226
cagtggagac cagttgggta gtg                                           23

<210> SEQ ID NO 227
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 227
ccttgaagag cgtcccatca                                               20

<210> SEQ ID NO 228
<211> LENGTH: 28
<212> TYPE: DNA
<213> ORGANISM: Artificial Sequence
<220> FEATURE:
<223> OTHER INFORMATION: Synthetic Oligonucleotide Probe

<400> SEQUENCE: 228
cacacatgca gagcttgtag cgtaccca                                      28

<210> SEQ ID NO 229
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 229
gggctcagct ttcagaagtg                                               20

<210> SEQ ID NO 230
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 230
acatgttcag ctggtccaca                                               20

<210> SEQ ID NO 231
<211> LENGTH: 25
<212> TYPE: DNA
<213> ORGANISM: Artificial Sequence
<220> FEATURE:
<223> OTHER INFORMATION: Synthetic Oligonucleotide Probe

<400> SEQUENCE: 231
tggcagtttt cttctgtcac caaaa                                         25

<210> SEQ ID NO 232
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 232
tcacatgcca ctttggtgtt                                               20
```

<210> SEQ ID NO 233
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 233
cttgcaggaa gcggctatac                                          20

<210> SEQ ID NO 234
<211> LENGTH: 22
<212> TYPE: DNA
<213> ORGANISM: Artificial Sequence
<220> FEATURE:
<223> OTHER INFORMATION: Synthetic Oligonucleotide Probe

<400> SEQUENCE: 234
tcctgggaga gattgaccag ca                                       22

<210> SEQ ID NO 235
<211> LENGTH: 19
<212> TYPE: DNA
<213> ORGANISM: Artificial Sequence
<220> FEATURE:
<223> OTHER INFORMATION: Synthetic Oligonucleotide Forward Primer

<400> SEQUENCE: 235
gcccgaaacg ccgaatata                                           19

<210> SEQ ID NO 236
<211> LENGTH: 23
<212> TYPE: DNA
<213> ORGANISM: Artificial Sequence
<220> FEATURE:
<223> OTHER INFORMATION: Synthetic Oligonucleotide Reverse Primer

<400> SEQUENCE: 236
cgtggctctc ttatcctcat gat                                      23

<210> SEQ ID NO 237
<211> LENGTH: 21
<212> TYPE: DNA
<213> ORGANISM: Artificial Sequence
<220> FEATURE:
<223> OTHER INFORMATION: Synthetic Oligonucleotide Probe

<400> SEQUENCE: 237
taccgcagca aaccgcttgg g                                        21

<210> SEQ ID NO 238
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 238
gccgggaaga ccgtaattgt                                          20

<210> SEQ ID NO 239
<211> LENGTH: 18
<212> TYPE: DNA
<213> ORGANISM: Artificial Sequence
<220> FEATURE:
<223> OTHER INFORMATION: Synthetic Oligonucleotide Reverse Primer

```
<400> SEQUENCE: 239
cagcggcacc aggttcag                                              18

<210> SEQ ID NO 240
<211> LENGTH: 26
<212> TYPE: DNA
<213> ORGANISM: Artificial Sequence
<220> FEATURE:
<223> OTHER INFORMATION: Synthetic Oligonucleotide Probe

<400> SEQUENCE: 240
caaatggctt cctctggaag gtccca                                     26

<210> SEQ ID NO 241
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 241
tgctgttgct gagtctgttg                                            20

<210> SEQ ID NO 242
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 242
cttgcctggc ttcacagata                                            20

<210> SEQ ID NO 243
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 243
ccagtcccca gaagaccatg tctg                                       24

<210> SEQ ID NO 244
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 244
tgtggtgagg aaggagtcag                                            20

<210> SEQ ID NO 245
<211> LENGTH: 18
<212> TYPE: DNA
<213> ORGANISM: Artificial Sequence
<220> FEATURE:
<223> OTHER INFORMATION: Synthetic Oligonucleotide Reverse Primer

<400> SEQUENCE: 245
cccagagagt gggtcagc                                              18

<210> SEQ ID NO 246
```

```
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 246
ctgtgactgt ctccagggct tcca                                           24

<210> SEQ ID NO 247
<211> LENGTH: 21
<212> TYPE: DNA
<213> ORGANISM: Artificial Sequence
<220> FEATURE:
<223> OTHER INFORMATION: Synthetic Oligonucleotide Forward Primer

<400> SEQUENCE: 247
tggcttcagg agctgaatac c                                              21

<210> SEQ ID NO 248
<211> LENGTH: 24
<212> TYPE: DNA
<213> ORGANISM: Artificial Sequence
<220> FEATURE:
<223> OTHER INFORMATION: Synthetic Oligonucleotide Reverse Primer

<400> SEQUENCE: 248
tgctgtcgtg atgagaaaat agtg                                           24

<210> SEQ ID NO 249
<211> LENGTH: 26
<212> TYPE: DNA
<213> ORGANISM: Artificial Sequence
<220> FEATURE:
<223> OTHER INFORMATION: Synthetic Oligonucleotide Probe

<400> SEQUENCE: 249
caggcacaca caggtgggac acaaat                                         26

<210> SEQ ID NO 250
<211> LENGTH: 25
<212> TYPE: DNA
<213> ORGANISM: Artificial Sequence
<220> FEATURE:
<223> OTHER INFORMATION: Synthetic Oligonucleotide Forward Primer

<400> SEQUENCE: 250
gtatcaggac cacatgcagt acatc                                          25

<210> SEQ ID NO 251
<211> LENGTH: 22
<212> TYPE: DNA
<213> ORGANISM: Artificial Sequence
<220> FEATURE:
<223> OTHER INFORMATION: Synthetic Oligonucleotide Reverse Primer

<400> SEQUENCE: 251
tgtcggaatt gatactggca tt                                             22

<210> SEQ ID NO 252
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 252
```
ttgatgcctg tcttcgcgcc ttct                                                  24

<210> SEQ ID NO 253
<211> LENGTH: 20
<212> TYPE: DNA
<213> ORGANISM: Artificial Sequence
<220> FEATURE:
<223> OTHER INFORMATION: Synthetic Oligonucleotide Forward Primer

<400> SEQUENCE: 253
tttccaaaca tcagcgagtc                                                       20

<210> SEQ ID NO 254
<211> LENGTH: 20
<212> TYPE: DNA
<213> ORGANISM: Artificial Sequence
<220> FEATURE:
<223> OTHER INFORMATION: Synthetic Oligonucleotide Reverse Primer

<400> SEQUENCE: 254
aacaggagcg cttgaaagtt                                                       20

<210> SEQ ID NO 255
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 255
acggtgcttc tccctctcca gtg                                                   23

<210> SEQ ID NO 256
<211> LENGTH: 78
<212> TYPE: DNA
<213> ORGANISM: Artificial Sequence
<220> FEATURE:
<223> OTHER INFORMATION: Amplicon

<400> SEQUENCE: 256
cgttccgatc tctatactg catcccaggc atgcctacag caccctgatg tcgcagccta           60
taaggccaac agggacct                                                         78

<210> SEQ ID NO 257
<211> LENGTH: 76
<212> TYPE: DNA
<213> ORGANISM: Artificial Sequence
<220> FEATURE:
<223> OTHER INFORMATION: Amplicon

<400> SEQUENCE: 257
tgcagactgt accatgctga ccattgccca tcgcctgcac acggttctag gctccgatag           60
gattatggtg ctggcc                                                           76

<210> SEQ ID NO 258
<211> LENGTH: 78
<212> TYPE: DNA
<213> ORGANISM: Artificial Sequence
<220> FEATURE:
<223> OTHER INFORMATION: Amplicon

<400> SEQUENCE: 258
ctgcatgtga ttgaataaga aacaagaaag tgaccacacc aaagcctccc tggctggtgt           60

-continued acagggatca ggtccaca    78

<210> SEQ ID NO 259
<211> LENGTH: 68
<212> TYPE: DNA
<213> ORGANISM: Artificial Sequence
<220> FEATURE:
<223> OTHER INFORMATION: Amplicon

<400> SEQUENCE: 259
acgaattgtc ggtgaggtct caggatacca cagtcctgga gaccctatcc aatgatttca    60
gcatggac    68

<210> SEQ ID NO 260
<211> LENGTH: 71
<212> TYPE: DNA
<213> ORGANISM: Artificial Sequence
<220> FEATURE:
<223> OTHER INFORMATION: Amplicon

<400> SEQUENCE: 260
cgcttctatg gcgctgagat tgtgtcagcc ctggactacc tgcactcgga gaagaacgtg    60
gtgtaccggg a    71

<210> SEQ ID NO 261
<211> LENGTH: 71
<212> TYPE: DNA
<213> ORGANISM: Artificial Sequence
<220> FEATURE:
<223> OTHER INFORMATION: Amplicon

<400> SEQUENCE: 261
tcctgccacc cttcaaacct caggtcacgt ccgaggtcga cacaaggtac ttcgatgatg    60
aatttaccgc c    71

<210> SEQ ID NO 262
<211> LENGTH: 69
<212> TYPE: DNA
<213> ORGANISM: Artificial Sequence
<220> FEATURE:
<223> OTHER INFORMATION: Amplicon

<400> SEQUENCE: 262
ggacagcagg aatgtgtttc tccatacagg tcacggggag ccaatggttc agaaacaaat    60
cgagtgggt    69

<210> SEQ ID NO 263
<211> LENGTH: 73
<212> TYPE: DNA
<213> ORGANISM: Artificial Sequence
<220> FEATURE:
<223> OTHER INFORMATION: Amplicon

<400> SEQUENCE: 263
gggtcaggtg cctcgagatc gggcttgggc ccagagcatg ttccagatcc cagagtttga    60
gccgagtgag cag    73

<210> SEQ ID NO 264
<211> LENGTH: 81
<212> TYPE: DNA
<213> ORGANISM: Artificial Sequence
<220> FEATURE:
<223> OTHER INFORMATION: Amplicon

<400> SEQUENCE: 264
cgttgtcagc acttggaata caagatggtt gccgggtcat gttaattggg aaaaagaaca    60
gtccacagga agaggttgaa c    81

<210> SEQ ID NO 265
<211> LENGTH: 83
<212> TYPE: DNA
<213> ORGANISM: Artificial Sequence
<220> FEATURE:
<223> OTHER INFORMATION: Amplicon

<400> SEQUENCE: 265
cctggagggt cctgtacaat ctcatcatgg gactcctgcc cttacccagg ggccacagag    60
cccccgagat ggagcccaat tag    83

<210> SEQ ID NO 266
<211> LENGTH: 73
<212> TYPE: DNA
<213> ORGANISM: Artificial Sequence
<220> FEATURE:
<223> OTHER INFORMATION: Amplicon

<400> SEQUENCE: 266
cagatggacc tagtacccac tgagatttcc acgccgaagg acagcgatgg gaaaaatgcc    60
cttaaatcat agg    73

<210> SEQ ID NO 267
<211> LENGTH: 69
<212> TYPE: DNA
<213> ORGANISM: Artificial Sequence
<220> FEATURE:
<223> OTHER INFORMATION: Amplicon

<400> SEQUENCE: 267
gcatgttcgt ggcctctaag atgaaggaga ccatcccct gacggccgag aagctgtgca    60
tctacaccg    69

<210> SEQ ID NO 268
<211> LENGTH: 81
<212> TYPE: DNA
<213> ORGANISM: Artificial Sequence
<220> FEATURE:
<223> OTHER INFORMATION: Amplicon

<400> SEQUENCE: 268
cgtcaggacc caccatgtct gccccatcac gcggccgaga catggcttgg ccacagctct    60
tgaggatgtc accaattaac c    81

<210> SEQ ID NO 269
<211> LENGTH: 75
<212> TYPE: DNA
<213> ORGANISM: Artificial Sequence
<220> FEATURE:
<223> OTHER INFORMATION: Amplicon

<400> SEQUENCE: 269
tgtatttcaa gacctctgtg cacttattta tgaacctgcc ctgctcccac agaacacagc    60
aattcctcag gctaa    75

<210> SEQ ID NO 270

-continued

```
<211> LENGTH: 65
<212> TYPE: DNA
<213> ORGANISM: Artificial Sequence
<220> FEATURE:
<223> OTHER INFORMATION: Amplicon

<400> SEQUENCE: 270
agatgaagtg aaggcgcttt tcaccgcgg ccatcctgca ggcacagttg ccgattacag    60
aggca                                                              65

<210> SEQ ID NO 271
<211> LENGTH: 64
<212> TYPE: DNA
<213> ORGANISM: Artificial Sequence
<220> FEATURE:
<223> OTHER INFORMATION: Amplicon

<400> SEQUENCE: 271
gggcgtggaa cagtttatct cagacatctg ccccaagaag gacgtactcg aaaccttcac   60
cgtg                                                               64

<210> SEQ ID NO 272
<211> LENGTH: 68
<212> TYPE: DNA
<213> ORGANISM: Artificial Sequence
<220> FEATURE:
<223> OTHER INFORMATION: Amplicon

<400> SEQUENCE: 272
tggattggag ttctgggaat gtactggccg tggcactgga caacagtgtg tacctgtgga   60
gtgcaagc                                                           68

<210> SEQ ID NO 273
<211> LENGTH: 85
<212> TYPE: DNA
<213> ORGANISM: Artificial Sequence
<220> FEATURE:
<223> OTHER INFORMATION: Amplicon

<400> SEQUENCE: 273
aaacgagcag tttgccatca gacgcttcca gtctatgccg gtgaggctgc tgggccacag   60
ccccgtgctt cggaacatca ccaac                                        85

<210> SEQ ID NO 274
<211> LENGTH: 77
<212> TYPE: DNA
<213> ORGANISM: Artificial Sequence
<220> FEATURE:
<223> OTHER INFORMATION: Amplicon

<400> SEQUENCE: 274
tgacaatcag cacacctgca ttcaccgctc ggaagagggc ctgagctgca tgaataagga   60
tcacggctgt agtcaca                                                 77

<210> SEQ ID NO 275
<211> LENGTH: 76
<212> TYPE: DNA
<213> ORGANISM: Artificial Sequence
<220> FEATURE:
<223> OTHER INFORMATION: Amplicon

<400> SEQUENCE: 275
ctgaaggagc tccaagacct cgctctccaa ggcgccaagg agagggcaca tcagcagaag   60
```

```
aaacacagcg gttttg                                              76
```

<210> SEQ ID NO 276
<211> LENGTH: 68
<212> TYPE: DNA
<213> ORGANISM: Artificial Sequence
<220> FEATURE:
<223> OTHER INFORMATION: Amplicon

<400> SEQUENCE: 276

```
gtggccatcc agctgacctt cctgcgcctg atgtccaccg aggcctccca gaacatcacc   60
taccactg                                                           68
```

<210> SEQ ID NO 277
<211> LENGTH: 80
<212> TYPE: DNA
<213> ORGANISM: Artificial Sequence
<220> FEATURE:
<223> OTHER INFORMATION: Amplicon

<400> SEQUENCE: 277

```
cagccaagaa ctggtatagg agctccaagg acaagaaaca cgtctggcta ggagaaacta   60
tcaatgctgg cagccagttt                                              80
```

<210> SEQ ID NO 278
<211> LENGTH: 81
<212> TYPE: DNA
<213> ORGANISM: Artificial Sequence
<220> FEATURE:
<223> OTHER INFORMATION: Amplicon

<400> SEQUENCE: 278

```
cgacagttgc gatgaaagtt ctaatctctt ccctcctcct gttgctgcca ctaatgctga   60
tgtccatggt ctctagcagc c                                            81
```

<210> SEQ ID NO 279
<211> LENGTH: 67
<212> TYPE: DNA
<213> ORGANISM: Artificial Sequence
<220> FEATURE:
<223> OTHER INFORMATION: Amplicon

<400> SEQUENCE: 279

```
aacttcaagg tcggagaagg ctttgaggag gagaccgtgg acggacgcaa gtgcaggagt   60
ttagcca                                                            67
```

<210> SEQ ID NO 280
<211> LENGTH: 76
<212> TYPE: DNA
<213> ORGANISM: Artificial Sequence
<220> FEATURE:
<223> OTHER INFORMATION: Amplicon

<400> SEQUENCE: 280

```
gtgctacgcc accctgttcg gacccaaagg cgtgaacatc ggggcgcgg gctcctacat   60 ctacgagaag cccctg                                                  76
```

<210> SEQ ID NO 281
<211> LENGTH: 77
<212> TYPE: DNA
<213> ORGANISM: Artificial Sequence
<220> FEATURE:

<223> OTHER INFORMATION: Amplicon

<400> SEQUENCE: 281
ggtgcctact ccattgtggc gggcgtgttt gtgtgcctgc tggagtaccc ccgggggaag    60
aggaagaagg gctccac                                                  77

<210> SEQ ID NO 282
<211> LENGTH: 78
<212> TYPE: DNA
<213> ORGANISM: Artificial Sequence
<220> FEATURE:
<223> OTHER INFORMATION: Amplicon

<400> SEQUENCE: 282
gggagaacgg gatcaatagg atcggaaacc tgctggtgcc caatgagaat tactgcaagt    60
ttgaggactg gctgatgc                                                 78

<210> SEQ ID NO 283
<211> LENGTH: 68
<212> TYPE: DNA
<213> ORGANISM: Artificial Sequence
<220> FEATURE:
<223> OTHER INFORMATION: Amplicon

<400> SEQUENCE: 283
tccaattcca gcatcactgt ggagaaaagc tgtttgtctc cccagcatac tttatcgcct    60
tcactgcc                                                            68

<210> SEQ ID NO 284
<211> LENGTH: 83
<212> TYPE: DNA
<213> ORGANISM: Artificial Sequence
<220> FEATURE:
<223> OTHER INFORMATION: Amplicon

<400> SEQUENCE: 284
tgcacagagg gtgtgggtta caccaatgct tccaacaatt tgtttgcttg cctcccatgt    60
acagcttgta aatcagatga aga                                           83

<210> SEQ ID NO 285
<211> LENGTH: 75
<212> TYPE: DNA
<213> ORGANISM: Artificial Sequence
<220> FEATURE:
<223> OTHER INFORMATION: Amplicon

<400> SEQUENCE: 285
actccctcta cccttgagca agggcagggg tccctgagct gttcttctgc cccatactga    60
aggaactgag gcctg                                                    75

<210> SEQ ID NO 286
<211> LENGTH: 76
<212> TYPE: DNA
<213> ORGANISM: Artificial Sequence
<220> FEATURE:
<223> OTHER INFORMATION: Amplicon

<400> SEQUENCE: 286
tggtccatcg ccagttatca catctgtatg cggaacctca aaagagtccc tggtgtgaag    60
caagatcgct agaaca                                                   76

<210> SEQ ID NO 287
<211> LENGTH: 81
<212> TYPE: DNA
<213> ORGANISM: Artificial Sequence
<220> FEATURE:
<223> OTHER INFORMATION: Amplicon

<400> SEQUENCE: 287

```
cggttatgtc atgccagata cacacctcaa aggtactccc tcctcccggg aaggcaccct    60
ttcttcagtg ggtctcagtt c                                              81
```

<210> SEQ ID NO 288
<211> LENGTH: 86
<212> TYPE: DNA
<213> ORGANISM: Artificial Sequence
<220> FEATURE:
<223> OTHER INFORMATION: Amplicon

<400> SEQUENCE: 288

```
tggctcttaa tcagtttcgt tacctgcctc tggagaattt acgcattatt cgtgggacaa    60
aactttatga ggatcgatat gccttg                                         86
```

<210> SEQ ID NO 289
<211> LENGTH: 67
<212> TYPE: DNA
<213> ORGANISM: Artificial Sequence
<220> FEATURE:
<223> OTHER INFORMATION: Amplicon

<400> SEQUENCE: 289

```
gtccaggtgg atgtgaaaga tccccagcag gccctcaagg agctggctaa gatgtgtatc    60
ctggccg                                                              67
```

<210> SEQ ID NO 290
<211> LENGTH: 67
<212> TYPE: DNA
<213> ORGANISM: Artificial Sequence
<220> FEATURE:
<223> OTHER INFORMATION: Amplicon

<400> SEQUENCE: 290

```
acggatcaca gtggaggaag cgctggctca cccctacctg gagcagtact atgacccgac    60
ggatgag                                                              67
```

<210> SEQ ID NO 291
<211> LENGTH: 67
<212> TYPE: DNA
<213> ORGANISM: Artificial Sequence
<220> FEATURE:
<223> OTHER INFORMATION: Amplicon

<400> SEQUENCE: 291

```
ccagcaccat tgttgaagat ccccagacca agtgtgaata catgctcaac tcgatgccca    60
agagact                                                              67
```

<210> SEQ ID NO 292
<211> LENGTH: 80
<212> TYPE: DNA
<213> ORGANISM: Artificial Sequence
<220> FEATURE:
<223> OTHER INFORMATION: Amplicon

<400> SEQUENCE: 292
gcactttggg attctttcca ttatgattct tgttacagg caccgagaat gttgtattca    60
gtgagggtct tcttacatgc                                              80

<210> SEQ ID NO 293
<211> LENGTH: 90
<212> TYPE: DNA
<213> ORGANISM: Artificial Sequence
<220> FEATURE:
<223> OTHER INFORMATION: Amplicon

<400> SEQUENCE: 293
ggctattcct cattttctct acaaagtggc ctcagtgaac atgaagaagg tagcctcctg    60
gaggagaatt tcggtgacag tctacaatcc                                   90

<210> SEQ ID NO 294
<211> LENGTH: 67
<212> TYPE: DNA
<213> ORGANISM: Artificial Sequence
<220> FEATURE:
<223> OTHER INFORMATION: Amplicon

<400> SEQUENCE: 294
ccagtggagc gcttccatga cctgcgtcct gatgaagtgg ccgatttgtt tcagacgacc    60
cagagag                                                            67

<210> SEQ ID NO 295
<211> LENGTH: 80
<212> TYPE: DNA
<213> ORGANISM: Artificial Sequence
<220> FEATURE:
<223> OTHER INFORMATION: Amplicon

<400> SEQUENCE: 295
ggataattca gacaacaaca ccatctttgt gcaaggcctg ggtgagaatg ttacaattga    60
gtctgtggct gattacttca                                              80

<210> SEQ ID NO 296
<211> LENGTH: 69
<212> TYPE: DNA
<213> ORGANISM: Artificial Sequence
<220> FEATURE:
<223> OTHER INFORMATION: Amplicon

<400> SEQUENCE: 296
gaagcgcaga tcatgaagaa gctgaagcac gacaagctgg tccagctcta tgcagtggtg    60
tctgaggag                                                          69

<210> SEQ ID NO 297
<211> LENGTH: 68
<212> TYPE: DNA
<213> ORGANISM: Artificial Sequence
<220> FEATURE:
<223> OTHER INFORMATION: Amplicon

<400> SEQUENCE: 297
tcagcagcaa gggcatcatg gaggaggatg aggcctgcgg gcgccagtac acgctcaaga    60
aaaccacc                                                           68

<210> SEQ ID NO 298
<211> LENGTH: 75
<212> TYPE: DNA
<213> ORGANISM: Artificial Sequence

```
<220> FEATURE:
<223> OTHER INFORMATION: Amplicon

<400> SEQUENCE: 298
caaaggagct cactgtggtg tctgtgttcc aaccactgaa tctggacccc atctgtgaat    60
aagccattct gactc                                                    75

<210> SEQ ID NO 299
<211> LENGTH: 73
<212> TYPE: DNA
<213> ORGANISM: Artificial Sequence
<220> FEATURE:
<223> OTHER INFORMATION: Amplicon

<400> SEQUENCE: 299
ttgggaaata tttgggcatt ggtctggcca agtctacaat gtcccaatat caaggacaac    60
caccctagct tct                                                      73

<210> SEQ ID NO 300
<211> LENGTH: 83
<212> TYPE: DNA
<213> ORGANISM: Artificial Sequence
<220> FEATURE:
<223> OTHER INFORMATION: Amplicon

<400> SEQUENCE: 300
gcatgggaac catcaaccag caggccatgg accaacttca ctatgtgaca gagctgacag    60
atcgaatcaa ggcaaactcc tca                                           83

<210> SEQ ID NO 301
<211> LENGTH: 70
<212> TYPE: DNA
<213> ORGANISM: Artificial Sequence
<220> FEATURE:
<223> OTHER INFORMATION: Amplicon

<400> SEQUENCE: 301
ctccgacgtg gctttccagt ggcccacagc atctatggaa tcccatctgt catcaattct    60
gccaattacg                                                          70

<210> SEQ ID NO 302
<211> LENGTH: 67
<212> TYPE: DNA
<213> ORGANISM: Artificial Sequence
<220> FEATURE:
<223> OTHER INFORMATION: Amplicon

<400> SEQUENCE: 302
ccatctgcat ccatcttgtt tgggctcccc acccttgaga agtgcctcag ataatacct    60 ggtggcc                                                             67

<210> SEQ ID NO 303
<211> LENGTH: 84
<212> TYPE: DNA
<213> ORGANISM: Artificial Sequence
<220> FEATURE:
<223> OTHER INFORMATION: Amplicon

<400> SEQUENCE: 303
aggctgctgg aggtcatctc cgtgtgtgat tgcccagag gccgtttctt ggccgccatc    60
tgccaagact gtggccgcag gaag                                          84
```

<210> SEQ ID NO 304
<211> LENGTH: 73
<212> TYPE: DNA
<213> ORGANISM: Artificial Sequence
<220> FEATURE:
<223> OTHER INFORMATION: Amplicon

<400> SEQUENCE: 304
tccatgatgg ttctgcaggt ttctgcggcc ccccggacag tggctctgac ggcgttactg    60
atggtgctgc tca    73

<210> SEQ ID NO 305
<211> LENGTH: 76
<212> TYPE: DNA
<213> ORGANISM: Artificial Sequence
<220> FEATURE:
<223> OTHER INFORMATION: Amplicon

<400> SEQUENCE: 305
aacgactgct actccaagct caaggagctg gtgcccagca tcccccagaa caagaaggtg    60
agcaagatgg aaatcc    76

<210> SEQ ID NO 306
<211> LENGTH: 83
<212> TYPE: DNA
<213> ORGANISM: Artificial Sequence
<220> FEATURE:
<223> OTHER INFORMATION: Amplicon

<400> SEQUENCE: 306
gcatggtagc cgaagatttc acagtcaaaa tcggagattt tggtatgacg cgagatatct    60
atgagacaga ctattaccgg aaa    83

<210> SEQ ID NO 307
<211> LENGTH: 72
<212> TYPE: DNA
<213> ORGANISM: Artificial Sequence
<220> FEATURE:
<223> OTHER INFORMATION: Amplicon

<400> SEQUENCE: 307
cctgaacctt ccaaagatgg ctgaaaaaga tggatgcttc caatctggat tcaatgagga    60
gacttgcctg gt    72

<210> SEQ ID NO 308
<211> LENGTH: 63
<212> TYPE: DNA
<213> ORGANISM: Artificial Sequence
<220> FEATURE:
<223> OTHER INFORMATION: Amplicon

<400> SEQUENCE: 308
agccatcact ctcagtgcag ccaggtccta tcgtggcccc tgaggagacc ctgactctgc    60
agt    63

<210> SEQ ID NO 309
<211> LENGTH: 74
<212> TYPE: DNA
<213> ORGANISM: Artificial Sequence
<220> FEATURE:
<223> OTHER INFORMATION: Amplicon

<400> SEQUENCE: 309

```
ccacagctca ccttctgtca ggtgtccatc ccagctccag ccagctccca gagaggaaga    60
gactggcact gagg                                                      74

<210> SEQ ID NO 310
<211> LENGTH: 68
<212> TYPE: DNA
<213> ORGANISM: Artificial Sequence
<220> FEATURE:
<223> OTHER INFORMATION: Amplicon

<400> SEQUENCE: 310
agagatcgag gctctcaagg aggagctgct cttcatgaag aagaaccacg aagaggaagt    60
aaaaggcc                                                             68

<210> SEQ ID NO 311
<211> LENGTH: 76
<212> TYPE: DNA
<213> ORGANISM: Artificial Sequence
<220> FEATURE:
<223> OTHER INFORMATION: Amplicon

<400> SEQUENCE: 311
tgagtggaaa agcctgacct atgatgaagt catcagcttt gtgccaccac cccttgacca    60
agaagagatg gagtcc                                                    76

<210> SEQ ID NO 312
<211> LENGTH: 75
<212> TYPE: DNA
<213> ORGANISM: Artificial Sequence
<220> FEATURE:
<223> OTHER INFORMATION: Amplicon

<400> SEQUENCE: 312
gacttttgcc cgctaccttt cattccggcg tgacaacaat gagctgttgc tcttcatact    60
gaagcagtta gtggc                                                     75

<210> SEQ ID NO 313
<211> LENGTH: 82
<212> TYPE: DNA
<213> ORGANISM: Artificial Sequence
<220> FEATURE:
<223> OTHER INFORMATION: Amplicon

<400> SEQUENCE: 313
tgatggtcct atgtgtcaca ttcatcacag gtttcatacc aacacaggct tcagcacttc    60
ctttggtgtg tttcctgtcc ca                                             82

<210> SEQ ID NO 314
<211> LENGTH: 71
<212> TYPE: DNA
<213> ORGANISM: Artificial Sequence
<220> FEATURE:
<223> OTHER INFORMATION: Amplicon

<400> SEQUENCE: 314
cgctcagcca gatgcaatca atgccccagt cacctgctgt tataacttca ccaataggaa    60
gatctcagtg c                                                         71

<210> SEQ ID NO 315
<211> LENGTH: 69
<212> TYPE: DNA
```

```
<213> ORGANISM: Artificial Sequence
<220> FEATURE:
<223> OTHER INFORMATION: Amplicon

<400> SEQUENCE: 315
gtgaaatgaa acgcaccaca ctggacagcc ctttggggaa gctggagctg tctggttgtg    60
agcagggtc                                                            69

<210> SEQ ID NO 316
<211> LENGTH: 78
<212> TYPE: DNA
<213> ORGANISM: Artificial Sequence
<220> FEATURE:
<223> OTHER INFORMATION: Amplicon

<400> SEQUENCE: 316
ccaacgcttg ccaaatcctg acaattcaga accagctctc tgtgacccca atttgagttt    60
tgatgctgtc actaccgt                                                  78

<210> SEQ ID NO 317
<211> LENGTH: 82
<212> TYPE: DNA
<213> ORGANISM: Artificial Sequence
<220> FEATURE:
<223> OTHER INFORMATION: Amplicon

<400> SEQUENCE: 317
tgattaccat catggctcag attggctcct atgttcctgc agaagaagcg acaattggga    60
ttgtggatgg cattttcaca ag                                             82

<210> SEQ ID NO 318
<211> LENGTH: 77
<212> TYPE: DNA
<213> ORGANISM: Artificial Sequence
<220> FEATURE:
<223> OTHER INFORMATION: Amplicon

<400> SEQUENCE: 318
ccgccctcac ctgaagagaa acgcgctcct tggcggacac tgggggagga gaggaagaag    60
cgcggctaac ttattcc                                                   77

<210> SEQ ID NO 319
<211> LENGTH: 71
<212> TYPE: DNA
<213> ORGANISM: Artificial Sequence
<220> FEATURE:
<223> OTHER INFORMATION: Amplicon

<400> SEQUENCE: 319
ggccaggatc tgtggtggta caattgactc tggccttccg agaaggtacc atcaatgtcc    60
acgacgtgga g                                                         71

<210> SEQ ID NO 320
<211> LENGTH: 73
<212> TYPE: DNA
<213> ORGANISM: Artificial Sequence
<220> FEATURE:
<223> OTHER INFORMATION: Amplicon

<400> SEQUENCE: 320
ggctgtggct gaggctgtag catctctgct ggaggtgaga cactctggga actgatttga    60
cctcgaatgc tcc                                                       73
```

<210> SEQ ID NO 321
<211> LENGTH: 85
<212> TYPE: DNA
<213> ORGANISM: Artificial Sequence
<220> FEATURE:
<223> OTHER INFORMATION: Amplicon

<400> SEQUENCE: 321
gcatcaggct gtcattatgg tgtccttacc tgtgggagct gtaaggtctt ctttaagagg    60
gcaatggaag ggcagcacaa ctact                                          85

<210> SEQ ID NO 322
<211> LENGTH: 68
<212> TYPE: DNA
<213> ORGANISM: Artificial Sequence
<220> FEATURE:
<223> OTHER INFORMATION: Amplicon

<400> SEQUENCE: 322
ctgacacttg ccgcagagaa tccctttctc acccacctca tctgcacctt ccagaccaag    60
gaccacct                                                             68

<210> SEQ ID NO 323
<211> LENGTH: 81
<212> TYPE: DNA
<213> ORGANISM: Artificial Sequence
<220> FEATURE:
<223> OTHER INFORMATION: Amplicon

<400> SEQUENCE: 323
cgcttgccta actcatactt tcccgttgac acttgatcca cgcagcgtgg cactgggacg    60
taagtggcgc agtctgaatg g                                              81

<210> SEQ ID NO 324
<211> LENGTH: 78
<212> TYPE: DNA
<213> ORGANISM: Artificial Sequence
<220> FEATURE:
<223> OTHER INFORMATION: Amplicon

<400> SEQUENCE: 324
gcgacagctc ctctagttcc accatgtccg cgggcggaga cttcgggaat ccgctgagga    60
aattcaagct ggtgttcc                                                  78

<210> SEQ ID NO 325
<211> LENGTH: 84
<212> TYPE: DNA
<213> ORGANISM: Artificial Sequence
<220> FEATURE:
<223> OTHER INFORMATION: Amplicon

<400> SEQUENCE: 325
ggtgtcagat ataaatgtgc aaatgccttc ttgctgtcct gtcggtctca gtacgttcac    60
tttatagctg ctggcaatat cgaa                                           84

<210> SEQ ID NO 326
<211> LENGTH: 67
<212> TYPE: DNA
<213> ORGANISM: Artificial Sequence
<220> FEATURE:
<223> OTHER INFORMATION: Amplicon

```
<400> SEQUENCE: 326
tgtggatgct ggattgattt caccactggt gcagctgcta aatagcaaag accaggaagt    60
gctgctt                                                              67

<210> SEQ ID NO 327
<211> LENGTH: 69
<212> TYPE: DNA
<213> ORGANISM: Artificial Sequence
<220> FEATURE:
<223> OTHER INFORMATION: Amplicon

<400> SEQUENCE: 327
agtgggagac acctgacctt tctcaagctg agattgagca gaagatcaag gagtacaatg    60
cccagatca                                                            69

<210> SEQ ID NO 328
<211> LENGTH: 68
<212> TYPE: DNA
<213> ORGANISM: Artificial Sequence
<220> FEATURE:
<223> OTHER INFORMATION: Amplicon

<400> SEQUENCE: 328
cccgttcggt ctgaggaagg ccgggacatg gcgaaccgga tcagtgcctt tggctacctt    60
gagtgctc                                                             68

<210> SEQ ID NO 329
<211> LENGTH: 69
<212> TYPE: DNA
<213> ORGANISM: Artificial Sequence
<220> FEATURE:
<223> OTHER INFORMATION: Amplicon

<400> SEQUENCE: 329
aacagagaca ttgccaacca tattggatct gcttgctgtc caaaccagca aacttcctgg    60
gcaaatcac                                                            69

<210> SEQ ID NO 330
<211> LENGTH: 86
<212> TYPE: DNA
<213> ORGANISM: Artificial Sequence
<220> FEATURE:
<223> OTHER INFORMATION: Amplicon

<400> SEQUENCE: 330
cgcgagcccc tcattataca ctgggcagcc tccccacagc gcatcgagga atgcgtgctc    60
tcaggcaagg atgtcaacgg cgagtg                                         86

<210> SEQ ID NO 331
<211> LENGTH: 77
<212> TYPE: DNA
<213> ORGANISM: Artificial Sequence
<220> FEATURE:
<223> OTHER INFORMATION: Amplicon

<400> SEQUENCE: 331
cagtggagac cagttgggta gtggtgactg ggtacgctac aagctctgca tgtgtgctga    60
tgggacgctc ttcaagg                                                   77

<210> SEQ ID NO 332
<211> LENGTH: 81
```

```
<212> TYPE: DNA
<213> ORGANISM: Artificial Sequence
<220> FEATURE:
<223> OTHER INFORMATION: Amplicon

<400> SEQUENCE: 332
gggctcagct tcagaagtg ctgagttggc agttttcttc tgtcaccaaa agaggtctca    60
atgtggacca gctgaacatg t                                             81

<210> SEQ ID NO 333
<211> LENGTH: 70
<212> TYPE: DNA
<213> ORGANISM: Artificial Sequence
<220> FEATURE:
<223> OTHER INFORMATION: Amplicon

<400> SEQUENCE: 333
tcacatgcca ctttggtgtt tcataatctc ctgggagaga ttgaccagca gtatagccgc    60
ttcctgcaag                                                          70

<210> SEQ ID NO 334
<211> LENGTH: 65
<212> TYPE: DNA
<213> ORGANISM: Artificial Sequence
<220> FEATURE:
<223> OTHER INFORMATION: Amplicon

<400> SEQUENCE: 334
gcccgaaacg ccgaatataa tcccaagcgg tttgctgcgg taatcatgag gataagagag    60
ccacg                                                               65

<210> SEQ ID NO 335
<211> LENGTH: 84
<212> TYPE: DNA
<213> ORGANISM: Artificial Sequence
<220> FEATURE:
<223> OTHER INFORMATION: Amplicon

<400> SEQUENCE: 335
gccgggaaga ccgtaattgt ggctgcactg gatgggacct tccagaggaa gccatttggg    60
gccatcctga acctggtgcc gctg                                          84

<210> SEQ ID NO 336
<211> LENGTH: 74
<212> TYPE: DNA
<213> ORGANISM: Artificial Sequence
<220> FEATURE:
<223> OTHER INFORMATION: Amplicon

<400> SEQUENCE: 336
tgctgttgct gagtctgttg ccagtcccca gaagaccatg tctgtgttga gctgtatctg    60
tgaagccagg caag                                                     74

<210> SEQ ID NO 337
<211> LENGTH: 66
<212> TYPE: DNA
<213> ORGANISM: Artificial Sequence
<220> FEATURE:
<223> OTHER INFORMATION: Amplicon

<400> SEQUENCE: 337
tgtggtgagg aaggagtcag agagctgtga ctgtctccag ggcttccagc tgacccactc    60
```

```
tctggg                                                                  66

<210> SEQ ID NO 338
<211> LENGTH: 89
<212> TYPE: DNA
<213> ORGANISM: Artificial Sequence
<220> FEATURE:
<223> OTHER INFORMATION: Amplicon

<400> SEQUENCE: 338
tggcttcagg agctgaatac cctcccaggc acacacaggt gggacacaaa taagggtttt      60
ggaaccacta ttttctcatc acgacagca                                        89

<210> SEQ ID NO 339
<211> LENGTH: 75
<212> TYPE: DNA
<213> ORGANISM: Artificial Sequence
<220> FEATURE:
<223> OTHER INFORMATION: Amplicon

<400> SEQUENCE: 339
gtatcaggac cacatgcagt acatcggaga aggcgcgaag acaggcatca aagaatgcca      60
gtatcaattc cgaca                                                       75

<210> SEQ ID NO 340
<211> LENGTH: 65
<212> TYPE: DNA
<213> ORGANISM: Artificial Sequence
<220> FEATURE:
<223> OTHER INFORMATION: Amplicon

<400> SEQUENCE: 340
tttccaaaca tcagcgagtc cacactggag agggagaagc accgtaactt tcaagcgctc      60
ctgtt                                                                  65
```

UNITED STATES PATENT AND TRADEMARK OFFICE
CERTIFICATE OF CORRECTION

PATENT NO. : 9,605,318 B2
APPLICATION NO. : 12/941877
DATED : March 28, 2017
INVENTOR(S) : Baker et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1184 days.

Signed and Sealed this
Thirteenth Day of March, 2018

Andrei Iancu
*Director of the United States Patent and Trademark Office*